US009102835B2

(12) United States Patent
Mao et al.

(10) Patent No.: US 9,102,835 B2
(45) Date of Patent: *Aug. 11, 2015

(54) METHODS OF USING DYES IN ASSOCIATION WITH NUCLEIC ACID STAINING OR DETECTION AND ASSOCIATED TECHNOLOGY

(71) Applicant: Biotium, Inc., Hayward, CA (US)

(72) Inventors: Fei Mao, Fremont, CA (US); Wai-Yee Leung, San Ramon, CA (US)

(73) Assignee: BIOTIUM, INC., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/962,668

(22) Filed: Aug. 8, 2013

(65) Prior Publication Data

US 2014/0073058 A1 Mar. 13, 2014

Related U.S. Application Data

(60) Continuation of application No. 13/541,313, filed on Jul. 3, 2012, now Pat. No. 8,753,814, which is a division of application No. 12/854,436, filed on Aug. 11, 2010, now Pat. No. 8,232,050, which is a continuation of application No. 12/484,968, filed on Jun. 15, 2009, now Pat. No. 7,803,943, which is a continuation of application No. 11/377,254, filed on Mar. 16, 2006, now Pat. No. 7,601,498.

(60) Provisional application No. 60/663,613, filed on Mar. 17, 2005.

(51) Int. Cl.
| | |
|---|---|
| C07D 221/06 | (2006.01) |
| C07D 455/04 | (2006.01) |
| C07D 471/04 | (2006.01) |
| C09B 15/00 | (2006.01) |
| C09B 11/28 | (2006.01) |
| C09B 23/04 | (2006.01) |
| C12Q 1/68 | (2006.01) |
| G01N 1/30 | (2006.01) |
| G01N 21/64 | (2006.01) |
| C07H 19/04 | (2006.01) |

(52) U.S. Cl.
CPC ............. *C09B 15/00* (2013.01); *C09B 11/28* (2013.01); *C09B 23/04* (2013.01); *C12Q 1/6818* (2013.01); *G01N 1/30* (2013.01); *G01N 21/6486* (2013.01); *Y10S 435/81* (2013.01); *Y10T 436/143333* (2015.01)

(58) Field of Classification Search
CPC ........ C09B 15/00; C09B 23/04; C09B 23/06; C09B 23/08; C09B 23/0091
USPC ............... 546/79, 80, 88; 536/26.6
See application file for complete search history.

(56) References Cited

U.S. PATENT DOCUMENTS

| | | |
|---|---|---|
| 4,883,867 A | 11/1989 | Lee et al. |
| 5,118,801 A | 6/1992 | Lizardi et al. |
| 5,210,015 A | 5/1993 | Gelfand et al. |
| 5,312,728 A | 5/1994 | Lizardi et al. |
| 5,321,130 A | 6/1994 | Yue et al. |
| 5,401,847 A | 3/1995 | Glazer et al. |
| 5,403,928 A | 4/1995 | Arrhenuis |
| 5,410,030 A | 4/1995 | Yue et al. |
| 5,436,134 A | 7/1995 | Haugland et al. |
| 5,445,946 A | 8/1995 | Roth et al. |
| 5,534,416 A | 7/1996 | Millard et al. |
| 5,538,848 A | 7/1996 | Livak et al. |
| 5,545,535 A | 8/1996 | Roth et al. |
| 5,582,977 A | 12/1996 | Yue et al. |
| 5,646,264 A | 7/1997 | Glazer et al. |
| 5,656,449 A | 8/1997 | Yue |
| 5,658,751 A | 8/1997 | Yue et al. |
| 5,691,146 A | 11/1997 | Mayrand |
| 5,763,162 A | 6/1998 | Glazer et al. |
| 5,846,726 A | 12/1998 | Nadeau et al. |
| 5,863,753 A | 1/1999 | Haugland et al. |
| 5,925,517 A | 7/1999 | Tyagi et al. |

(Continued)

FOREIGN PATENT DOCUMENTS

| | | | |
|---|---|---|---|
| EP | 1344835 | A2 | 9/2003 |
| EP | 1348713 | A2 | 10/2003 |
| EP | 1373250 | B1 | 8/2006 |
| JP | 2002327130 | | 11/2002 |
| WO | WO 2006/020947 | A2 | 2/2006 |
| WO | WO 2006/020947 | A3 | 8/2008 |

OTHER PUBLICATIONS

U.S. Appl. No. 12/976,917, filed Dec. 22, 2010, Mao et al.
U.S. Appl. No. 13/968,122, filed Aug. 15, 2013, Mao et al.
"Lab Ref: A Handbook of Recipes, Reagents, and Other Reference Tools for Use at the Bench," Electrophoresis of DNA, RNA, and Protein, Section 3A, 2002, pp. 62-80.
"Nucleic Acid Stains and Products for Genomics Studies," www.biotium.com—Fluorescent Probes and Related Biochemical Reagents for Life Science, Section 9, 2005-2006, pp. 161-173.

(Continued)

Primary Examiner — Jezia Riley
(74) Attorney, Agent, or Firm — Wilson Sonsini Goodrich & Rosati

(57) ABSTRACT

Methods of using dyes and associated technology are provided. A dye, such as a monomeric dye or a dimeric dye, may be used in a nucleic acid gel staining application and/or a nucleic acid detection application. Such a dye and a salt that comprises an anion that is associated with a strong acid and a cation that is associated with a strong base may be used in such an application. A dimeric dye, such as a dimeric dye capable of forming a hairpin-like structure, may be used to stain and/or detect nucleic acids via a release-on-demand mechanism. A dimeric dye having low background fluorescence in the absence of nucleic acids and high fluorescence in the presence of nucleic acids, upon binding therewith, may be used to stain and/or detect nucleic acids.

22 Claims, 14 Drawing Sheets

(56) References Cited

U.S. PATENT DOCUMENTS

| | | | |
|---|---|---|---|
| 5,977,344 | A | 11/1999 | Glazer et al. |
| 6,037,137 | A | 3/2000 | Komoriya et al. |
| 6,150,097 | A | 11/2000 | Tyagi et al. |
| 6,258,569 | B1 | 7/2001 | Livak et al. |
| 6,277,570 | B1 | 8/2001 | Wood et al. |
| 6,569,627 | B2 | 5/2003 | Wittwer et al. |
| 6,635,427 | B2 | 10/2003 | Wittwer et al. |
| 6,664,047 | B1 | 12/2003 | Haugland et al. |
| 7,166,478 | B2 | 1/2007 | Stavrianopoulos et al. |
| 7,387,887 | B2 | 6/2008 | Wittwer et al. |
| 7,601,498 | B2 | 10/2009 | Mao et al. |
| 7,776,567 | B2 | 8/2010 | Mao et al. |
| 7,803,943 | B2 | 9/2010 | Mao et al. |
| 8,232,050 | B2 | 7/2012 | Mao et al. |
| 2003/0008316 | A1 | 1/2003 | Smith et al. |
| 2003/0092062 | A1 | 5/2003 | Reddy et al. |
| 2004/0132046 | A1 | 7/2004 | Westman et al. |
| 2005/0239096 | A1 | 10/2005 | Beaudet et al. |
| 2006/0211028 | A1 | 9/2006 | Mao et al. |
| 2006/0211029 | A1 | 9/2006 | Mao et al. |
| 2010/0009454 | A1 | 1/2010 | Mao et al. |
| 2013/0167309 | A1 | 7/2013 | Mao et al. |

OTHER PUBLICATIONS

Adkins, et al. Visualization of DNA in Agarose Gels as Migrating Colored Bands: Applications for Preparative Gels and Educational Demonstrations. Analytical Biochemistry, vol. 240, Article No. 0325, 1996, pp. 17-23.

Albert, A. The Acridines. Their Preparation, Physical, Chemical, and Biological Properties, and Uses. Angew. Chem. internat. Edi, vol. 6, No. 10, 1967, 1 page.

Atwell, et al. Potential antitumor agents. 45. Synthesis, DNA-binding interaction, and biological activity of triacridine derivatives. J Med Chem. Jan. 1986;29(1):69-74.

Barak, et al. Fluorescent Low Density Lipoprotein for Observation of Dynamics of Individual Receptor Complexes on Cultured Human Fibroblasts, The Journal of Cell Biology, vol. 90, 1981, pp. 595-604.

Bengtsson, et al.,A New Minor Groove Binding Asymmetric Cyanine Reporter Dye for Real-Time PCR. Nucleic Acid Research, vol. 31, No. 8, 2003, pp. 1-5.

Benson, et al. Heterodimeric DNA-Binding Dyes Designed for Energy Transfer: Synthesis and Spectroscopic Properties. Nucleic Acids Research, vol. 21, No. 24, 1993, pp. 5727-5735.

Capelle, et al. Deoxyribonucleic Acid Bifunctional Intercalators: Kinetic Investigation of the Binding of Several Acridine Dimers to Deoxyribonucleic Acid. Biochemistry, vol. 18, No. 15, 1979, pp. 3354-3362.

Carreon, et al. Thiazole Orange-Peptide Conjugates: Sensitivity of DNA Binding to Chemical Structure. Organic Letters, vol. 6, No. 4, 2004, pp. 517-519.

Chakraborty, et al. Synthesis and DNA Binding Properties of Pyrrole Amino Acid-Containing Peptides. Tetrahedron Letters, vol. 46, 2005, pp. 647-651.

Dervan. Molecular Recognition of DNA by Small Molecules. Bioorganic & Medicinal Chemistry, vol. 9, 2001, pp. 2215-2235.

Eldho, et al. One Pot Synthesis of a Acridinylalkanoic Acids and Novel Bisacridines. Synthetic Communications, 29(22), 1999, pp. 4007-4014.

European search report and search opinion dated Feb. 14, 2012 for Application No. 11175090.7.

Fukunaga, et al. Production of Frameshift Mutations in *Salmonella* by Phenanthridinium Derivatives: Enzymatic Activation and Photoaffinity Labeling. Mutation Research, vol. 127, 1984, pp. 31-37.

Gaugain, et al. DNA Bifunctional Intercalators. 1. Synthesis and Conformational Properties of an Ethidium Homodimer and of an Acridine Ethidium Heterodimer. Biochemistry, vol. 17, No. 24, Nov. 28, 1978, pp. 5071-5078.

Gaugain, et al. DNA Bifunctional Intercalators. 2. Fluorescence Properties and DNA Binding Interaction of an Ethidium Homodimer and an Acridine Ethidium Heterodimer. Biochemistry, vol. 17, No. 24, 1978, pp. 5078-5088.

Gerlach, et al. Annalen Dr Physik, G Folge, Band 2, 1948, pp. 55-75.

Gong, et al., New DNA Minor-Groove Binding Molecules with High Sequence-Selectivities and Binding Affinities, Biochemical and Biophysical Communications, vol. 240, No. 3, 1997, pp. 557-560.

Guo, et al. DNA-Dye Fluorescence Enhancement Based on Shifting the Dimer-Monomer Equilibrium of Fluorescent Dye, Applied Spectroscopy, vol. 51, No. 7, 1997, pp. 1002-1007.

Hartwig, et al. Room-Temperature Palladium-Catalyzed Amination of Aryl Bromides and Chlorides and Extended Scope of Aromatic C—N Bond Formation with a Commercial Ligand. J. Org. Chem., vol. 64, 1999, pp. 5575-5580.

Haugland. Handbook of Fluorescent Probes and Research Products—Ninth Edition: Nucleic Acid Detection and Genomics Technology. Molecular Probes, Chapter 8, 2002, pp. 265-352.

Higuchi, et al. Simultaneous Amplification and Detection of Specific DNA Sequences. Bio/Technology, vol. 10, Apr. 1992, pp. 413-417.

Holland, et al. Detection of Specific Polymerase Chain Reaction Product by Utilizing the 5'→3' Exonuclease Activity of Thermus Aquaticus DNA Polymerase. Proc. Natl. Acad. Sci. USA, vol. 88, Aug. 1991, pp. 7276-7280.

Ishiguro, et al. Fluorescence Detection of Specific Sequence of Nucleic Acids by Oxazole Yellow-Linked Oligonucleotides. Homogeneous Quantitative Monitoring of in vitro Transcription. Nucleic Acids Research, vol. 24, No. 24, 1996, pp. 4992-4997.

Jackobsen, et al. Site selective bis-intercalation of a homodimeric thiazole orange dye in DNA oligonucleotides. Nucleic Acids Res. 1995; 23(5):753-60.

Joseph, et al. Tuning of Intercalation and Electron-Transfer Processes Between DNA and Acridinium Derivatives through Steric Effects. Bioconjugate Chem., vol. 15, 2004, pp. 1230-1235.

Kapuscinski, et al. Fluorescent Complexes of DNA with DAPI 4',6-diamidine-2-phenyl indole.2HCI or DCI 4',6-dicarboxyamide-2-phenyl indole. Nucleic Acid Research, vol. 5, No. 10, Oct. 1978, pp. 3775-3799.

Karsai, et al. Evaluation of a Homemade SYBR Green I Reaction Mixture for Real-Time PCR Quantification of Gene Expression. Biotechniques, Apr. 2002; 32(4): 790-2, 794-6.

Khairutdinov, et al. Photophysics of Cyanine Dyes: Subnanosecond Relaxation Dynamics in Monomers, Dimers, and H- and J-Aggregates in Solution. J. Phys. Chem. B, vol. 101, No. 14, 1997, pp. 2602-2610.

Latt, et al. Spectral Studies on 33258 HOECHST and Related Bisbenzimidazole Dyes Useful for Fluorescent Detection of Deoxyribonucleic Acid Synthesis. The Journal of Histochemistry and Cytochemistry, vol. 24, No. 1, 1976, pp. 24-33.

Lee, et al. Allelic Discrimination by Nick-Translation PCR with Fluorogenic Probes. Nucleic Acids Research, vol. 21, No. 16, 1993, pp. 3761-3766.

Lown, et al. Efficient Total Syntheses of the Oligopeptide Antibiotics Netropsin and Distamycin. J. Org. Chem., vol. 50, No. 20, 1985, pp. 3774-3779.

Mccann, et al. Detection of Carcinogens as Mutagens in the *Salmonella*/Microsome Test: Assay of 300 Chemicals. Proc. Nat. Acad. Sci. USA, No. 12, Dec. 1975, pp. 5135-5139.

Nath, et al., "Effects of Ethidium Bromide and SYBR Green I on Different Polymerase Chain Reaction Systems," Journal of Biochemical and Biophysical Methods, vol. 42, 2000, pp. 15-29.

Notification of transmittal of the international search report and the written opinion of the international searching authority, International Application No. PCT/US06/09910, mailed Mar. 29, 2007, 6 pages.

Office action dated Feb. 23, 2012 for U.S. Appl. No. 12/820,983.

Office action dated Jun. 20, 2013 for U.S. Appl. No. 13/541,313.

Office action dated Jul. 11, 2008 for U.S. Appl. No. 11/377,254.

Office action dated Aug. 9, 2011 for U.S. Appl. No. 12/854,436.

Office action dated Sep. 14, 2012 for U.S. Appl. No. 12/820,983.

Office action dated Sep. 29, 2009 for U.S. Appl. No. 11/377,253.

Office action dated Oct. 9, 2013 for U.S. Appl. No. 12/976,917.

(56) References Cited

OTHER PUBLICATIONS

Otto, et al. A Comparative Study of DAPI, DIPI, and HOECHST 33258 and 33342 As Chromosomal DNA Stains, Stain Technology, vol. 60, No. 1, 1985, pp. 7-11.

Parks, et al. Optimization of the Hairpin Polyamide Design for Recognition of the Minor Groove of DNA. J. Am. Chem. Soc., vol. 118, No. 26, 1996, pp. 6147-6152.

Perera. PCR Based Detection of Mycobacterium Tuberculosis: Effect of Sample Preparation. Southeast Asian J. Trop. Med Public Health, vol. 25, No. 4, Dec. 1994, pp. 693-697.

Rohatgi, et al. Thermodynamics of Dye Dimerization. Chemical Physics Letters, vol. 12, No. 2, Dec. 15, 1971, pp. 259-260.

Rohatgi, et al. Nature of Bonding in Dye Aggregates. The Journal of Physical Chemistry, vol. 70, No. 6, Jun. 1966, pp. 1695-1701.

Rye, et al. Stable fluorescent complexes of double-stranded DNA with bis-intercalating asymmetric cyanine dyes: properties and applications. Nucleic Acids Res. 1992; 20(11):2803-12.

Saiki, et al. Enzymatic Amplification of β-Globin Genomic Sequences and Restriction Site Analysis for Diagnosis of Sickle Cell Anemia. Science, vol. 230, Dec. 20, 1985, pp. 1350-1354.

Septinus, et al. Hydrophobic Acridine Dyes for Fluorescence Staining of Mitocondria in Living Cells: 1. Thermodynamic and Spectroscopic Properties of 10-n-Alkyl-Acridinium-Orange-Chlorides, Histochemistry, vol. 79, 1983, pp. 443-456.

Stryer, et al. Energy Transfer: A Spectroscopic Ruler. Proceedings of the National Academy of Sciences of the United States of America, vol. 58, No. 2, Aug. 15, 1967, pp. 719-726.

Sumner. Chromosome Banding and Identification. Methods in Molecular Biology: Chromosome Analysis Protocols, vol. 29, 1994, pp. 83-96.

Traganos, et al. Simultaneous Staining of Ribonucleic and Deoxyribonucleic Acids in Unfixed Cells Using Acridine Orange in a Flow Cytofluorometric System. www.jhc.org/cgi/content/abstract/25/1/46, 1 page. Accessed Mar. 2, 2005.

Tse, et al. A Fluorescent Intercalator Displacement Assay for Establishing DNA Binding Selectivity and Affinity. Accounts of Chemical Research, vol. 37, No. 1, 2004, pp. 61-69.

Ueda, et al. Single-Molecule Analysis of Chemotactic Signaling in Dictyostelium Cells. Science, vol. 294, Oct. 26, 2001, pp. 864-867.

Waring. Complex Formation Between Ethidium Bromide and Nucleic Acids. J. Mol. Biol., vol. 13, 1965, pp. 269-282.

West, et al. The Dimeric State of Cyanine Dyes. The Journal of Physical Chemistry, vol. 69, No. 6, Jun. 1965, pp. 1894-1903.

Wirth, et al. Interactions between DNA and mono-, bis-, tris-, tetrakis-, and hexakis(aminoacridines). A linear and circular dichroism, electric orientation relaxation, viscometry, and equilibrium study. J. Am. Chem. Soc. 1988; 110 (3):932-939.

Wittwer, et al. Continuous Fluorescence Monitoring of Rapid Cycle DNA Amplification. BioTechniques, vol. 22, No. 1, Jan. 1997, pp. 130-138.

Wolfe, et al. Simple, Efficient Catalyst System for the Palladium-Catalyzed Amination of Aryl Chlorides, Bromides, and Triflates, J. Org. Chem., vol. 65, 2000, pp. 1158-1174.

Yamagishi et al. Selective Activation of Reactant Molecules by Reversed Micelles. J. Phys. Chem., vol. 85, No. 3, 1981, pp. 281-285.

Yang, et al. Palladium-Catalyzed Amination of Aryl Halides and Sulfonates, Journal of Organometallic Chemistry, vol. 576, 1999, pp. 125-146.

Yarmoluk, et al. Interaction of cyanine dyes with nucleic acids—XXVII: synthesis and spectral properties of novel homodi- and homotrimeric monomethine cyanine dyes . Dyes and Pigments. 2001; 50:21-28.

Yunjing, et al. Study on Acridine Orange Dimer as a New Fluorescent Probe for the Determination of Protein. Anal. Commun., vol. 36, 1999, pp. 135-137.

Zimmerman, et al. Topologically constrained bifunctional intercalators: DNA intercalation by a macrocyclic bisacridine. J. Am. Chem. Soc. 1989; 111 (17):6805-6809.

Zipper, et al. Investigations on DNA Intercalation and Surface Binding by SYBR Green 1, Its Structure Determination and Methodological Implications. Nucleic Acid Research, vol. 32, No. 12, 2004, pp. 1-10.

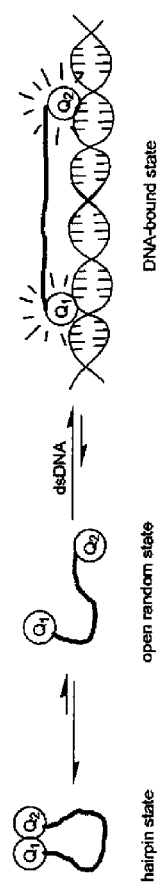
FIG. 1 DNA binding via a release-on-demand mechanism

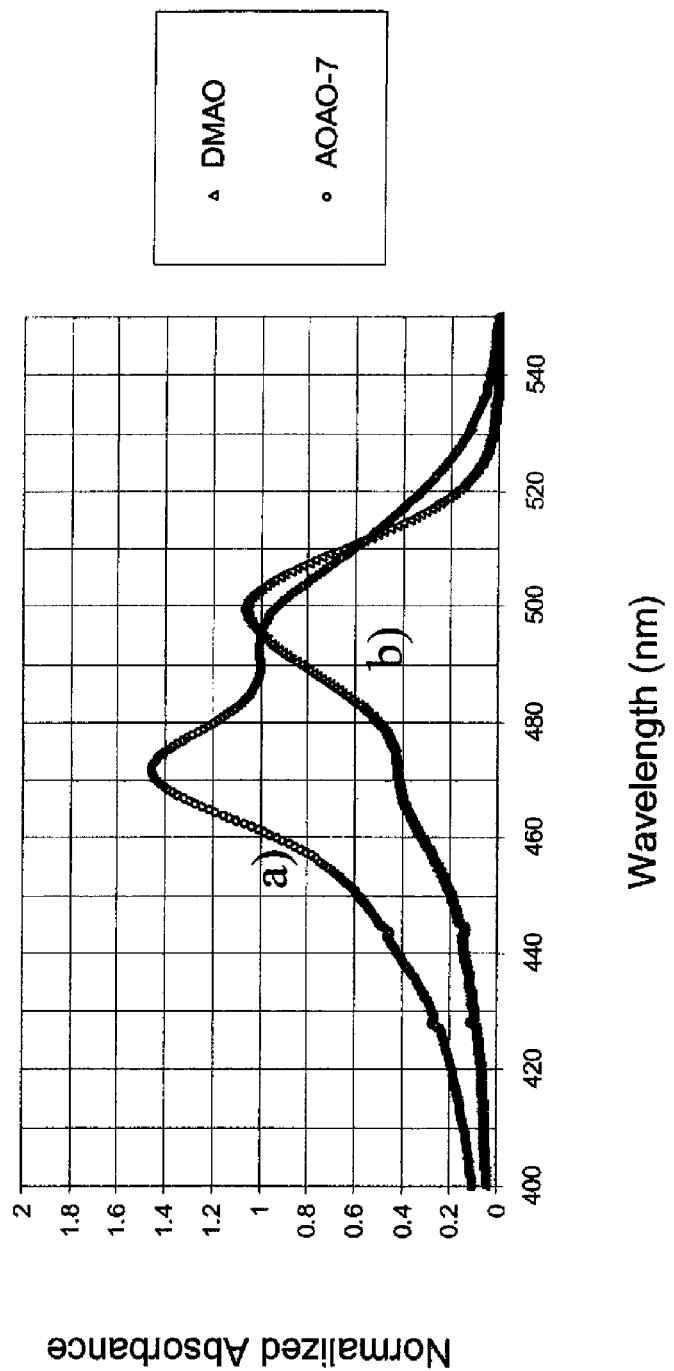
FIG. 2 Normalized absorbance spectra of DMAO and AOAO-7

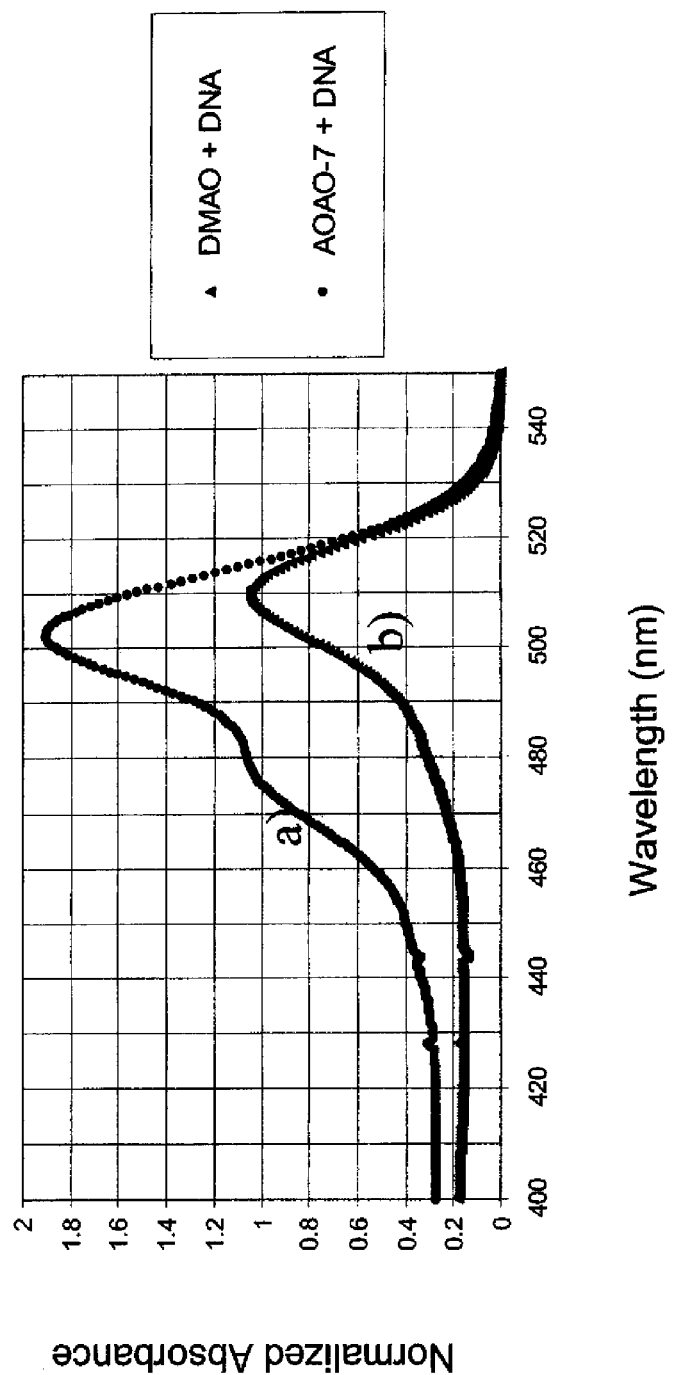
FIG. 3 Normalized absorbance spectra of DMAO and AOAO-7 in the presence of DNA

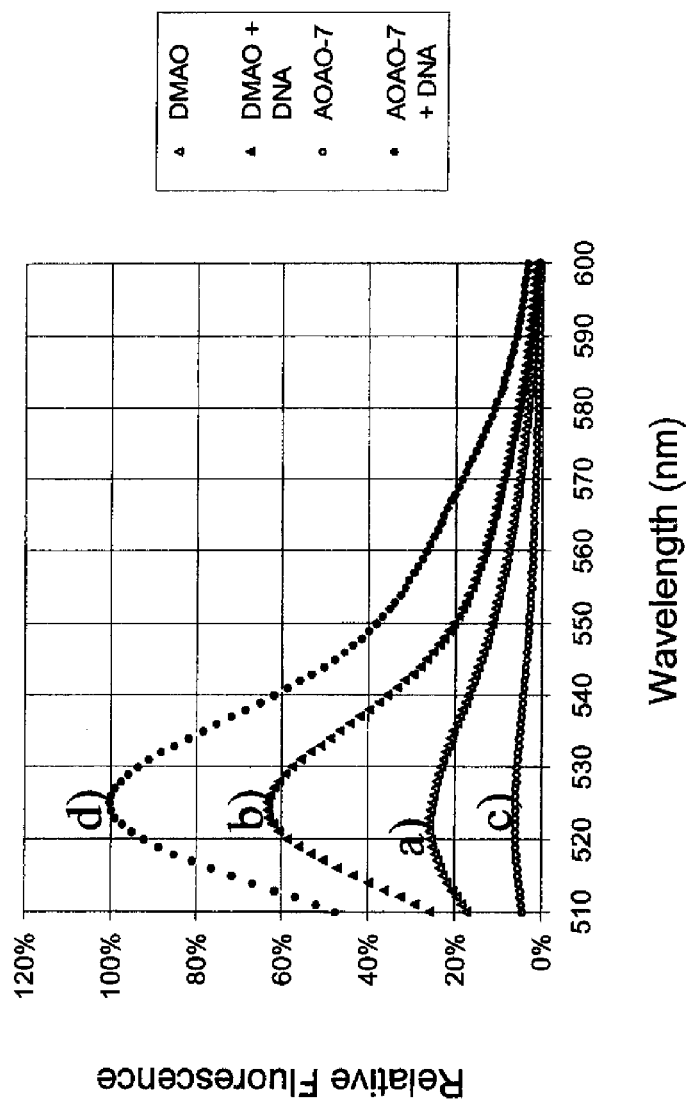
FIG. 4 Relative fluorescence spectra of DMAO and AOAO-7

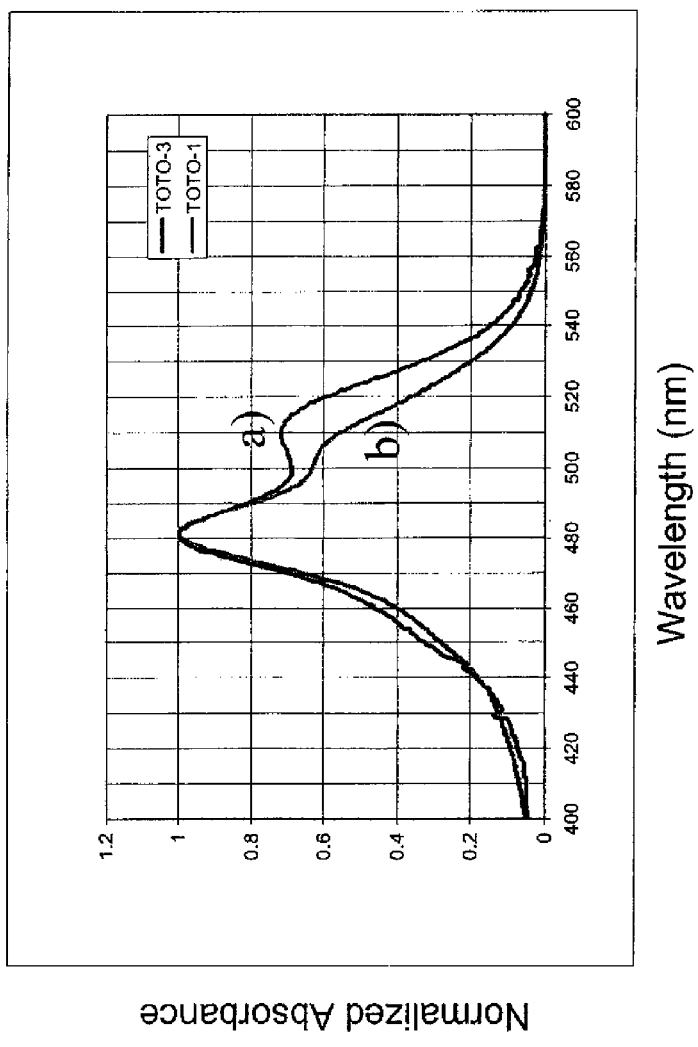
FIG. 5 Normalized absorbance spectra of TOTO-1 and TOTO-3

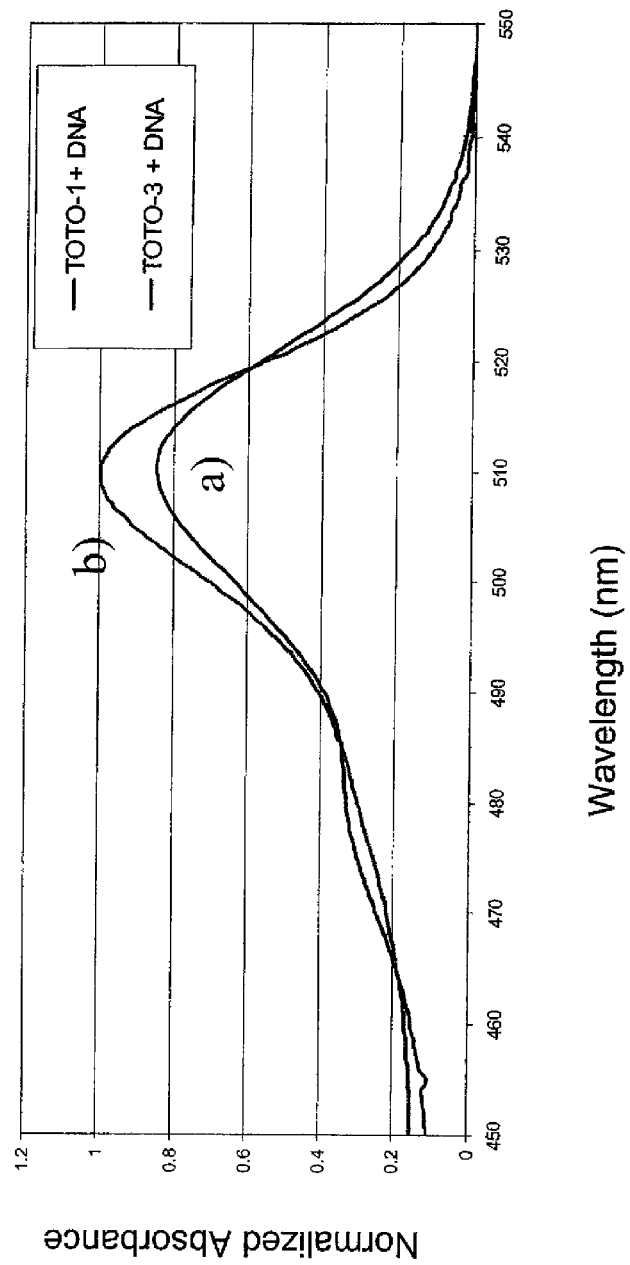
FIG. 6 Absorbance spectra of TOTO-1 and TOTO-3 in the presence of DNA

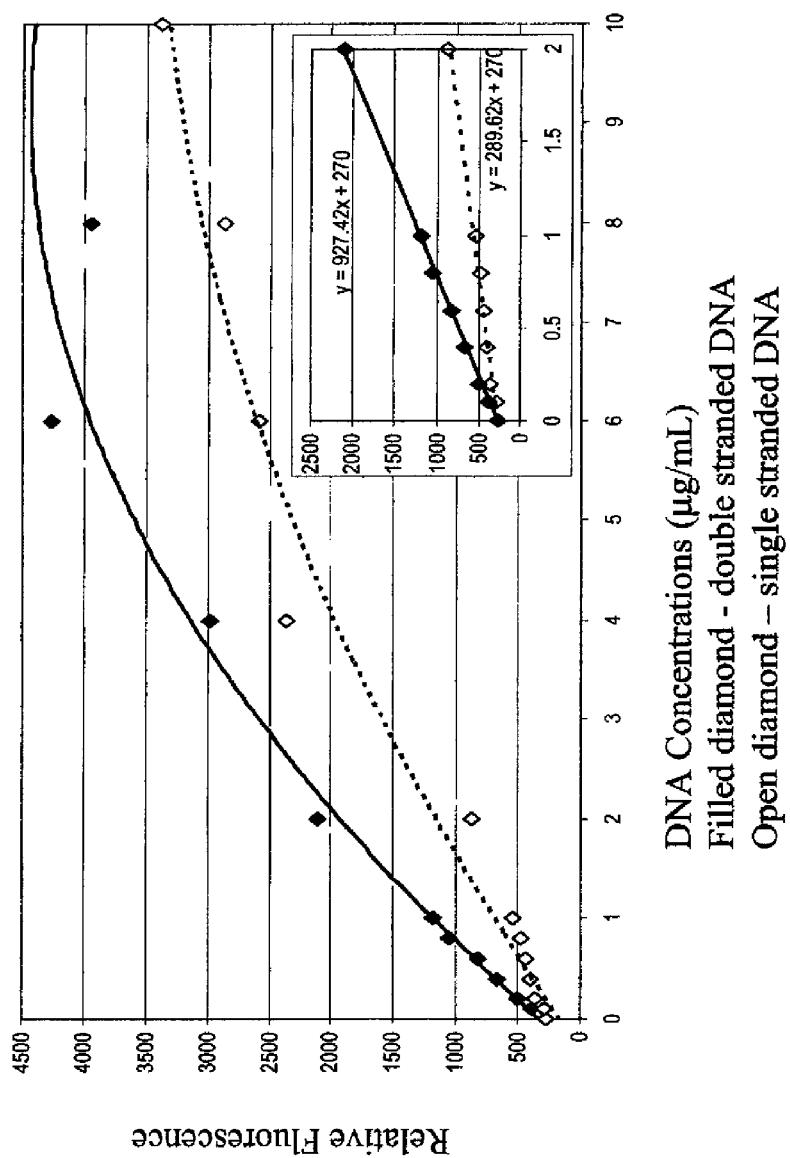
FIG. 7 Fluorescence response curve of AOAO-12 to DNA

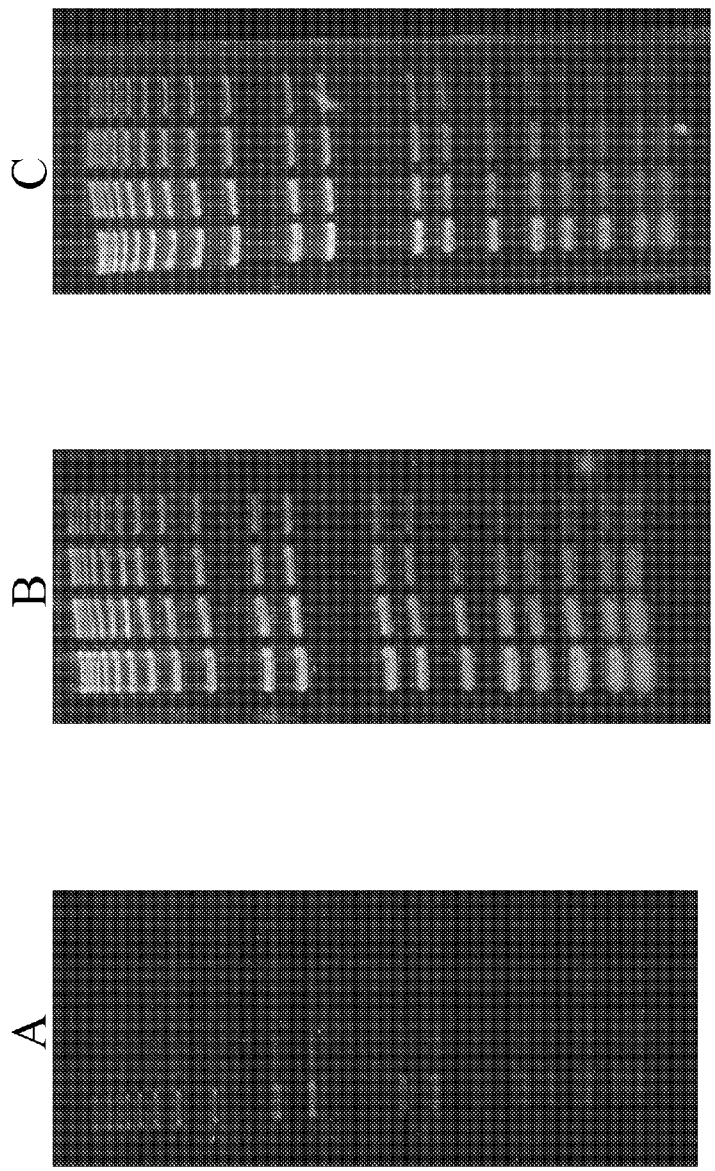
FIG. 8 Post-DNA Gel Staining with SYBR Safe, SYBR Green I and Dye No. 20 of Table 1

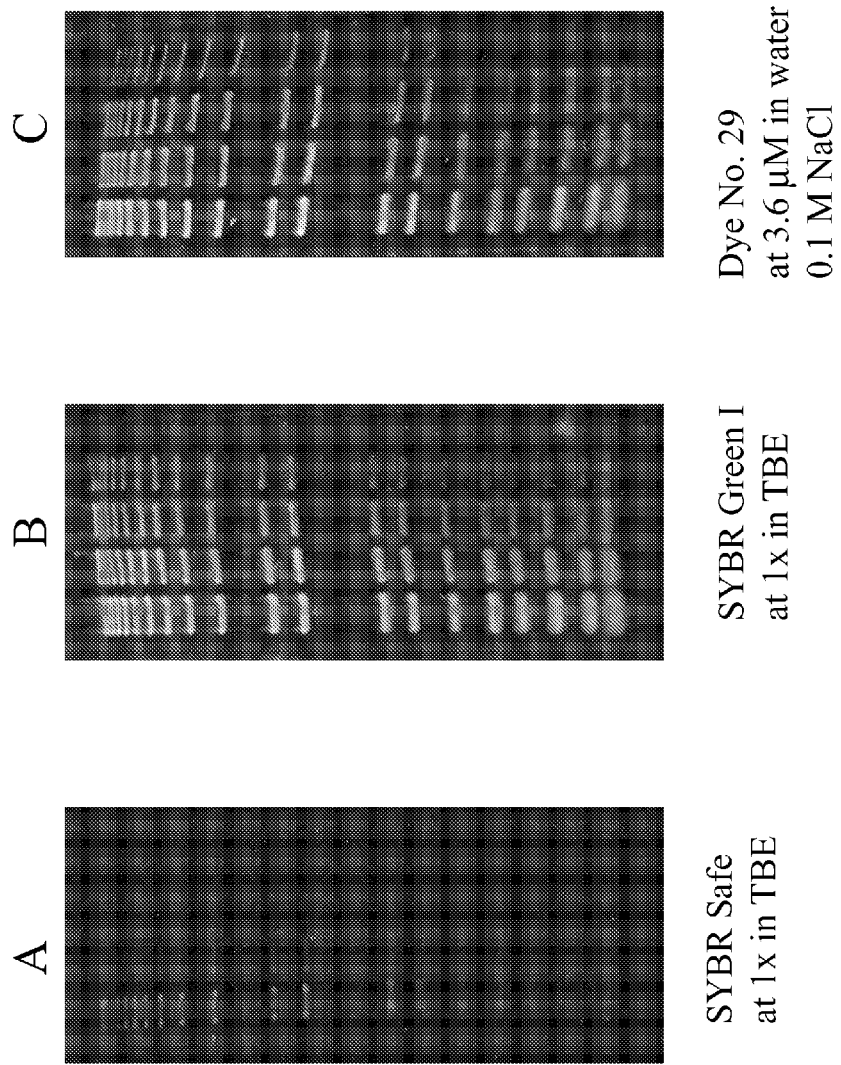
FIG. 9 Post-DNA Gel Staining with SYBR Safe, SYBR Green I and Dye No. 29 of Table 1

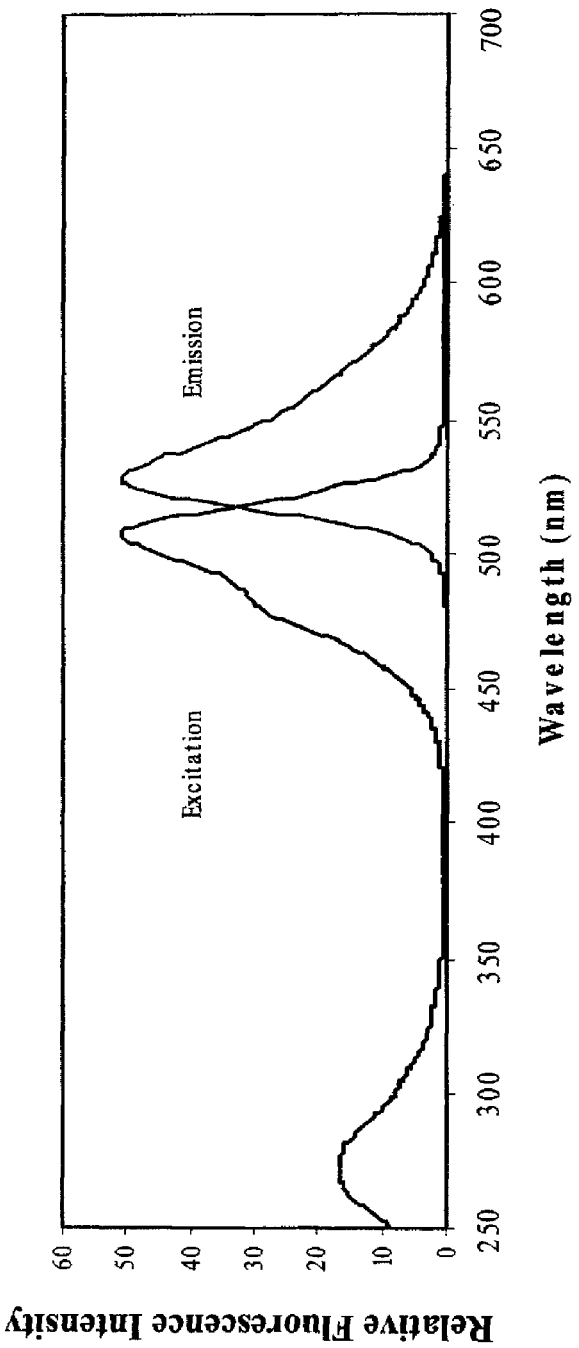
FIG. 10 Excitation and Emission Spectra of Dye No. 29 of Table 1 in the Presence of dsDNA

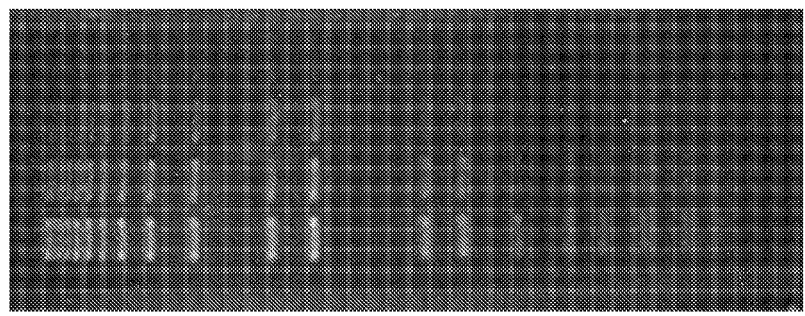
FIG. 11 Post-DNA Gel Staining with Dye No. 29 of Table 1

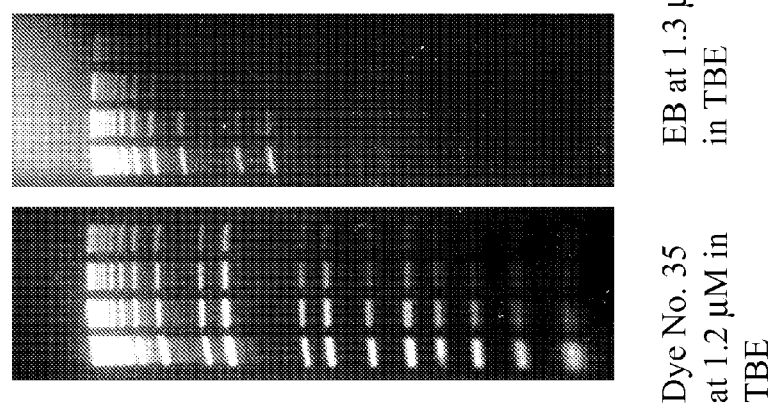
FIG. 12 Pre-Cast DNA Gel Staining with No. 35 of Table 1 and Ethidium Bromide

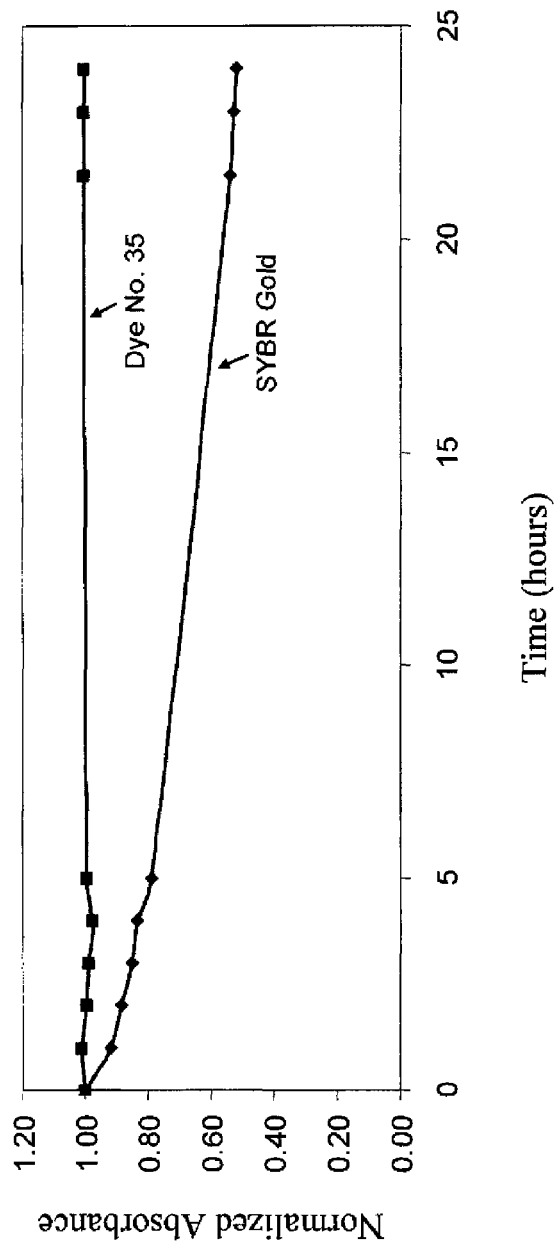
FIG. 13 Normalized Absorbance of Dye No. 35 of Table 1 and SYBR Gold in TBE Buffer

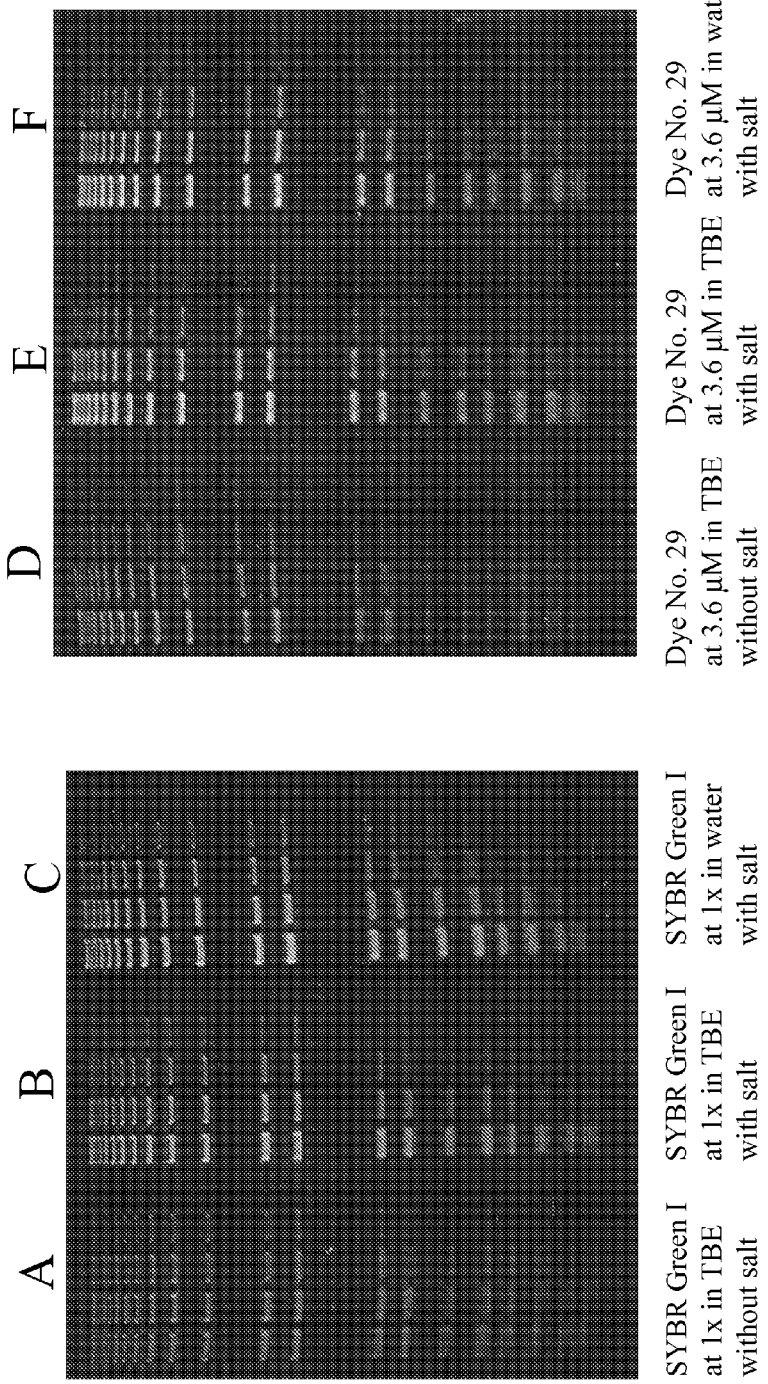
FIG. 14 Post-DNA Gel Staining with SYBR Green I and Dye No. 29 of Table 1, with and without salt

METHODS OF USING DYES IN ASSOCIATION WITH NUCLEIC ACID STAINING OR DETECTION AND ASSOCIATED TECHNOLOGY

CROSS-REFERENCE TO RELATED APPLICATIONS

This application is a continuation application of U.S. application Ser. No. 13/541,313, filed on Jul. 3, 2012, which claims the benefit of U.S. application Ser. No. 12/854,436, filed on Aug. 11, 2010, issued as U.S. Pat. No. 8,232,050 on Jul. 31, 2012, which is a divisional application of U.S. application Ser. No. 12/484,968, filed on Jun. 15, 2009, issued as U.S. Pat. No. 7,803,943 on Sep. 28, 2010, which is a continuation of U.S. application Ser. No. 11/377,254, filed on Mar. 16, 2006, issued as U.S. Pat. No. 7,601,498 on Oct. 13, 2009, which claims benefit under 35 U.S.C. §119(e) to U.S. Provisional Application No. 60/663,613 filed on Mar. 17, 2005, each of which is hereby incorporated by reference in their entirety.

BACKGROUND

Fluorescent dyes or stains can be used in the detection of nucleic acids, such as DNA and RNA, and biological samples involving nucleic acids. Nucleic acid polymers, such as DNA and RNA, are involved in the transmission of genetic information from one generation to the next and the routine functioning of living organisms. Nucleic acids are thus of interest and the objects of study. Fluorescent nucleic acid dyes that specifically bind to nucleic acids and form highly fluorescent complexes are useful tools for such study. These dyes can be used to detect the presence and quantities of DNA and RNA in a variety of media, including pure solutions, cell extracts, electrophoretic gels, micro-array chips, live or fixed cells, dead cells, and environmental samples.

Nucleic acids may be separated via gel electrophoresis, wherein the nucleic acids are placed in a gel, such as an agarose gel or a polyacrylamide gel, and electrophoretically separated. The separated nucleic acids may then be visualized. According to one method, referred to as post-gel staining or post-staining, the gel may be stained with a nucleic acid dye solution and then viewed with an appropriate transilluminator. According to another method, referred to as pre-cast staining, the gel may be premixed with the dye during gel preparation, prior to visualization. Such a gel that is pre-mixed, or pre-embedded, with a nucleic acid dye may be referred to as a pre-cast gel. Nucleic acids separated by a pre-cast gel can be visualized directly with a transilluminator.

Several dyes have been used as nucleic acid gel stains. For example, ethidium bromide (EB), a relatively inexpensive and adequately sensitive dye, has been used as a nucleic acid gel stain. EB is associated with several disadvantages however. First, EB is known to be a powerful mutagen and carcinogen, requiring special handling and waste disposal procedures (M. J. Waring, *J. Mol. Biol.I* 13, 269 (1965); McCann et al., *Proc. Natl. Acad. Sci. USA*, 72, 5135 (1975); and Fukunaga et al., *Mutation Res.* 127, 31 (1984)). Second, EB has significant intrinsic fluorescence, which contributes to background fluorescence, particularly for post-gel staining. This intrinsic fluorescence is significant in the sense that actual DNA bands, particularly, any relatively weak bands, may be indistinguishable relative to the background. Consequently, post-gel staining with EB typically requires a destaining step to remove background fluorescence. The extra destaining step results in not only inconvenience, but also in additional human exposure to the toxic material. Third, when EB is used in pre-cast gel staining, the dye tends to migrate in a direction opposite the direction of DNA migration. This usually leaves one end of the gel with a high dye concentration, which contributes to high background fluorescence, and the other end of the gel with an insufficient dye concentration, which lowers detection sensitivity.

Asymmetric cyanine dyes have been developed as alternatives to EB for nucleic acid gel stain applications. These dyes have been reported to be more sensitive than EB and to be more efficiently excited by the 488 nm argon laser. The asymmetric cyanine dye, SYBR Green I, has been marketed as both a pre-cast gel stain and a post-gel stain. However, the SYBR Green I dye has only limited stability in commonly used electrophoresis buffers, such that pre-cast gels prepared with the dye have to be used well within 24 hours before losing utility. The asymmetric cyanine dye, SYBR Gold, has been described as being more sensitive than SYBR Green I as a post-gel stain. However, the SYBR Gold dye cannot be used as a pre-cast gel stain because of its low stability. Another asymmetric cyanine dye, SYBR Safe, has been developed as an alternative to SYBR Green I and EB due to its low mutagenicity (U.S. Patent Application Publication No. 2005/0239096). However, this alternative dye is less sensitive than desired.

Development of fluorescent dyes or the making or the use thereof is desirable.

SUMMARY OF THE INVENTION

A method of producing, designing or using a fluorescent dye suitable for useful application, such as in nucleic acid gel staining, for example, is provided. The method may involve covalently linking two monomeric dyes via a bridge that is flexible and substantially neutral (for example, neutral or slightly charged).

A fluorescent dye suitable for useful application, such as that described above, for example, is provided. A dimeric dye, which may be produced according to a method described herein, may form a hairpin structure, which, it is believed, enables the dye to stain immobilized nucleic acids, such nucleic acids immobilized in a gel matrix, via a release-on-demand mechanism, as further described herein. A dye may have at least one feature, or all of the following features: relatively low "fluorescence background" (fluorescence in the absence of nucleic acids), if any, and ideally, no fluorescence background; relatively low toxicity, and ideally, no toxicity; relatively high fluorescent signal strength; and relative high stability. The dye is preferably better as to at least one of these features, and more preferably, as to all of these features, than an existing dye, such as EB, SYBR Green I or SYBR Safe, merely by way of example.

Dimeric nucleic acid dyes or stains that are capable of intramolecular dimer formation, or the formation of a hairpin structure, are provided. It is believed that a hairpin-shaped dye is non-fluorescent or is minimally fluorescent by itself, but becomes highly fluorescent in the presence of nucleic acids. It is believed that nucleic acid binding of the dye occurs via an intermediate state wherein the dye forms, in part, an open random conformation. It is further believed that this open random conformation of the dye exists in a small quantity and in equilibrium with the hairpin state. It is believed that as the amount of nucleic acids increases, an equilibrium shift from the hairpin state toward the nucleic acid-bound state of the dye occurs, such that the strength of the resulting fluorescence signal is substantially linearly proportional to the amount of nucleic acids present.

The above-described mechanism, which may be referred to as a release-on-demand mechanism of DNA staining, may be desirable for various applications, such as nucleic acid gel staining, for example. Merely by way of explanation, it is believed that formation of the hairpin structure renders the "effective dye concentration" low, such that a dye generally has low background fluorescence and low toxicity. Thus, as compared with previous dyes, such as EB or SYBR Green I, for example, a higher concentration of a dye described herein may be used in nucleic acid gel staining. This higher concentration of dye may increase DNA detection sensitivity, perhaps significantly, such as up to tenfold greater relative to that associated with EB, for example.

A method of determining presence or absence of nucleic acid in a sample is provided. When the sample is exposed to a matrix or a surface, nucleic acid present in the sample, if any, may become immobilized relative to the matrix or the surface. The method comprises exposing the sample to a fluorescent nucleic acid dye having the formula:

$$Q_1 \text{—} \boxed{\text{BRIDGE}} \text{—} Q_2,$$

wherein BRIDGE is a substantially aliphatic, substantially neutral linker comprising from about 8 to about 150 non-hydrogen atoms, inclusive; $Q_1$ is a fluorescent nucleic acid dye constituent; $Q_2$ is a fluorescent nucleic acid dye constituent; and $Q_1$ and $Q_2$ may be the same or different. This exposure is such that if nucleic acid is present in the sample, a complex of the fluorescent nucleic acid dye and the nucleic acid is formed. The method comprises detecting fluorescence associated with the complex, or a lack thereof. The method may be associated with pre-cast nucleic acid gel staining or post-nucleic acid gel staining, merely by way of example.

A kit for determining presence or absence of nucleic acid in a sample is provided. The kit comprises the fluorescent nucleic acid dye just described, and information concerning use of the fluorescent nucleic acid dye. The kit may comprise, optionally, a buffer and/or a gel matrix, at least one material for forming a gel matrix, a surface, or at least one material for forming a surface. The fluorescent nucleic acid dye may be in an aqueous solution or in a gel matrix, such as a agarose gel matrix, for example.

A method of post-nucleic acid gel staining a sample is provided. When the sample is exposed to a matrix or a surface, nucleic acid present in the sample, if any, may become immobilized relative to the matrix or the surface. The method comprises providing an aqueous solution comprising a fluorescent nucleic acid dye and a salt, and exposing the sample to the aqueous solution. The salt comprises an anion that would be sufficient as a component of a strong acid and a cation that would be sufficient as a component of such a strong acid a strong base.

These and various other aspects, features, and embodiments are further described herein.

BRIEF DESCRIPTION OF THE DRAWINGS

A detailed description of various aspects, features and embodiments is provided herein with reference to the accompanying drawings, which are briefly described below. The drawings are illustrative and are not necessarily drawn to scale. The drawings illustrate various aspects or features and may illustrate one or more embodiment(s) or example(s) in whole or in part. A reference numeral, letter, and/or symbol that is used in one drawing to refer to a particular element or feature may be used in another drawing to refer to a like element or feature.

FIG. 1 is a schematic illustration of DNA binding via a release-on-demand mechanism, in which three conformation states of the dye are in substantial equilibrium.

FIG. 2 is a graphical representation of normalized absorbance versus wavelength (nm), or normalized absorption spectra, of a) a dimeric dye, AOAO-7 (○), and b) a monomeric AO dye, DMAO (Δ), in PBS buffer.

FIG. 3 is a graphical representation of normalized absorbance versus wavelength (nm), or normalized absorption spectra, of a) a dimeric dye, AOAO-7 (●), and b) a monomeric AO dye, DMAO (▲), in a buffer and in the presence of DNA.

FIG. 4 is a graphical representation of relative fluorescence versus wavelength (nm), or fluorescence emission spectra, of DMAO (Δ) and AOAO-7 (○) in PBS buffer before DNA addition, a) and c), respectively, and DMAO (▲) and AOAO-7 (●) in PBS buffer after DNA addition, b) and d), respectively.

FIG. 5 is a graphical representation of normalized absorbance versus wavelength (nm), or normalized absorption spectra, of a) TOTO-1 (prepared according to U.S. Pat. No. 5,582,977) (darker line), and b) TOTO-3 (lighter line), in a buffer.

FIG. 6 is a graphical representation of normalized absorbance versus wavelength (nm), or normalized absorption spectra, of a) TOTO-1 according to U.S. Pat. No. 5,582,977) (darker line), and b) TOTO-3 (lighter line), in a buffer and in the presence of DNA.

FIG. 7 includes a graphical representation of relative fluorescence versus DNA concentration (μg/mL), or a titration, of single-stranded DNA (◇), and double-stranded DNA (◆), in solution and in the presence of AOAO-12 (at 0.2 μM). FIG. 7 also includes an inset graphical representation of relative fluorescence versus DNA concentration that shows a substantially linear relationship between the two.

FIG. 8 includes photograph A of a gel upon post-DNA gel staining with SYBR Safe at 1× in TBE; photograph B of a gel upon post-DNA gel staining with SYBR Green I at 1× in TBE; and photograph C of a gel upon post-DNA gel staining with Dye No. 20 of Table 1 at 3.6 μM in TBE, each as viewed via a 254-nm UV light transilluminator. The amount of DNA loading per lane, or column, from left to right, as shown in each of the photographs, was 200 ng, 100 ng, 50, ng, and 25 ng, respectively. Photographs A, B and C were taken using a SYBR filter and Polaroid 667 black-and-white print film.

FIG. 9 includes photograph A of a gel upon post-DNA gel staining with SYBR Safe at 1× in TBE; photograph B of a gel upon post-DNA gel staining with SYBR Green I at 1× in TBE; and photograph C of a gel upon post-DNA gel staining with Dye No. 29 (TOTO-13) of Table 1 at 3.6 μM in water with 0.1 M NaCl, each as viewed via a 254-nm UV light transilluminator. The amount of DNA loading per lane, or column, from left to right, as shown in each of the photographs, was 200 ng, 100 ng, 50, ng, and 25 ng, respectively. Photographs A, B and C were taken using a SYBR filter and Polaroid 667 black-and-white print film.

FIG. 10 is a graphical representation of the relative fluorescence intensity of excitation and emission spectra (nm) of Dye No. 29 (TOTO-13) of Table 1 in the presence of dsDNA.

FIG. 11 is a photograph of a gel upon post-DNA gel staining with Dye No. 29 of Table 1 at 3.6 3.6 μM in water with 0.1 M NaCl, as viewed via a Dark Reader visible light transilluminator from Clare Chemical Research (Dolores, Colo. (CO)). The amount of DNA loading per lane, or column, from left to right, as shown in the photograph, was 200 ng, 100 ng, 50, ng, and 25 ng, respectively. The photograph was taken using a SYBR filter and Polaroid 667 black-and-white print film.

FIG. 12 includes a photograph of a gel upon pre-cast DNA gel staining with Dye No. 35 (ET-27) of Table 1 at 1.2 µM in TBE and a photograph of a gel upon pre-cast DNA gel staining with EB at 1.3 µM in TBE, each as viewed via a 300-nm UV light transilluminator. The amount of DNA loading per lane, or column, from left to right, as shown in each of the photographs, was 200 ng, 100 ng, 50, ng, and 25 ng, respectively. The photographs were taken using a SYBR filter and Polaroid 667 black-and-white print film.

FIG. 13 is a graphical representation of normalized absorbance of Dye No. 35 (ET-27) of Table 1 at about 1.2 µM in TBE and normalized absorbance of SYBR Gold at 1× effective working concentration in TBE, over time (hours) at room temperature.

FIG. 14 includes a photograph A of a gel upon post-DNA gel staining with SYBR Green I at 1× in 1×TBE; a photograph B of a gel upon post-DNA gel staining with SYBR Green I at 1× in 1×TBE with 0.1 M NaCl; a photograph C of a gel upon post-DNA gel staining with SYBR Green I at 1× in H$_2$O with 0.1 M NaCl; a photograph D of a gel upon post-DNA gel staining with Dye No. 29 of Table 1 at 3.6 µM in 1×TBE; a photograph E of a gel upon post-DNA gel staining with Dye No. 29 of Table 1 at 3.6 µM in 1×TBE with 0.1 M NaCl; and a photograph F of a gel upon post-DNA gel staining with Dye No. 29 of Table 1 at 3.6 µM in H$_2$O with 0.1 M NaCl, each as viewed via a 254-nm UV light transilluminator. The amount of DNA loading per lane, or column, from left to right, as shown in each of the photographs, was 200 ng, 100 ng, 50, ng, and 25 ng, respectively. The photographs were taken using a SYBR filter and Polaroid 667 black-and-white print film.

DESCRIPTION

Fluorescent dyes or stains may be useful in various applications, such as nucleic acid detection, for example. Methods associated with fluorescent dyes or stains, such as methods of use thereof, for example, may also be useful. Dimeric nucleic acid dyes, such as those having low background fluorescence in the absence of nucleic acids and relatively greater fluorescence in the presence of nucleic acids, such as immobilized nucleic acids, for example, may also be useful. Dimeric nucleic acid dyes may be useful in various applications, such as nucleic acid detection in gels, for example. Useful dyes or stains, and associated technology, such as methods of using same, for example, are described herein.

Herein, it will be understood that a word appearing in the singular encompasses its plural counterpart, and a word appearing in the plural encompasses its singular counterpart, unless implicitly or explicitly understood or stated otherwise. Further, it will be understood that for any given component described herein, any of the possible candidates or alternatives listed for that component, may generally be used individually or in any combination with one another, unless implicitly or explicitly understood or stated otherwise. Additionally, it will be understood that any list of such candidates or alternatives, is merely illustrative, not limiting, unless implicitly or explicitly understood or stated otherwise. Still further, it will be understood that any figure or number or amount presented herein is approximate, and that any numerical range includes the minimum number and the maximum number defining the range, whether or not the term "inclusive" or the like appears, unless implicitly or explicitly understood or stated otherwise. Additionally, it will be understood that any permissive, open, or open-ended language encompasses any relatively permissive to restrictive language, open to closed language, or open-ended to closed-ended language, respectively, unless implicitly or explicitly understood or stated otherwise. Merely by way of example, the word "comprising" may encompass "comprising"-, "consisting essentially of"-, and/or "consisting of"-type language.

Various terms are generally described or used herein to facilitate understanding. It will be understood that a corresponding general description or use of these various terms applies to corresponding linguistic or grammatical variations or forms of these various terms. It will also be understood that a general description or use or a corresponding general description or use of any term herein may not apply or may not fully apply when the term is used in a non-general or more specific manner. It will also be understood that the terminology used or the description provided herein, such as in relation to various embodiments, for example, is not limiting. It will further be understood that embodiments described herein or applications described herein, are not limiting, as such may vary.

Generally, the terms "stain" and "dye" may be used interchangeably and refer to an aromatic molecule capable of absorbing light in the spectral range of from about 250 nm to about 1,200 nm, inclusive. Generally, the term "dye" may refer to a fluorescent dye, a non-fluorescent dye, or both. Generally, the term "fluorescent dye" refers to a dye capable of emitting light when excited by another light of appropriate wavelength.

Generally, the term "fluorescence quencher" refers to a molecule capable of quenching the fluorescence of another fluorescent molecule. Fluorescence quenching can occur via at least one of the three ways. The first type of fluorescence quenching occurs via fluorescence resonance energy transfer (FRET) (Förster, *Ann. Phys.* (1948); and Stryer, et al., *Proc. Natl. Acad. Sci.* (1967)), wherein a quencher absorbs the emission light from a fluorescent molecule. The absorption peak of a FRET quencher usually has to have significant overlap with the emission peak of a fluorescent dye for the FRET quencher to be an efficient fluorescent quencher. A FRET quencher is typically a non-fluorescent dye, but can also be a fluorescent dye. When a quencher is a fluorescent dye, only the absorption property of the dye is utilized. A second type of fluorescence quenching occurs via photo-induced electron transfer (PET), wherein the quencher is an electron-rich molecule that quenches the fluorescence of a fluorescent molecule by transferring an electron to the electronically excited dye. A third type of fluorescence quenching occurs via dye aggregation, such as H-dimer formation, wherein two or more dye molecules are in physical contact with one another, thereby dissipating the electronic energy into the vibrational modes of the molecules. This type of contact fluorescence quenching can occur between two identical fluorescent dyes, or between two different fluorescent dyes, or between a fluorescent dye and a FRET quencher, or between a fluorescent dye and a PET quencher. Other types of fluorescence quenchers, though not used as commonly, include stable free radical compounds and certain heavy metal complexes.

Generally, the term "nucleic acid" refers to double-stranded DNA (dsDNA), single-stranded DNA (ssDNA), double-stranded RNA (dsRNA), single-stranded RNA (ss-RNA), and/or derivatives thereof. A nucleic acid may be natural or synthetic.

Generally, the term "fluorescent nucleic acid stain" or "fluorescent nucleic acid dye" refers to a dye capable of binding to a nucleic acid to form a fluorescent dye-nucleic acid complex. A fluorescent nucleic acid dye is typically non-fluorescent or weakly fluorescent by itself, but becomes highly fluorescent upon nucleic acid binding. Generally, the term "non-fluorescent, nucleic acid-binding molecule" refers to a nucleic acid-binding molecule that may or may not be a dye and that does not become fluorescent upon binding to nucleic acid. Generally, the term "fluorescent DNA dye" refers to a dye that becomes fluorescent upon binding to DNA. Generally, the term "fluorescent, non-nucleic acid dye" refers to a fluorescent dye that does not bind to nucleic acid. Generally, the term "non-fluorescent, non-nucleic acid dye" refers to a dye that is neither fluorescent nor nucleic acid-binding. Such a dye is commonly called a fluorescence quencher. Frequently, a fluorescence quencher is used to form a FRET pair with a fluorescent dye. Generally, the term "reporter dye" refers to a fluorescent dye whose emitted fluorescence contributes to the final detected fluorescence signal.

Generally, the term "TBE" refers to an aqueous buffer comprising about 89 mM Tris, about 89 mm borate, and about 2 mM EDTA, with a pH of about 8.3; the term "TAE" refers to an aqueous buffer comprising about 40 mM Tris, about 20 mM acetate, and about 2 mM EDTA, with a pH of about 8.1; and the term "EB" refers to ethidium bromide.

Generally, a salt that comprises a cation that is associated with a strong base and an anion that is associated with a strong acid refers to a salt that comprises such a cation and such an anion from whatever source, whether from the strong acid or strong base or from any other suitable source. The strong base may have a pKa of about 10 or greater, and the strong acid may have a pKa of about 2 or less. In this regard, "a cation that is associated with a strong base" generally refers to a cation that would be sufficient as a component of such a strong base, but need not actually be such a component, and "an anion that is associated with a strong acid" generally refers to an anion that would be sufficient as a component of such a strong acid, but need not actually be such a component. Merely by way of example, the salt may be one that when dissolved in water is sufficiently ionized, such as on the order of at least 90% ionized, for example. A concentration of such a salt in solution may be from about 5 mM to about 0.5 M, inclusive, such as about 0.05 M to about 0.2 M, or about 0.1 M, for example. Such a salt may be non-buffering. Generally, when a non-buffering salt is dissolved in water, it fully dissociates into the cation and anion without significantly changing the pH of the water. In this regard, a significant change may be a pH change of ±0.5, inclusive, such as ±0.3, inclusive, for example. Examples of such salts include, but are not limited to, sodium chloride, potassium chloride, sodium sulfate, potassium sulfate, sodium bromide, potassium bromide, tetramethylammonium chloride, magnesium chloride, and/or the like.

In general, fluorescent nucleic acid dyes can be classified into two major classes: intercalators and minor groove-binders. Generally, fluorescent intercalators are dyes that bind to double-stranded DNA (dsDNA) or double-stranded RNA (dsRNA) by inserting themselves in between a neighboring base pair. Generally, minor groove-binders are dyes that bind to the minor groove of double-stranded DNA. There are still other dyes that may bind to nucleic acids via multiple modes, including electrostatic interaction between a positively charged dye and the negatively charged nucleic acid.

A method for designing a fluorescent nucleic acid dye for detecting immobilized nucleic acids, such as for detecting nucleic acids in gels, is now described. The method comprises covalently linking two monomeric dyes with a suitable linker to form a dimeric dye. The dimeric dye, when in solution, assumes a predominantly hairpin-like conformation due to intramolecular dimer formation. This hairpin-like conformation or state of the dye is inactive with respect to nucleic acids, or incapable of interacting or groove-binding with nucleic acids. It is believed that the dye, when in solution and in the presence of nucleic acids, also assumes an open random conformation or state, which exists in small quantity and in substantial equilibrium with the hairpin conformation. The open random conformation or state of the dye is active with respect to nucleic acids, or capable of interacting or binding with nucleic acids. It is believed that when the dye is in the presence of an increasing amount of nucleic acids, an equilibrium shift from the hairpin state toward the intermediate, open random state, or DNA-binding state, occurs. It is believed that this mechanism, sometimes referred to as a "release-on-demand DNA-binding mechanism," reduces background fluorescence and sometimes may also reduce the toxicity of the dye. As a consequence, the dye may be used in nucleic acid gel staining at a higher concentration than might otherwise be possible, and thus, may provide for greater nucleic acid detection sensitivity than might otherwise be possible.

The dimeric dye may posses any number of desirable characteristics. By way of example, such a dye may have a background fluorescence that is reduced relative to that of its monomeric dye constituents. Relatively low background fluorescence generally corresponds to relatively enhanced nucleic acid detection sensitivity. Thus, such a dimeric dye is generally associated with enhanced nucleic acid detection sensitivity. Further by way of example, a dimeric dye may be more thermally and/or hydrolytically stable than SYBR Green I. Still further by way of example, a dimeric dye may be less toxic, particularly less mutagenic, than some of the dyes previously used in nucleic acid gel stains.

A fluorescent dimeric nucleic acid dye may have the general structure (Structure 1) set forth directly below.

Structure 1

In relation to the brief summary and the description, references to a dimeric dye are to a dimeric dye of Structure 1. In Structure 1, each of $Q_1$ and $Q_2$ is a fluorescent nucleic acid dye. $Q_1$ and $Q_2$ may be selected and combined in a manner to encourage or to ensure desired properties of the resulting dimeric dye. BRIDGE may be positively charged to a relatively limited extent or substantially neutral in charge, and may be a substantially flexible constituent that facilitates intramolecular dimer formation to produce the dimeric dye.

BRIDGE may be a substantially flexible linker molecule, having no more than one positive charge. BRIDGE may be a substantially neutral and substantially flexible linker molecule. The constituents of BRIDGE may be selected to provide such limited positive charge or substantial neutrality. The property of substantial neutrality, which includes actual neutrality, is discussed further below. The property of substantial flexibility is generally related to the substantially aliphatic nature, which includes actual aliphatic nature, of BRIDGE. This substantial aliphatic nature generally refers to the non-aromaticity of BRIDGE, or non-rigidity of BRIDGE.

In Structure 1, BRIDGE is covalently attached to $Q_1$ and $Q_2$. In a dimeric dye, BRIDGE may generally have from about 8 to about 150 non-hydrogen atoms, inclusive; from about 10 to about 100 non-hydrogen atoms, inclusive; from about 15 to about 80 non-hydrogen atoms, inclusive; or from about 20 to about 50 non-hydrogen atoms, inclusive.

BRIDGE may incorporate at least one independent nucleic-acid-binding-enhancing-group (NABEG). A NABEG is a moiety capable of binding to nucleic acids in the form of electrostatic, hydrophobic, or hydrogen-bonding interactions. Merely by way of example, a NABEG may be selected from primary amines; secondary amines; tertiary amines; ammoniums; amidines; aryl groups optionally comprising hetero atoms selected from N, O, S, and any combination thereof moieties having bonds comprising hetero atoms of high electronegativity; and any combination thereof.

Primary, secondary and tertiary amines and amidines are basic groups and therefore are positively charged or at least partially positively charged at physiological pH. Ammonium groups, or quaternized nitrogen groups, are permanently positively charged. Generally speaking, positively charged or partially positively charged groups enhance the nucleic acid binding of the dye via electrostatic interaction, a property that may be exploited in the development of highly sensitive fluorescent nucleic acid stains. It is generally undesirable to use BRIDGE having excessive positive charges to produce a dimeric dye. A suitable BRIDGE of a dimeric dye may comprise no more than one positive charge. BRIDGE may be a substantially flexible and neutral or substantially neutral linker. In this context, substantially neutrality refers to slight charge. By way of example, BRIDGE could comprise a weakly basic constituent, such as a pyridine group or a pyrazine group, for example, such that when it is in aqueous solution, a very small amount of positive charges may be present. Further by way of example, in a case in which BRIDGE comprises at least one neutral NABEG, the exact amount of positive charge is generally related to the $pK_a$ of the NABEG. Generally, the higher the $pK_a$ of the NABEG, the more likely the NABEG is protonated and thus, positively charged. By way of example, a suitable weakly basic NABEG group may have a $pK_a$ of about 11 or less, inclusive; about 8 or less, inclusive; or about 7 or less, inclusive.

There may be a tendency to form an intramolecular dimer, primarily H-dimer, which may be a particularly useful property in the nucleic acid dye produced. For example, in the case of a dimeric dye, H-dimer formation produces a hairpin-like structure, wherein H-dimer forms a stem portion of the hairpin and BRIDGE forms a curved portion, as schematically illustrated in FIG. 1. The phenomenon of H-dimer formation in connection with certain dyes has been described in West, et al., *J. Phys. Chem.* (1965); Rohatgi, et al., *J. Phys. Chem.* (1966); Rohatgi, et al., *Chem. Phys. Lett.* (1971); and Khairutdinov, et al., *J. Phys. Chem.* (1997). Formation of an intramolecular H-dimer may be facilitated when BRIDGE is a flexible and neutral or substantially neutral hydrocarbon linker, optionally comprising one or more neutral NABEG(s).

H-dimer formation may be characterized by a large blue shift of the dye absorption spectrum. By way of example, the absorption spectra of a monomeric dye AO (acridine orange) and a related dimeric dye, AOAO-7, that forms an intramolecular dimer, are shown in FIG. 2. The 471 nm peak associated with the AOAO-7 dimer indicates intramolecular H-dimer formation. The absorption spectra of both the monomer and the dimer become similar once DNA-binding occurs, indicating the opening up of the hairpin structure. By way of example, as shown in FIG. 3, the disappearance of the 471 nm peak from AOAO-7 dimer indicates the opening up of the hairpin structure upon DNA binding.

H-dimer formation in a dimeric dye may be associated with two major benefits. One of the major benefits is a reduction, sometimes dramatic, in background fluorescence, coupled with a substantial increase in fluorescence upon DNA-binding, as demonstrated by a large gain in the fluorescence signal. This benefit may be appreciated by comparing the fluorescence spectra of a monomeric acridine orange dye, DMAO, and a dimeric acridine orange dye, AOAO-7, in the absence and presence of DNA. For example, as shown in FIG. 4, relative to the monomeric DMAO dye, the dimeric AOAO-7 dye is associated with lower background fluorescence and higher fluorescence upon binding to DNA.

Intramolecular dimer-associated fluorescence quenching may be so efficient that a dimeric dye may be constructed from at least one monomeric dye that is not normally considered to be very desirable, such as at least one monomeric dye that has high background fluorescence, for example. An example of this is shown in FIG. 4, which features acridine orange (AO) and a dimer thereof. Although AO is one of the earliest known nucleic acid-binding dyes and has desirable wavelengths, it has not been widely used for nucleic acid detection because of its relatively high background fluorescence. As demonstrated in FIG. 4, relative to the monomeric AO dye, the dimeric dye AOAO-7 has much lower background fluorescence.

H-dimer formation in a dimeric dye may be associated with another major benefit. This unexpected benefit is that H-dimer formation in a dimeric dye may significantly reduce the toxicity, particularly mutagenicity, of the dye. In this regard, a significant reduction in mutagenicity may be on the order of at least about 20% relative to EB, as measured using the Ames Test or an equivalent test. It is believed that reduced mutagenicity may be at least partly attributable to reductions in the cell membrane-permeability and the effective concentration of the dye. The molecular weight of a dimeric dye is generally substantially or significantly larger, such as about two times larger, for example, than the molecular weights of known nucleic acid gel stains. Generally, a molecule having a larger molecular weight has more difficulty penetrating cell membranes than a molecule having a smaller molecular weight. As such, a molecule having a large molecular weight may be relatively less likely to enter a cell and cause cell damage. As to a dimeric dye molecule that successfully enters a cell, the effective concentration of the dye associated with the molecule is generally relatively small because of H-dimer formation. As such, the dimeric dye molecule may be relatively less likely to cause cell damage once it enters a cell.

BRIDGE may have the formula (Formula 1) set forth directly below.

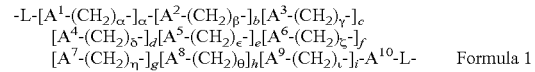

Formula 1

In Formula 1, each L is part of BRIDGE and is covalently linked to $Q_1$ or $Q_2$. Each L is independently a moiety comprising a single bond; a polymethylene unit having 1 carbon to about 12 carbons, inclusive, optionally comprising at least one hetero atom selected from N, O and S; or an aryl group optionally comprising at least one hetero atom selected from N, O and S. The subscripts associated with the $(CH_2)$ methylene units, namely, $\alpha, \beta, \gamma, \delta, \epsilon, \zeta, \eta, \theta$, and $\iota$, may be the same or different, each independently indicating the size of the associated methylene unit and, independently, being zero or an integer from 1 to about 20, inclusive, or from 1 to about 12, inclusive. The subscripts associated with the bracketed portions of Formula 1, namely, a, b, c, d, e, f, g, h, and i, may be the same or different, each independently indicating the size of the associated bracketed portion of the formula and, independently, being zero or an integer from 1 to about 20, inclusive, or from 1 to about 10, inclusive, or from 1 to about 5, inclusive.

$A^1, A^2, A^3, A^4, A^5, A^6, A^7, A^8, A^9$, and $A^{10}$ may be the same or different, each independently, being a nucleic-acid-binding-enhancing-group (NABEG); a branched alkyl optionally comprising at least one hetero atom selected from N, O and S; or at least one saturated 5- or 6-membered ring optionally comprising at least one hetero atom selected from N, O and S. $A^1, A^2, A^3, A^4, A^5, A^6, A^7, A^8, A^9$, and $A^{10}$ may be such that BRIDGE comprises at most one positive charge, or is substantially neutral, and in the latter case, each of these constituents, independently, may itself be substantially neutral, which includes actual neutrality. NABEGs may be selected from moieties comprising at least one bond linkage that comprises at least one hetero atom of high electronegativity or S; and aryl groups optionally comprising at least one hetero atom selected from halogens, N, O, and S. Examples of moieties comprising at least one bond linkage that comprises at least one hetero atom of high electronegativity or S include, but are not limited to moieties comprising at least one amide bond, urethane bond, urea bond, thiourea bond, ether bond, or thioether bond.

$A^1, A^2, A^3, A^4, A^5, A^6, A^7, A^8, A^9$, and $A^{10}$, which may be the same or different, may, independently, be NABEGs selected from moieties comprising at least one bond linkage that comprises at least one hetero atom of high electronegativity or S; and aryl groups optionally comprising at least one hetero atom selected from halogens, N, O, and S. Examples of moieties comprising at least one bond linkage that comprises at least one hetero atom of high electronegativity or S include, but are not limited to moieties comprising at least one amide bond, urethane bond, urea bond, thiourea bond, ether bond, or thioether bond. $A^1, A^2, A^3, A^4, A^5, A^6, A^7, A^8, A^9$, and $A^{10}$ may be such that BRIDGE comprises at most one positive charge, or is substantially neutral, and in the latter case, each of these constituents may itself be substantially neutral, which includes actual neutrality.

BRIDGE may comprise any suitable number of non-hydrogen atoms, as previously described, such as from about 10 to about 100 non-hydrogen atoms, inclusive, merely by way of example.

Merely by way of example, BRIDGE may have the formula (Formula 2) set forth directly below.

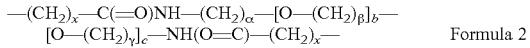

Formula 2

In one such case, for example, each L of BRIDGE is —$(CH_2)_x$—, where each x, independently, is an integer selected from 1 to 11, inclusive; $A^1$ of BRIDGE is —C(=O)NH—; a of BRIDGE is 1; $A^2$ of BRIDGE is —O—; $A^3$ of BRIDGE is —O—; α may be an integer selected from 2 to about 20, inclusive; each of β and γ, independently, may be 2 or 3; b may be zero or an integer selected from 2 to about 20; and c may be zero or 1; each of d, e, f, g, h and i of BRIDGE is 0; and $A^{10}$ of BRIDGE is —NH(O=C)C—. Merely by way of example, BRIDGE may be as just described, wherein c is 1. Further, merely by way of example, BRIDGE may be as just described, wherein c is 1, and further, wherein x may be 5; α and γ may be the same and may be 2 or 3; β may be 2; and b may be 0, 1, 2 or 3.

Each of the constituent monomeric dyes, Q1 and Q2, of the dimeric dye is a fluorescent nucleic acid dye. In general, Q1 and Q2 are selected and covalently linked via BRIDGE in a manner to encourage or to ensure intramolecular dimer formation in the absence of DNA and formation of highly fluorescent DNA-dye complexes upon DNA binding. A dimeric dye may have a tendency to form an intramolecular dimer as may be associated with the formation of a useful hairpin-like structure, as previously described. Such a dimeric dye may possess desirable properties, such as low background fluorescence and low toxicity, for example.

Intramolecular dimer formation may be confirmed by comparing absorption spectra of a dimeric dye in an aqueous solution and absorption spectra of the related monomeric dye or dyes also in an aqueous solution. Any intramolecular dimer formation should cause the spectra of the component monomeric dyes in the dimeric dye to be shifted significantly relative to the spectra of the related monomeric dye(s). In this regard, a significant shift may be about 10 nm or more, by way of example. For example, in FIG. 2, the spectra associated with AOAO-7 are shifted significantly relative to the spectra of DMAO.

When the intramolecular dimer formation is an H-dimer formation, the spectra will usually undergo a significant blue shift. In this regard, a significant shift may be about 10 nm or more, by way of example. Other types of intramolecular dimer formation are also possible and may result in spectral shift in another direction, in insignificant spectral shift, or the like. In this regard, an insignificant shift may be about 5 nm or less, by way of example. Additional analytical methods for detecting intramolecular dimer formation may include nuclear magnetic resonance (NMR), infrared spectroscopy (IR), or the like. Any intramolecular dye aggregation that results in a hairpin structure is generally desirable.

Various combinations of $Q_1$ and $Q_2$ may be useful or desirable. By way of example, examples of dimeric dyes and associated intermediates are listed below in Table 1.

TABLE 1
Prepared Fluorescent Nucleic Acid Dyes
| No. | Name | Structure | MWt. | SPACER LENGTH (ATOMS) |
|---|---|---|---|---|
| 1 | DMAO | 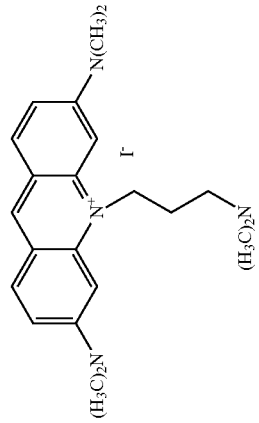 | 478.41 | N/A |
| 2 | TMAO | 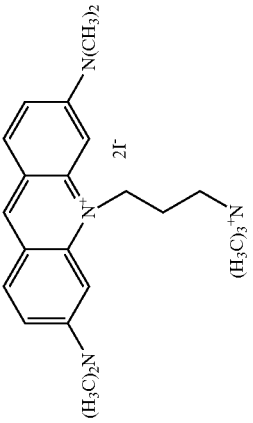 | 620.35 | N/A |

TABLE 1-continued
Prepared Fluorescent Nucleic Acid Dyes
| No. | Name | Structure | MWt. | SPACER LENGTH (ATOMS) |
|---|---|---|---|---|
| 3 | AO-3N | 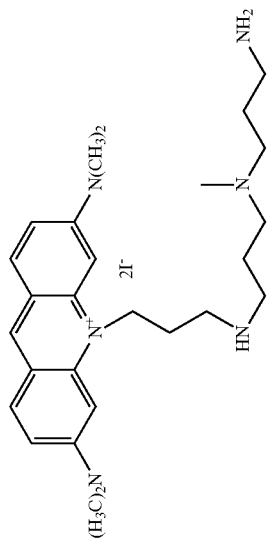 | 705.16 | N/A |
| 4 | AO-2N | 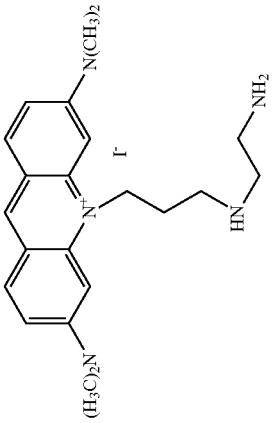 | 493.43 | N/A |

TABLE 1-continued

Prepared Fluorescent Nucleic Acid Dyes

| No. | Name | Structure | MWt. | SPACER LENGTH (ATOMS) |
|---|---|---|---|---|
| 5 | PMAO | 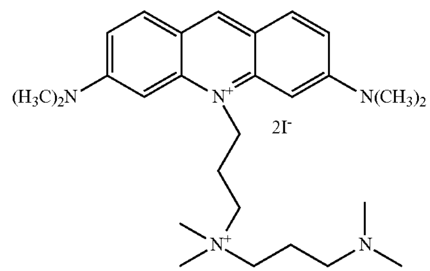 | 691.47 | N/A |
| 6 | AOAO-1 | 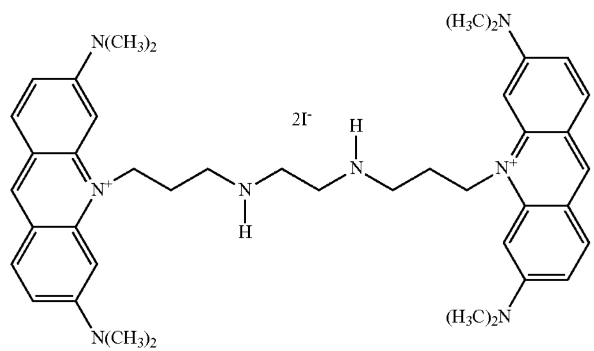 | 926.76 | 10 |

TABLE 1-continued

Prepared Fluorescent Nucleic Acid Dyes

| No. | Name | Structure | MWt. | SPACER LENGTH (ATOMS) |
|---|---|---|---|---|
| 7 | AOAO-2 | (structure shown) 2r⁻ | 1124.03 | 21 |
| 8 | AOAO-3 | (structure shown) 2r⁻ | 1038.88 | 16 |

TABLE 1-continued
Prepared Fluorescent Nucleic Acid Dyes
| No. | Name | Structure | MWt. | SPACER LENGTH (ATOMS) |
|---|---|---|---|---|
| 9 | AOAO-2Q | 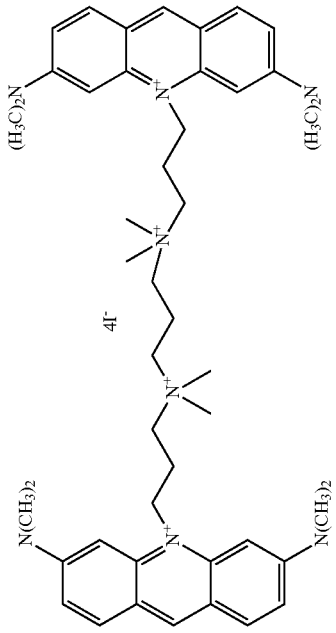 | 1252.71 | 11 |
| 10 | AOAO-4 | 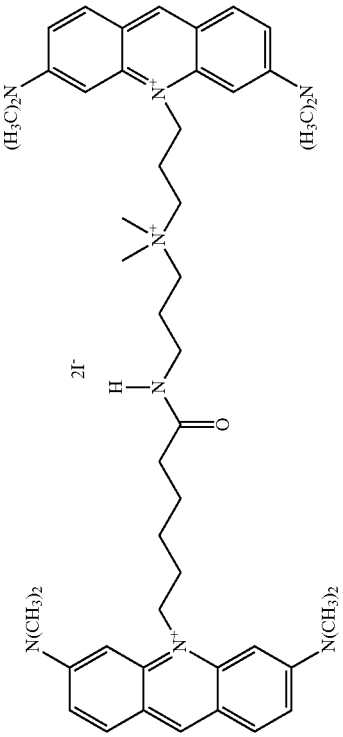 | 1041.95 | 14 |

TABLE 1-continued
Prepared Fluorescent Nucleic Acid Dyes
| No. | Name | Structure | MWt. | SPACER LENGTH (ATOMS) |
|---|---|---|---|---|
| 11 | AOAO-5 | 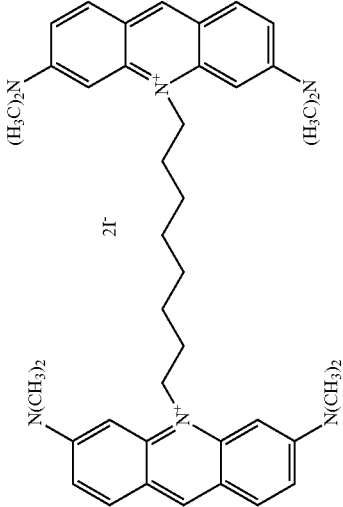 | 896.73 | 8 |
| 12 | AOAO-6 | 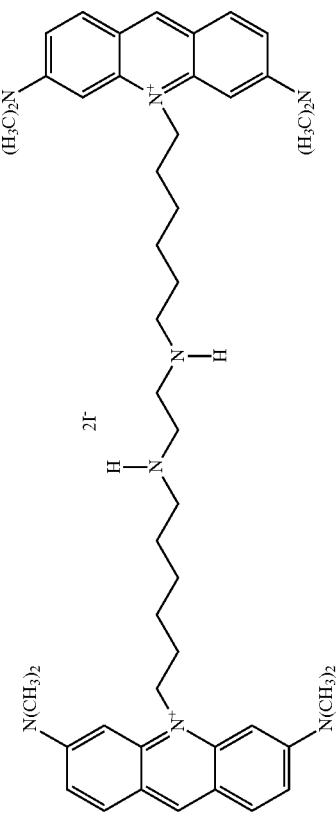 | 1010.92 | 16 |

TABLE 1-continued
Prepared Fluorescent Nucleic Acid Dyes
| No. | Name | Structure | MWt. | SPACER LENGTH (ATOMS) |
|---|---|---|---|---|
| 13 | AOAO-7 | 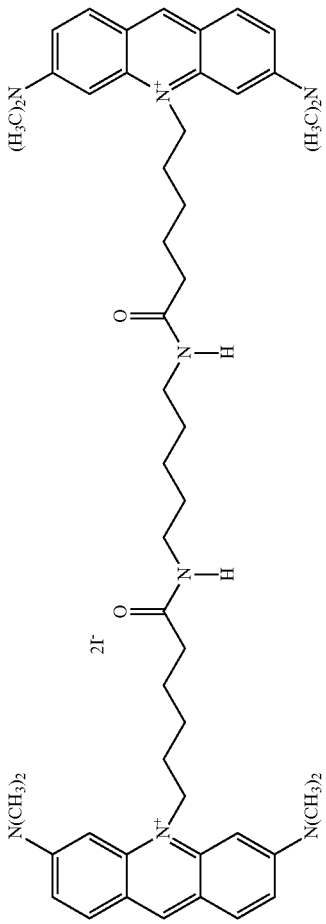 | 1080.96 | 19 |
| 14 | TOTO-3 | 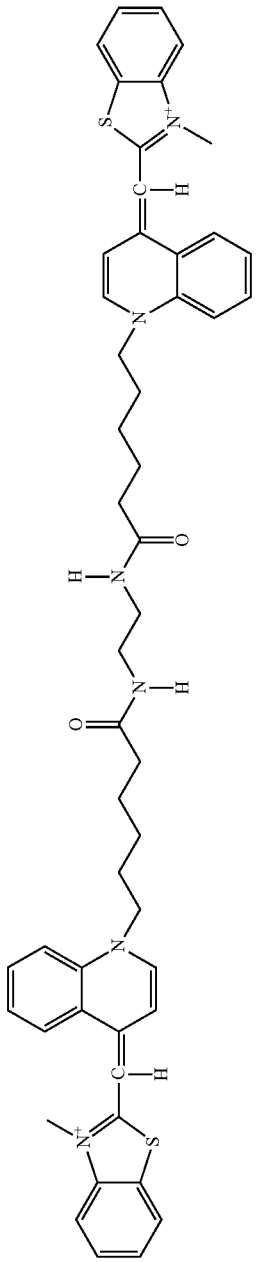 | 1088.94 | 16 |

TABLE 1-continued

Prepared Fluorescent Nucleic Acid Dyes

| No. | Name | Structure | MWt. | SPACER LENGTH (ATOMS) |
|---|---|---|---|---|
| 15 | AOAO-8 | 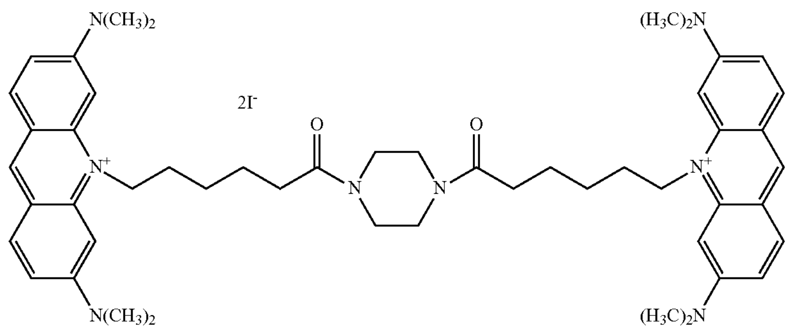 | 1064.92 | 16* |
| 16 | AOAO-9 | 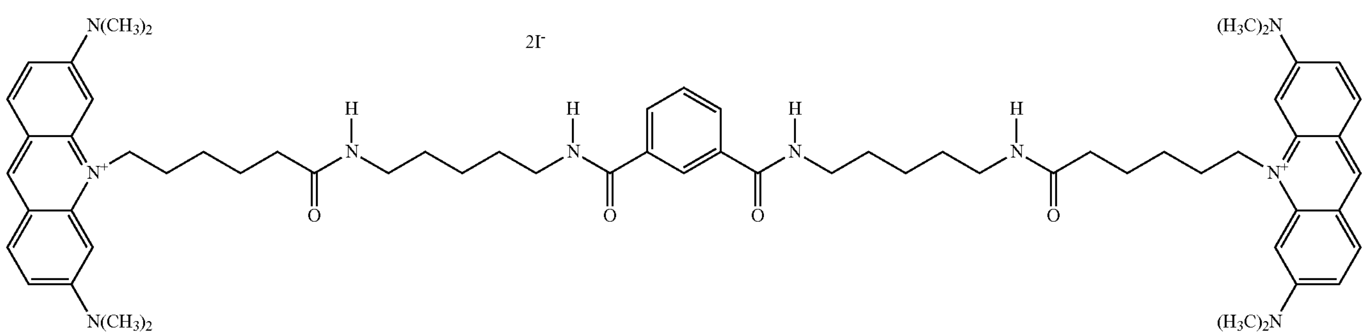 | 1229 | 25 |

TABLE 1-continued

Prepared Fluorescent Nucleic Acid Dyes

| No. | Name | Structure | MWt. | SPACER LENGTH (ATOMS) |
|---|---|---|---|---|
| 17 | AOAO-10 | (structure) | 1313.24 | 31 |
| 18 | AOAO-11 | (structure) | 1123 | 22 |

TABLE 1-continued
Prepared Fluorescent Nucleic Acid Dyes
| No. | Name | Structure | MWt. | SPACER LENGTH (ATOMS) |
|---|---|---|---|---|
| 19 | AOAO-12 | 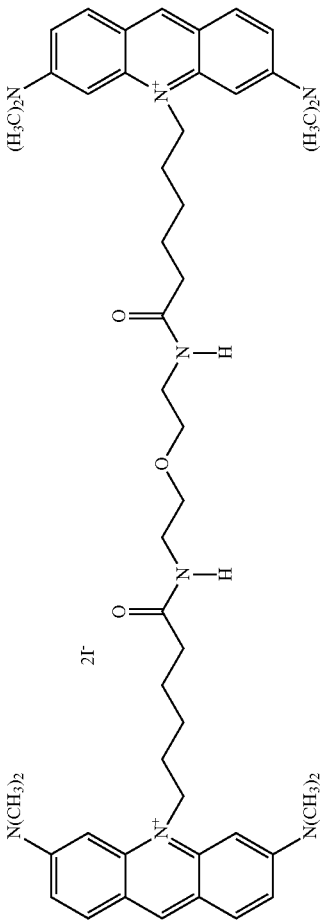 | 1082.94 | 19 |
| 20 | AOAO-13 | 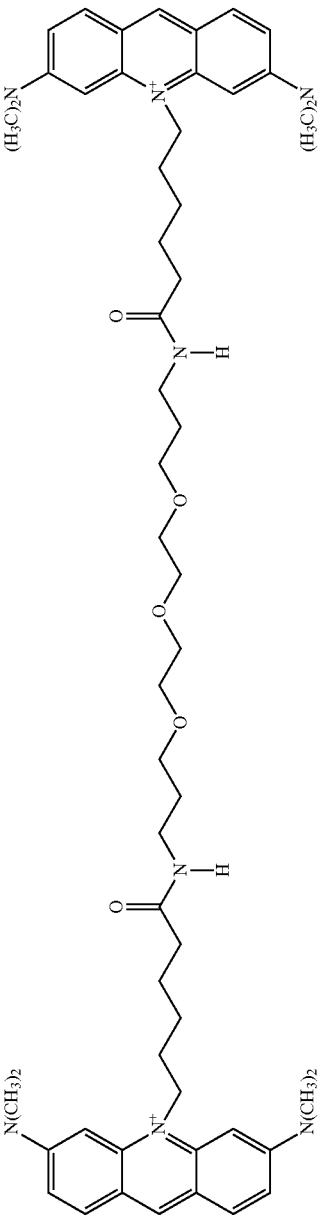 | 1215.14 | 27 |

TABLE 1-continued
Prepared Fluorescent Nucleic Acid Dyes
| No. | Name | Structure | MWt. | SPACER LENGTH (ATOMS) |
|---|---|---|---|---|
| 21 | AOAO-14 | 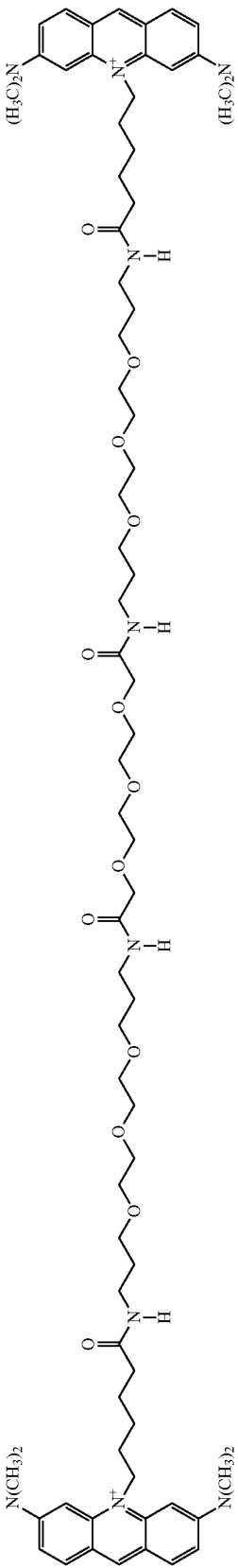 | 1621.61 | 53 |
| 22 | AOAO-12R | 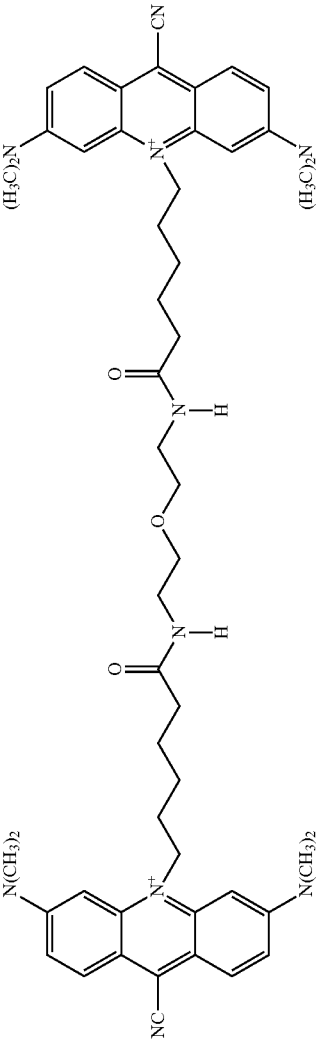 | 1132.95 | 19 |

TABLE 1-continued

Prepared Fluorescent Nucleic Acid Dyes

| No. | Name | Structure | MWt. | SPACER LENGTH (ATOMS) |
|---|---|---|---|---|
| 23 | AOTO-3 | 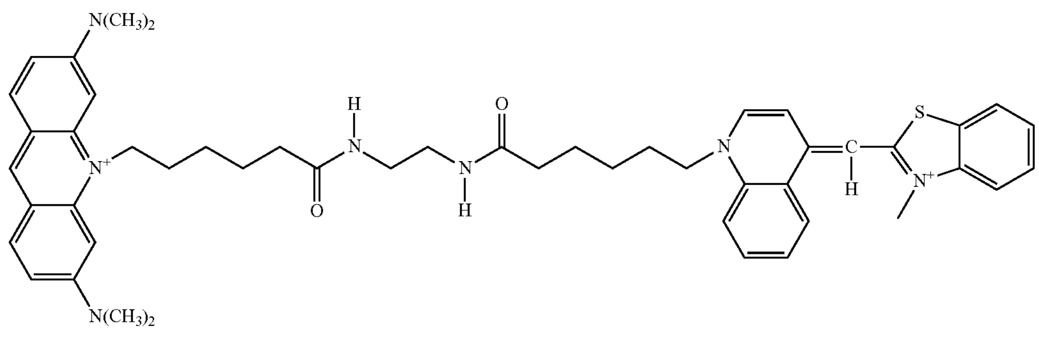 [SMILES: CN(C)c1ccc2cc3ccc(N(C)C)cc3[n+](CCCCCC(=O)NCCNC(=O)CCCCCN3C=C/C(=C\c4sc5ccccc5[n+]4C)c4ccccc43)c2c1] | 1094.99 | 16 |
| 24 | TOTO-12 | 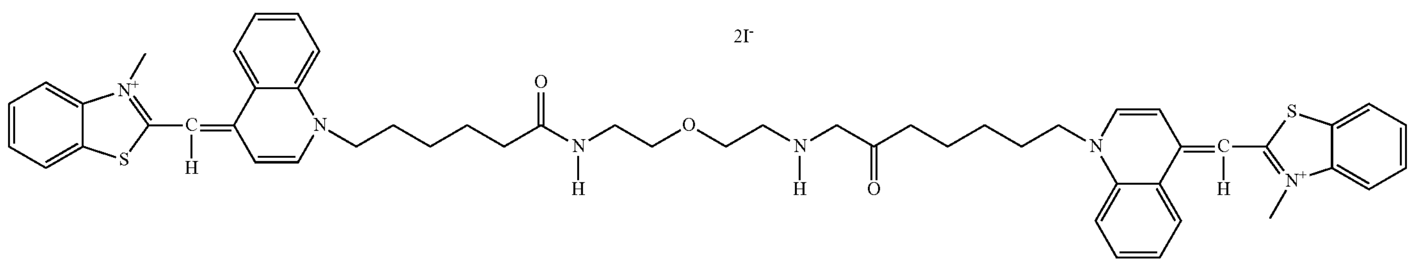 [SMILES: C[n+]1c(/C=C2/C=CN(CCCCCC(=O)NCCOCCNCC(=O)CCCCCN3C=C/C(=C\c4sc5ccccc5[n+]4C)c4ccccc43)c3ccccc32)sc2ccccc21] | 1146.23 | 20 |

TABLE 1-continued

Prepared Fluorescent Nucleic Acid Dyes

| No. | Name | Structure | MWt. | SPACER LENGTH (ATOMS) |
|---|---|---|---|---|
| 25 | TO(3)TO(3)-12 | 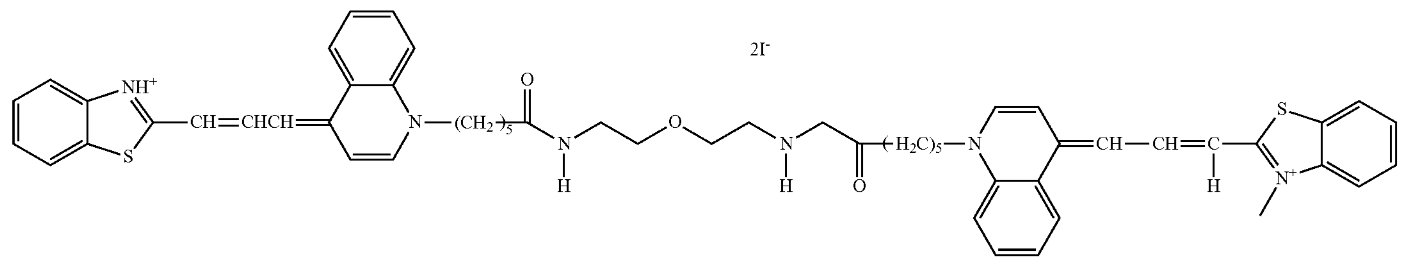 | 1245.34 | 20 |
| 26 | TO(3)TO(3)-2 | 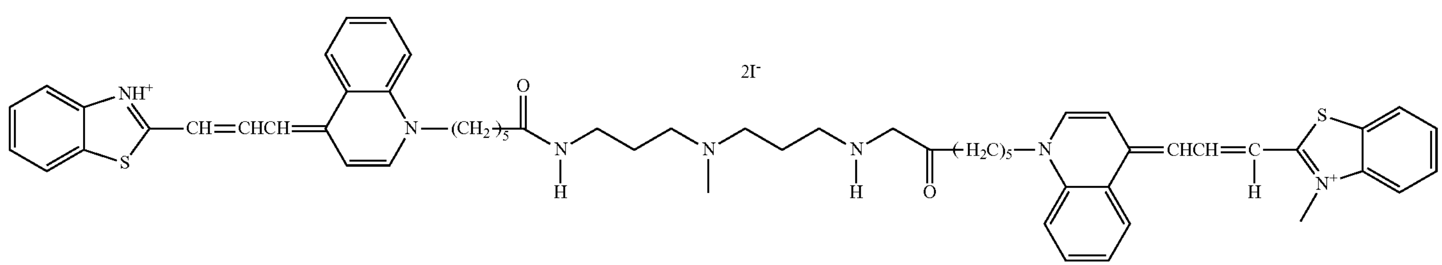 | 1302.44 | 22 |

TABLE 1-continued

Prepared Fluorescent Nucleic Acid Dyes

| No. | Name | Structure | MWt. | SPACER LENGTH (ATOMS) |
|---|---|---|---|---|
| 27 | AORO-7 | (structure shown) | 1320.25 | 21 |
| 28 | RORO-12 | (structure shown) | 1550.51 | 22 |

TABLE 1-continued
Prepared Fluorescent Nucleic Acid Dyes
| No. | Name | Structure | MWt. | SPACER LENGTH (ATOMS) |
|---|---|---|---|---|
| 29 | TOTO-13 | 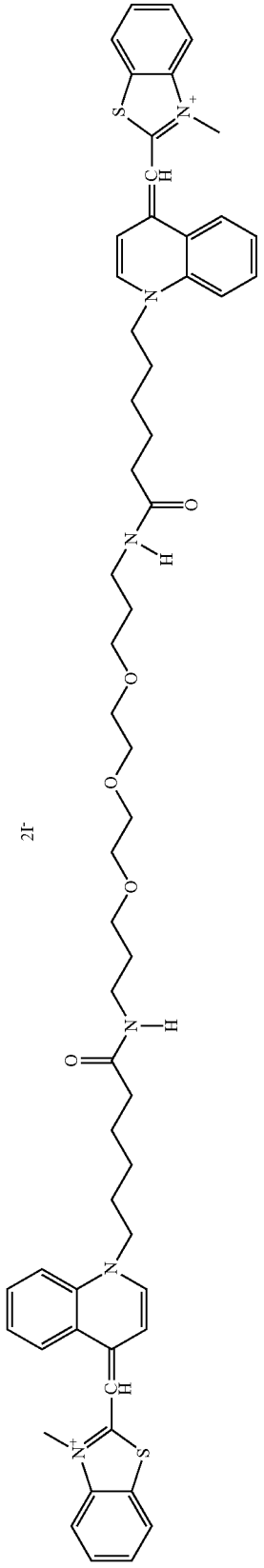 | 1248 | 27 |
| 30 | STST-27 | 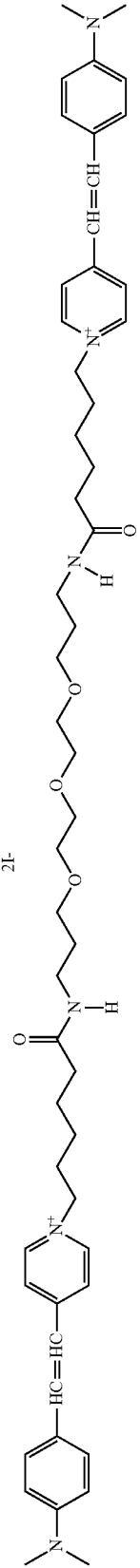 | 1116 | 27 |

TABLE 1-continued
Prepared Fluorescent Nucleic Acid Dyes
| No. | Name | Structure | MWt. | SPACER LENGTH (ATOMS) |
|---|---|---|---|---|
| 31 | STST-19 | 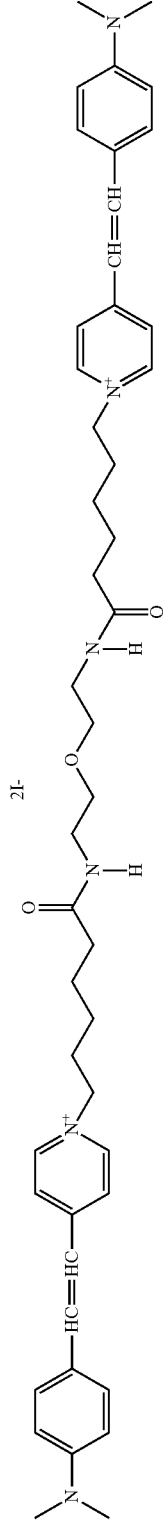 | 1000.8 | 19 |
| 32 | AOAO-47 | 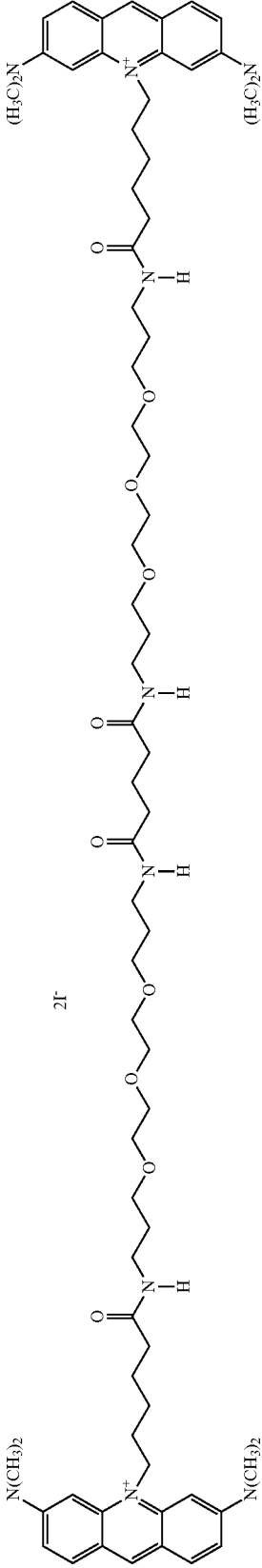 | 1547.6 | 47 |

TABLE 1-continued
Prepared Fluorescent Nucleic Acid Dyes
| No. | Name | Structure | MWt. | SPACER LENGTH (ATOMS) |
|---|---|---|---|---|
| 33 | AOAO-67 | 2r 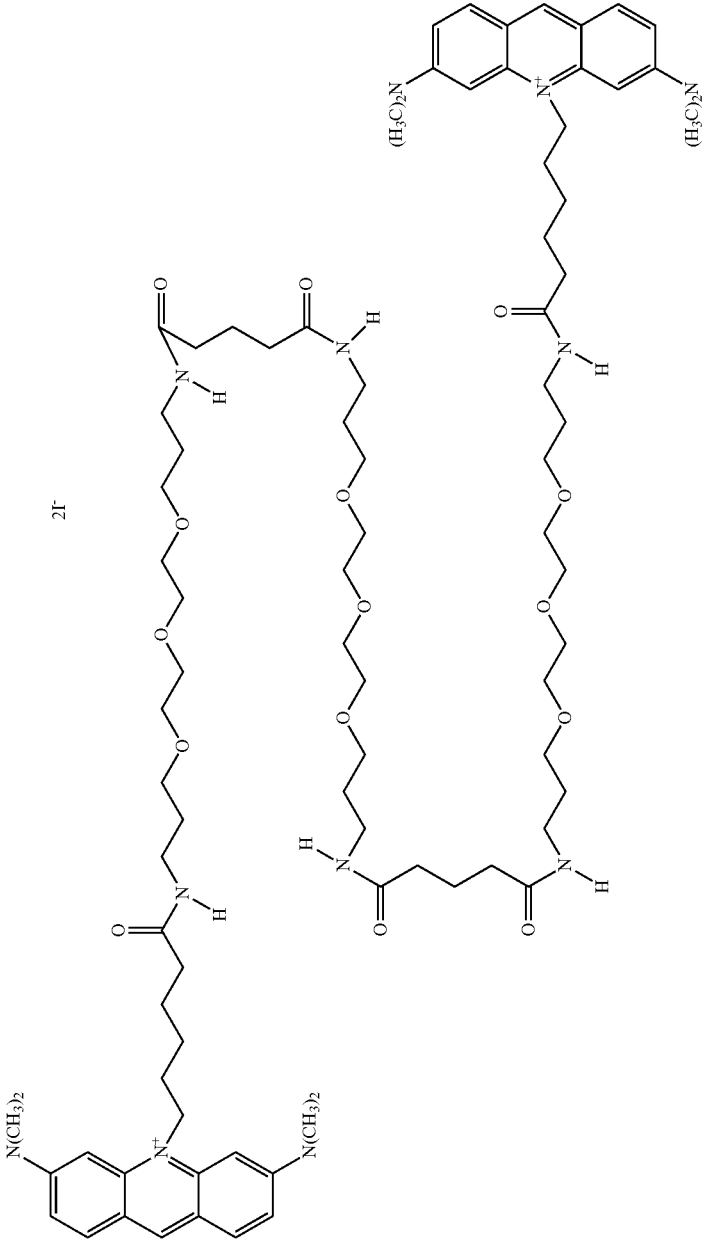 | 1864 | 67 |

TABLE 1-continued

Prepared Fluorescent Nucleic Acid Dyes

| No. | Name | Structure | MWt. | SPACER LENGTH (ATOMS) |
|---|---|---|---|---|
| 34 | AOAO-113 | 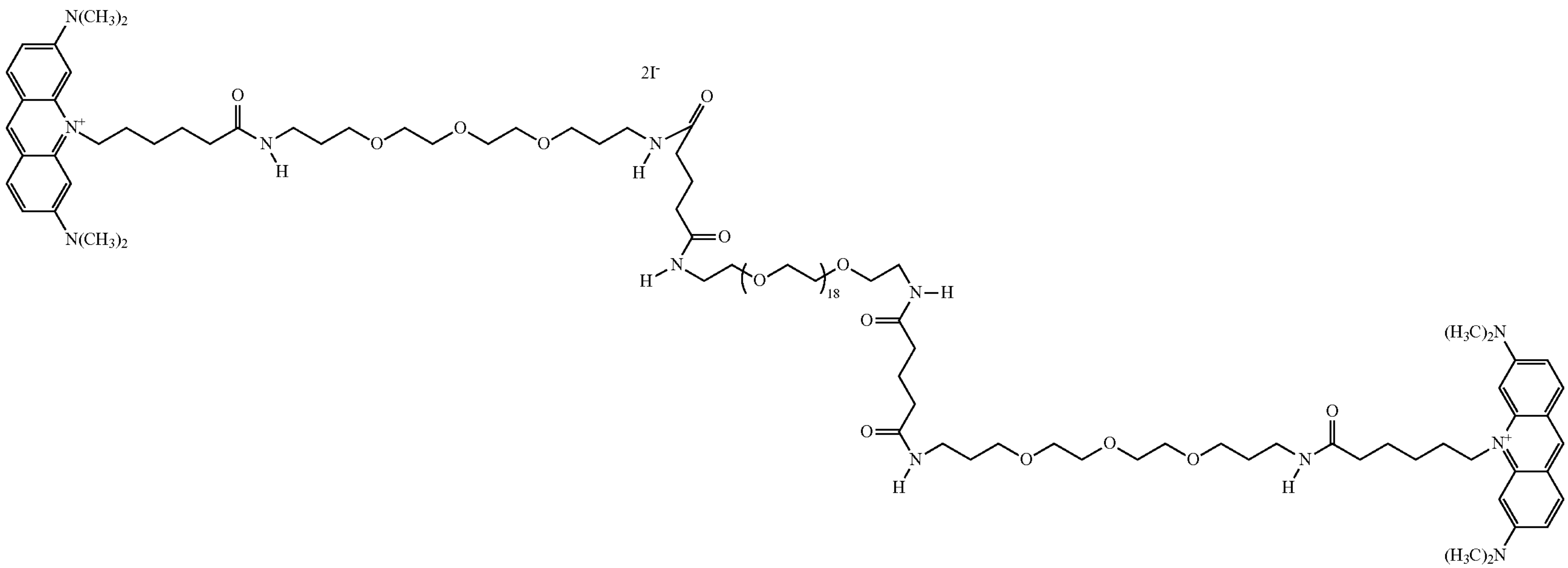 | 2541 | 113 |

TABLE 1-continued
Prepared Fluorescent Nucleic Acid Dyes
| No. | Name | Structure | MWt. | SPACER LENGTH (ATOMS) |
|---|---|---|---|---|
| 35 | ET-27 | 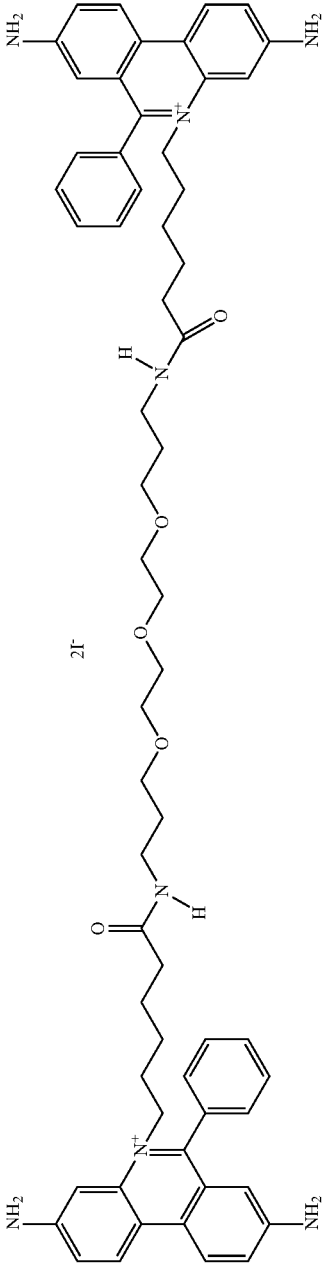 | 1239 | 27 |
| 36 | STST-21N | 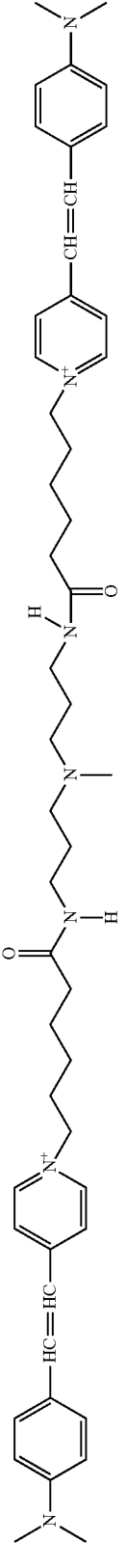 | 1041 | 21 |

While many of the structures shown in Table 1 show one or more iodide anion(s), any other appropriate anion(s), such as those described herein, such as chloride anion(s), merely by way of example, may be used in place of the iodide anions shown.

A dimeric dye may comprise a fluorescent nucleic acid dye $Q_1$ and a fluorescent nucleic acid dye $Q_2$, wherein $Q_1$ and $Q_2$ may be the same, or different. A dimeric dye may comprise a pair of identical fluorescent monomeric nucleic acid dyes. When $Q_1$ and $Q_2$ are the same, the resulting dye is a homodimer, such as any of Dye Nos. 6-22, 24-26, and 28-36 of Table 1, merely by way of example. When $Q_1$ and $Q_2$ are different fluorescent nucleic acid dyes that have similar absorption and emission spectra, the resulting dimer is a heterodimer, such as that of Dye No. 23 of Table 1, merely by way of example. Such a heterodimer is functionally similar to a homodimer. In either of the foregoing cases, both $Q_1$ and $Q_2$ are reporter dyes, such that upon DNA binding, they both contribute to the detected fluorescent signal. When $Q_1$ and $Q_2$ are different fluorescent nucleic acid dyes that have substantially different absorption and emission spectra, the resulting dimer is a heterodimer. In this latter case, only one of the two dyes, $Q_1$ and $Q_2$, is selected as a reporter dye.

Fluorescent nucleic acid dyes and examples thereof are now described. Examples of a monomeric fluorescent nucleic acid dye suitable for constructing dimeric dyes include, but are not limited to, an acridine dye, an asymmetric cyanine-based nucleic acid stain, a phenanthridinium dye, a symmetric cyanine nucleic stain, a pyronin dye, a styryl dye, a derivative of DAPI, and a derivative of a Hoechst dye. DAPI and Hoechst dyes generally cannot be directly attached to BRIDGE because they do not possess a reactive group for bond formation. In this context, a derivative refers to a base dye, such as DAPI or a Hoechst dye, that is modified sufficiently for bond formation, such as by addition of a reactive group, by way of example.

The monomeric fluorescent nucleic acid dye may be an acridine dye having the general structure (Structure 2) set forth directly below.

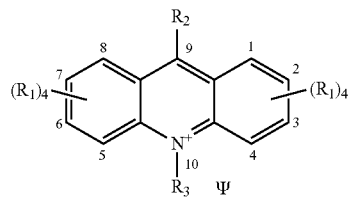

Structure 2

Acridine orange (AO) is an acridine dye that stains dsDNA with green fluorescence and stains RNA with red fluorescence. Traganos, et al., *J. Histochem. Cytochem.* 25(1), 46 (1977). Unlike some other acridine dyes, AO has a high extinction coefficient (>50,000) and a long absorption wavelength ($\lambda_{abs}$=500 nm (DNA bound)). However, the affinity of AO for nucleic acid is very low and the dye has significant intrinsic fluorescence in the absence of nucleic acids. In this regard, the level of intrinsic fluorescence may be significant in that it precludes the dye from being used in detecting nucleic acid at a low level, such as in the low nanogram/mL range, for example, or in detecting nucleic acid in gels without a destaining step, for example. Consequently, AO itself is of little utility for DNA or RNA quantification.

An acridine dye may comprise any of a variety of substituents at various positions on the ring structure. The nature of a substituent and its substitution position may strongly affect the spectral properties of the dye produced. In general, electron-donating substituents at the 3- and 6-positions and an electron-withdrawing substituent at the 9-position typically red-shift the absorption and emission spectra of the dye. Examples of a typical electron-donating group include, but are not limited to, an amino group, a hydroxyl group, an alkoxy group, and an alkylmercapto group. Examples of a typical electron-withdrawing group include, but are not limited to, a cyano group, a perfluoroalkyl group, a carboxamido group, a sulfonamide group, a nitro group, and a halogen group. Any additional ring structure fused with the core structure will also increase the wavelengths of the dye produced.

Various portions of Structure 2 are now described. In Structure 2, as in various other monomeric dye structures provided or described herein, a symbol of "R" followed by a subscript, such as $R_1$, merely by way of example, may indicate a substituent of the structure that is not part of BRIDGE, or may represent where BRIDGE attaches to the structure, in which case, it is not a substituent of the structure. Each $R_1$, independently, may be H; an alkyl or alkenyl having 1 carbon to 6 carbons, inclusive; a halogen; —$OR_4$; —$SR_5$; —$NR_6R_7$; —CN; —NH(C=O)$R_8$; —NHS(=O)$_2R_9$; or —C(=O)NHR$_{10}$; and any adjacent pair of $R_1$s optionally form a 5- or 6-membered saturated or unsaturated ring, which further optionally comprises at least one hetero atom selected from N, O and S. One of the $R_1$s may represent where BRIDGE attaches to the structure, in which case, that $R_1$ is merely representative and not actually a substituent of the monomeric dye. In any case where $R_1$ involves at least one of $R_4$, $R_5$, $R_6$, $R_7$, $R_8$, $R_9$, and $R_{10}$, any applicable one of same is independently H or an alkyl having 1 carbon to 6 carbons, inclusive, and for any applicable pair of adjacent $R_6$ and $R_7$, independently, $R_6$ and $R_7$ may in combination form a 5- or 6-membered saturated or unsaturated ring, which optionally comprises at least one hetero atom selected from N and O.

Typically, $R_2$ is H; an alkyl or alkenyl having 1 carbon to 6 carbons, inclusive; an aryl optionally comprising at least one hetero atom selected from halogens, N, O and S; a halogen; —$OR_{11}$; —$SR_{12}$; —$NHR_{13}$; —CN; or —C(=O)NHR$_{14}$; or represents where BRIDGE attaches to the structure. In any case where $R_2$ involves at least one of $R_{11}$, $R_{12}$, $R_{13}$ and $R_{14}$, any applicable one of same is independently H or alkyl having 1 carbon to 6 carbons, inclusive.

Typically, $R_3$ is H; or an alkyl having 1 carbon to 6 carbons, inclusive; or represents where BRIDGE attaches to the structure.

$\Psi$ is an anion, such as an anion that balances positive charge(s) associated with the dye, for example. $\Psi$ may be biologically compatible. Examples of a suitable anion include, but are not limited to, a halide, a sulfate, a phosphate, a perchlorate, a tetrafluoroborate, and a hexafluorophosphate. Merely by way of example, the anion may be chloride or iodide.

Only one of $R_1$, $R_2$ and $R_3$ must represent where BRIDGE attaches to the structure. Merely by way of example, one of $R_2$ and $R_3$ may represent where BRIDGE attaches to the structure. As described herein, BRIDGE may be covalently linked to a monomeric acridine dye, such as any such dye described herein, and to another suitable monomeric dye, to form a dimeric dye.

The monomeric acridine dye may have the structure (Structure 3) set forth directly below.

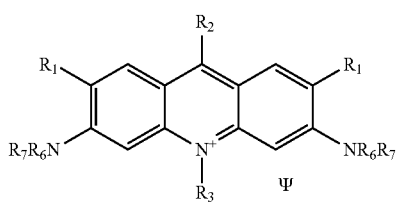

Structure 3

In Structure 3, generally, each $R_1$, independently, is H, or a C1-C2, inclusive, alkyl; one of $R_2$ and $R_3$ represents where BRIDGE attaches to the structure; when $R_2$ represents where BRIDGE attaches to the structure, $R_3$ is H or —$CH_3$; when $R_3$ represents where BRIDGE attaches to the structure, $R_2$ is selected from H, —$CH_3$, —$NH_2$, —$NHCH_3$, —CN, and —C(=O)$NH_2$; each of $R_6$ and $R_7$, independently, is H, or a C1-C2, inclusive, alkyl; and Ψ is an anion, as previously described. Merely by way of example, for each pair of adjacent $R_6$ or $R_7$ and $R_1$, independently, $R_6$ or $R_7$ and $R_1$ may in combination form a 5- or 6-membered, saturated or unsaturated ring. Further, merely by way of example, two monomeric acridine dye molecules of Structure 3 in combination with BRIDGE of Formula 2 may form a dimeric dye.

In one example, the monomeric acridine dye, as represented by Structure 3, may be such that each $R_1$ is H; $R_2$ is H; $R_3$ represents where BRIDGE attaches to the structure; each $R_6$ is —$CH_3$; each $R_7$ is —$CH_3$; and Ψ is an anion, as previously described.

A dimeric dye, such as a dimeric acridine dye, for example, may be useful for detecting nucleic acids immobilized relative to a matrix, such as a solid matrix, a semi-solid matrix, or a gel matrix, for example, or a surface, such as a solid surface, a membrane surface, a glass surface, a plastic surface, or a polysilicon surface, for example. A dimeric acridine dye may be useful for nucleic acid gel staining, such as pre-cast nucleic acid gel staining or post-nucleic acid gel staining. In such an application, there is no need for a de-staining step. In general, nucleic acid gel staining using a dimeric acridine dye is associated with relatively high sensitivity and relatively low background fluorescence. In this regard, sensitivity generally refers to an ability to detect a low level of nucleic acids, as shown by the number and brightness of bands appearing on the right-side lanes of the gel, such as the gel of Photograph C of FIG. 8, for example, and an ability to detect short nucleic acid fragments, as shown by the number and relative brightness of the bands appearing on the lower portion of the gel of Photograph C of FIG. 8, for example; and low background fluorescence generally refers to an ability to detect nucleic acid presence without having to destain the gel.

In an example (Example 50), each of three separate dyes, SYBR Safe, SYBR Green I, and Dye No. 20 of Table 1, a dimeric acridine dye, was prepared and used in post-DNA gel staining. Three separate photographs associated with the use of the three separate dyes, respectively, are shown in FIG. 8. These photographs demonstrate that Dye No. 20 is substantially more sensitive than SYBR Safe and is about as sensitive as SYBR Green I. However, SYBR Green I is known to be hydrolytically unstable in aqueous solution, and particularly, in buffers having a pH of 7 or more. Karsai et al., *Biotechniques* 32(4), 790 (2002). Dye No. 20 is relatively stable in water or in buffers that are commonly used in connection gel electrophoresis, at room temperature for about 3 months or more.

The monomeric fluorescent nucleic acid dye may be an asymmetric cyanine dye having the general structure (Structure 4) set forth directly below.

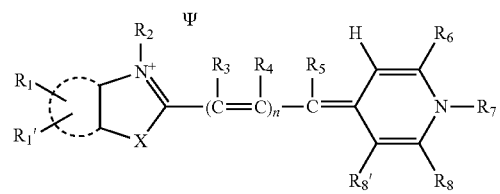

Structure 4

The general structure (Structure 4, above) of an asymmetric cyanine dye may be divided into three parts: 1) a heterocyclic ring that is a substituted benzazolium ring; 2) a methane or polymethine bridge; and 3) a heterocyclic ring that is a substituted pyridinium or quinolinium ring. The dotted line in the structure represents the atoms necessary to form one or more fused aromatic ring(s), optionally incorporating one or more nitrogen(s), which may or may not be quaternized. When the dotted line represents a 6-membered ring comprising one or more nitrogen atom(s), the resulting fused ring is called an aza-benzole ring.

In Structure 4, in general, each of $R_1$ and $R_1'$ on the benzazolium ring, independently, is H; alkyl or alkenyl having 1 carbon to 6 carbons, inclusive; a halogen; —$OR_9$; —$SR_{10}$; —$NR_{11}R_{12}$; —CN; —NH(C=O)$R_{13}$; —NHS(=O)$_2R_{14}$; or —C(=O)$NHR_{15}$. Merely by way of example, one of $R_1$ and $R_1'$ may be a substituent that is meta to X or to the benzazole nitrogen, wherein the substituent confers at least one desirable property as further described below. In any case where $R_1$ or $R_1'$ involves at least one of $R_9$, $R_{10}$, $R_{11}$, $R_{12}$, $R_{13}$, $R_{14}$ and $R_{15}$, any applicable one of same, independently, is H; or alkyl having 1 carbon to 12 carbons, inclusive, optionally incorporating 1 to 2 nitrogen(s), inclusive; or an aryl; and any applicable $R_{11}$ and $R_{12}$ may in combination form a 5- or 6-membered saturated or unsaturated ring, which optionally comprises at least one hetero atom selected from N and O.

As mentioned above, one of $R_1$ and $R_1'$ of Structure 4 may be a substituent that confers at least one desirable property to the dye. One such desirable property is DNA minor groove-binding. A minor groove-binding molecule typically has a structure with a crescent shape that fits into the minor groove of a double-stranded DNA. Examples of a DNA minor groove-binding dye molecule or non-dye molecule, which may include a natural molecule, include, but are not limited to, DAPI, a Hoechst dye, distamycin A, netropsin, and any of numerous synthetic minor groove-binders based on polyamides of N-methylpyrrole and N-methylimidazole. Catalog of Biotium, Inc. (Hayward, Calif. (CA)), 2005-2006; Boger, et al., *Acc. Chem. Res.* 37, 61 (2004); and Dervan, P. B., *Bioorg. & Med. Chem.* 9, 2215 (2001). The crescent shape of a minor groove-binder is typically created by meta-substitution of a 5- or 6-membered ring with a minor groove-binder substituent, which includes, but is not limited to, a substituted or an unsubstituted benzoxazol-2-yl, a substituted or an unsubstituted benzimidazol-2-yl, a substituted or an unsubstituted benzothiazol-2-yl, a substituted or an unsubstituted imidazol-2-yl, a substituted or an unsubstituted oxazol-2-yl, a substituted or an unsubstituted thiazol-2-yl, a substituted or an unsubstituted N-methylpyrrolyl-2-aminocarbonyl, a substituted or an unsubstituted N-methylpyrrolyl-3-carboxamido, a substituted or an unsubstituted 1-methylimidazol-2-carboxamido, a substituted or an unsubstituted 1-methylimidazol-4-aminocarbonyl, a substituted or an unsubstituted phenyl, a substituted or an unsubstituted pyridyl, a substituted or an unsubstituted pyrazinyl, and a substituted or an unsubstituted triazinyl. A DNA dye may be meta-substituted by a minor groove-binder substituent as described in U.S. Patent Application Publication No. 2004/0132046.

One of $R_1$ and $R_1'$ may represent where BRIDGE attaches to the structure.

X is selected from O and S. In general, a dye wherein X is S has longer absorption and emission wavelengths than a similar dye wherein X is O.

$R_2$ may be methyl or ethyl, or may represent wherein BRIDGE attaches to the structure. Merely by way of example, $R_2$ may be methyl or ethyl.

The subscript n represents a number of double bond units in any methine bridge and is selected from 0, 1, and 2. Typically, a dye with a longer methine bridge will have longer wavelengths than a dye with a shorter methine bridge. Merely by way of example, n may be 0 or 1.

Substitutents $R_3$, $R_4$, and $R_5$ are independently H or —$CH_3$. Optionally, any adjacent pair of these substitutents may form a 5- or 6-membered ring. Merely by way of example, $R_3$, $R_4$, and $R_5$ may be H.

Independently, each of substituents $R_6$, $R_8$, and $R_8'$ may be H; an alkyl or alkenyl having 1 carbon to 10 carbons, inclusive, optionally comprising at least one hetero atom selected from N, O, and S; a halogen; —$OR_{16}$; —$SR_{16}$; —$NR_{16}R_{17}$; or a substituted or unsubstituted aryl, optionally comprising 1 to 3 hetero atom(s), inclusive, selected from halogens, N, O, and S. $R_8$ and $R_8'$ may in combination form a fused aromatic ring, which may be further substituted 1 to 4 time(s), inclusive, independently, by C1-C2, inclusive, alkyl, C1-C2, inclusive, alkoxy, C1-C2, inclusive, alkylmercapto, or a halogen. In any case in which any of $R_6$, $R_8$, and $R_8'$ involve at least one of $R_{16}$ and $R_{17}$, any applicable one of same, independently, is H; or alkyl having 1 carbon to 12 carbons, inclusive, optionally incorporating 1 to 2 nitrogen(s), inclusive; or an aryl; and any applicable $R_{16}$ and $R_{17}$ may in combination form a 5- or 6-membered saturated or unsaturated ring, which optionally comprises at least one hetero atom selected from N and O.

$R_6$ may represent where BRIDGE attaches to the structure.

$R_7$ is selected from H; an alkyl or alkenyl having 1 carbon to 10 carbons, inclusive, optionally comprising an aryl and at least one hetero atom selected from N, O, and S; or a substituted or unsubstituted aryl optionally comprising 1 to 3 hetero atom(s), inclusive, selected from halogens, N, O, and S; or may represent where BRIDGE attaches to the structure.

Ψ is an anion, as previously described herein.

Only one of $R_1$, $R_1'$, $R_6$, $R_7$ and $R_8$ must represent where BRIDGE attaches to the structure. As described herein, BRIDGE may be covalently linked to a monomeric asymmetric cyanine dye, such as any such dye described herein, and to another suitable monomeric dye, to form a dimeric dye.

An asymmetric cyanine dye may have the structure (Structure 5) set forth directly below, wherein each of $R_1'$, $R_6$, $R_7$, $R_8$ and $R_8'$ is as previously described in connection with Structure 4.

—$NHS(=O)_2R_{14}$; —$C(=O)NHR_{15}$; or a substituent associated with minor groove binding; or represents where BRIDGE attaches to the structure. Further, when $R_1'$ comprises at least one of $R_9$, $R_{10}$, $R_{11}$, $R_{12}$, $R_{13}$, $R_{14}$ and $R_{15}$, any said one of $R_9$, $R_{10}$, $R_{11}$, $R_{12}$, $R_{13}$, $R_{14}$ and $R_{15}$, independently, is H or alkyl having 1 carbon to 12 carbons, inclusive, optionally incorporating 1 to 2 nitrogen(s), inclusive, or an aryl; and when $R_1'$ comprises $R_{11}$ and $R_{12}$, $R_{11}$ and $R_{12}$ may in combination form a 5- or 6-membered, saturated or unsaturated ring, which optionally comprises at least one hetero atom selected from N and O. X may be selected from O and S and n may be selected from 0, 1, and 2. $R_6$ may be H; alkyl or alkenyl having 1 carbon to 10 carbons, inclusive, optionally comprising at least one hetero atom selected from N, O, and S; a halogen; —$OR_{16}$; —$SR_{16}$; —$NR_{16}R_{17}$; or a substituted or an unsubstituted aryl, optionally comprising 1 to 3 hetero atom(s), inclusive, selected from halogens, N, O, and S; or may represent where BRIDGE attaches to the structure. $R_7$ may be H; alkyl or alkenyl having 1 carbon to 10 carbons, inclusive, optionally comprising an aryl and at least one hetero atom selected from N, O, and S; or a substituted or an unsubstituted aryl optionally comprising 1 to 3 hetero atom(s), inclusive, selected from halogens, N, O, and S; or may represent where BRIDGE attaches to the structure. $R_8$ may be H; alkyl or alkenyl having 1 carbon to 10 carbons, inclusive, optionally comprising at least one hetero atom selected from N, O, and S; a halogen; —$OR_{16}$; —$SR_{16}$; —$NR_{16}R_{17}$; or a substituted or an unsubstituted aryl, optionally comprising 1 to 3 hetero atom(s), inclusive, selected from halogens, N, O, and S; or may represent where BRIDGE attaches to the structure. $R_8'$ may be H; alkyl or alkenyl having 1 carbon to 10 carbons, inclusive, optionally comprising at least one hetero atom selected from N, O, and S; a halogen; —$OR_{16}$; —$SR_{16}$; —$NR_{16}R_{17}$; or a substituted or an unsubstituted aryl, optionally comprising 1 to 3 hetero atom(s), inclusive, selected from halogens, N, O, and S. $R_8$ and $R_8'$ may in combination form a fused aromatic ring, which may be further substituted 1 to 4 time(s), inclusive, independently, by C1-C2, inclusive, alkyl, C1-C2, inclusive, alkoxy, C1-C2, inclusive, alkylmercapto, or a halogen. For any $R_6$, $R_8$, or $R_8'$ that comprises at least one of $R_{16}$ and $R_{17}$, any said one of $R_{16}$ and $R_{17}$ thereof, independently, may be H; alkyl having 1 carbon to 12 carbons, inclusive, optionally incorporating 1 to 2 nitrogen(s) or an aryl. For any $R_6$, $R_8$, and $R_8'$ that comprises $R_{16}$ and $R_{17}$, $R_{16}$ and $R_{17}$ thereof may in combination form a 5- or 6-membered saturated or unsaturated ring, which optionally comprises at least one hetero atom selected from N and O. Only one of $R_1'$, $R_6$, $R_7$ and $R_8$ represents where BRIDGE attaches to the structure. Ψ is an anion, as previously described.

An asymmetric cyanine dye may have the structure (Structure 6) set forth directly below, wherein $R_7$ represents where BRIDGE attaches to the structure and Ψ is an anion, as previously described.

Structure 5

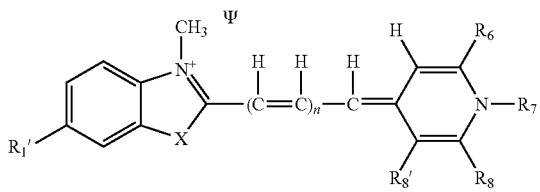

Structure 6

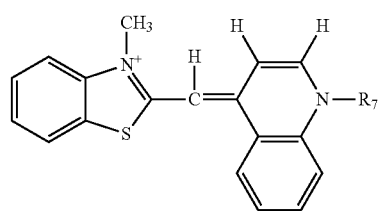

By way of example, the asymmetric cyanine dye, as represented by Structure 5, may be such that $R_1'$ is H; alkyl or alkenyl having 1 carbon to 6 carbons, inclusive; a halogen; —$OR_9$; —$SR_{10}$; —$NR_{11}R_{12}$; —CN; —NH(C=O)$R_{13}$;

Merely by way of example, two monomeric asymmetric cyanine dye molecules of Structure 6 in combination with BRIDGE of Formula 2 may form a dimeric dye.

A dimeric asymmetric cyanine dye may be useful for detecting nucleic acids immobilized relative to a matrix or a surface, as previously described in connection with another dye, or the like, and for nucleic acid gel staining, such as pre-cast nucleic acid gel staining or post nucleic acid gel staining. In general, nucleic acid gel staining using a dimeric cyanine dye is associated with high sensitivity and low background fluorescence. In such an application, there is no need for a de-staining step. In an example (Example 50) described herein, each of three separate dyes, SYBR Safe, SYBR Green I, and Dye No. 29 of Table 1, a dimeric asymmetric cyanine dye, was prepared and used in post-DNA gel staining. Three separate photographs associated with the use of the three separate dyes, respectively, are shown in FIG. 9. These photographs demonstrate that Dye No. 29 is substantially more sensitive than SYBR Safe and is as sensitive as SYBR Green I. In this regard, sensitivity generally refers an ability to detect low levels of nucleic acids and/or short nucleic acid fragments, as previously described herein. Unlike SYBR Green 1, Dye No. 20 of Table 1 is relatively stable is in buffers that are commonly used in connection gel electrophoresis, such as TBE, at room temperature for about 3 months or more.

A dimeric asymmetric cyanine dye comprising monomeric asymmetric cyanine dyes of Structure 6 may be excited by UV light or by visible light, such as the blue light equipped in a Dark Reader transilluminator from Clare Chemical Research (Dolores, Colo.) and a 488 nm argon laser equipped in some of the commercial laser-based gel scanners, for example. In an example (Example 50) described herein, Dye No. 29 of Table 1 was prepared and used in post-DNA gel staining A photograph of associated with the use of Dye No. 29 is shown in FIG. 11. Relatively new gel readers, such as the Dark Reader transilluminator, which use a visible light source, have been developed as a safer alternative to traditional UV light-based transilluminators. These alternative gel readers may employ a blue light with a peak centered around 470 nm. There are also gel readers that use light from 488 nm argon lasers. A gel stain must absorb light sufficiently within a wavelength range of 460-510 nm, inclusive, in order to be read using the various visible light-based gel readers. As such, a gel stained with EB cannot be read using a visible light-based gel reader because the absorption peak of EB is not within the appropriate wavelength range. Dye No. 29 of Table 1 has a very strong and broad absorption or excitation peak centered around 500 nm, as demonstrated in relation to Example 51 and graphically shown in FIG. 10, such that a gel stained with this dye can be read using a visible light-based gel reader, as demonstrated in relation to Example 50 and shown in FIG. 11.

The monomeric fluorescent nucleic acid dye may be a phenanthridinium derivative, having the general structure (Structure 7) set forth directly below.

Structure 7

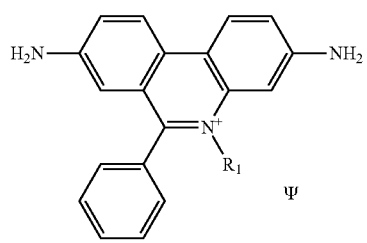

In general, $R_1$ may represent where BRIDGE attaches to the structure, although it will be understood that many variations of Structure 7 above are possible and contemplated herein, via a variety of techniques, such as synthesis techniques that may provide for the attachment of BRIDGE to the structure elsewhere or that may modify the structure to provide a dye with any of various desirable wavelengths. Ψ is an anion, as previously described.

Merely by way of example, two monomeric phenanthridinium dye molecules of Structure 7 in combination with BRIDGE of Formula 2 may form a dimeric dye.

A dimeric phenanthridinium dye may be useful for detecting nucleic acids immobilized relative to a matrix or a surface, as previously described in relation to another dye, or the like, and for nucleic acid gel staining, such as pre-cast nucleic acid gel staining or post-nucleic acid gel staining. In general, nucleic acid gel staining using a dimeric phenanthridinium dye is associated with high sensitivity and low background fluorescence. In such an application, there is no need for a de-staining step. In an example (Example 49) described herein, each of two separate dyes, EB and Dye No. 35 of Table 1 (ET-27), a dimeric phenanthridinium dye, was prepared and used in pre-cast DNA gel staining Photographs associated with the use of the two dyes, respectively, are shown in FIG. 12.

A dimeric phenanthridinium dye may be relatively stable, even exceptionally so, relative to an SYBR dye, such as those mentioned herein, which may be relatively unstable. In an example (Example 52) described herein, each of two separate dyes, SYBR Gold and Dye No. 35 of Table 1 (ET-27), a dimeric phenanthridinium dye, was prepared and monitored in terms of optical density. A graphical representation of normalized absorbance versus time for each of the solutions is shown in FIG. 13. As shown, the absorbance associated with Dye No. 35 was relatively constant over the 24-hour period, while the absorbance of SYBR Gold decreased by nearly 50% over the same period. Dye No. 35 is generally stable in an electrophoresis buffer, such as TBE buffer, at room temperature for at least about 6 months. Further, this dye in TBE buffer may be heated in a microwave oven for at least about 10 minutes without decomposition.

In a gel electrophoresis application, an agarose gel may be prepared by heating (via microwave, for example) a suspension of agarose powder in an electrophoresis buffer, such as TBE buffer, thereby producing a hot agarose solution, pouring the solution onto a slab, and cooling the solution, thereby producing a useful gel. In a pre-cast gel staining application, an EB dye may be added directly to the agarose powder suspension prior to the heating of the suspension, as EB is generally sufficiently stable, both hydrolytically and thermally. This is generally not the case with a SYBR Green dye, as such a dye is generally of limited hydrolytic and thermal stability. For example, in a pre-cast gel staining application, SYBR Green I dye is generally combined with an agarose solution after the initial agarose suspension has been heated and the resulting agarose solution has been cooled as much as possible. Combining the SYBR Green I dye with the agarose solution in this manner may be a delicate task, as if the temperature of the agarose solution is too high, the dye my decompose, and if the temperature of the agarose solution is too low, the agarose solution may gel up such that the dye and the solution are inadequately combined or mixed. Further by way of example, in a pre-cast gel staining application, a pre-cast gel prepared with SYBR Green I is generally used within 24 hours, as it may lose utility thereafter. As SYBR Gold is even less stable than SYBR Green, it generally cannot be used to make a precast gel. Dye No. 35 of Table 1 is of sufficient hydrolytic and thermal stability to be used in the preparation of a pre-cast gel, such as a pre-cast gel that may be stored for at least about 3 months without loss of performance, for example. This dye may offer sufficient to exceptional stability, as well as low or minimal background fluorescence relative to EB and low or minimal toxicity relative to EB, as further described below.

Dye No. 35 of Table 1 is relatively low in toxicity and mutagenicity. A mutagenicity comparison was made between Dye No. 35 and EB using a ChromoPlate test kit from EBPI (Brampton, Ontario, Canada). The test kit is based on the Ames Test, a bacterial reverse mutation test. The test employs a mutant strain, or several strains, of *Salmonella typhimurium* bacteria, carrying mutation(s) in the operon coding for histidine biosynthesis. When the bacteria are exposed to mutagenic agents under certain conditions, reverse mutation from amino acid (histidine) auxotrophy to prototrophy occurs. In an example (Example 53) described herein, Dye No. 35 and EB were assayed using three dose levels (0.25 nmole, 2.5 nmoles and 25 nmoles), respectively, for each dye, and in the absence and presence of S9 extract for each dose level and each dye, respectively. S9 extract is a rat liver extract that comprises various metabolic enzymes. The tests associated with the presence of S9 extract were undertaken to give information on the potential genotoxicity of the metabolized dyes. Bacterium strain TA98, a frame shift indicator, was used for the tests (according to a protocol provided by the supplier) since EB is a known frame shift mutagen as shown by Ames Test using the same bacterial strain. Each single test was carried out using 36 wells and the number of positive wells out of each 36 wells was taken as an indicator of the relative mutagenicity levels of the dye under the test conditions. As a negative control, bacteria were also incubated in the absence of a dye. The results are shown in Table 2 below.

TABLE 2

Mutagenicity Data

Without S9 extract

| | Positive wells | |
|---|---|---|
| Sample | Exp 1 | Exp 2 |
| Control | 3 | 0 |
| EB (0.25 nmole) | 0 | 0 |
| EB (2.5 nmoles) | 0 | 3 |
| EB (25 nmoles) | 0 | 3 |
| Dye No. 35 (0.25 nmole) | 2 | 0 |
| Dye No. 35 (2.5 nmoles) | 1 | 3 |
| Dye No. 35 (25 nmoles) | 1 | 3 |

With S9 extract

| Sample | Positive wells |
|---|---|
| Control | 4 |
| EB (0.25 nmole) | 22 |
| EB (2.5 nmoles) | 17 |
| EB (25 nmoles) | 16 |
| Dye No. 35 (0.25 nmole) | 0 |
| Dye No. 35 (2.5 nmoles) | 9 |
| Dye No. 35 (25 nmoles) | 0 |

As shown in Table 2, relative to the negative control in which no dye was present, both Dye No. 35 and EB showed very weak mutagenicity in the absence of S9 extract. As also shown, EB showed significantly greater mutagenicity than Dye No. 35 in the presence of S9 extract. It is believed that the relatively low mutagenicity of Dye No. 35 may be attributable to a combination of factors, such as the high molecular weight of the dye, where the high molecular weight makes it difficult for the dye to enter cells, and the H-dimer formation property of the dye, where the H-dimer formation lowers the effective concentration of the dye.

The monomeric fluorescent nucleic acid dye may be a xanthene derivative, having the general structure (Structure 8) set forth directly below.

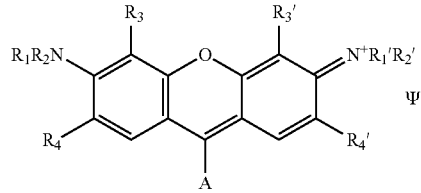

Structure 8

Certain cationically charged xanthene dyes are known to bind to nucleic acids. For example, pyronin Y, in which $R_1$, $R_2$, $R_1'$, and $R_2'$ are methyl and $R_3$, $R_3'$, $R_4$, $R_4'$, and A are H, is a known fluorescent DNA binding dye that has been used for DNA gel staining Adkin et al., *Anal. Biochem.* 240(1), 17 (1996). A dye having the general skeleton shown in Structure 8 above is expected to have similar nucleic acid staining properties and to provide other fluorescent colors. For example, pyronin Y has an absorption maximum at 548 nm and an emission maximum at 565 nm, providing a red fluorescent color.

Merely by way of example, in general, each of $R_1$, $R_2$, $R_1'$, and $R_2'$, independently, may be H, or C1-C6, inclusive, alkyl, optionally incorporating 1 to 2 hetero atom(s) selected from N and O. Further merely by way of example, independently, at least one of the pair $R_1$ and $R_2$ and the pair $R_1'$ and $R_2'$ may in combination form a 5- or 6-membered ring, optionally comprising one hetero atom selected from N and O. $R_1$ and $R_1'$ may be the same and $R_2$ and $R_2'$ may be the same.

One of $R_1$, $R_2$, $R_1'$, and $R_2'$ may represent where BRIDGE attaches to the structure. It may be that one of $R_1$, $R_2$, $R_1'$, $R_2'$ and A may represent where BRIDGE attaches to the structure.

Merely by way of example, $R_3$, $R_3'$, $R_4$, and $R_4'$, independently, may be H or C1-C3, inclusive, alkyl. $R_3$, $R_3'$, $R_4$, and $R_4'$ may be the same. Independently, at least one of the pair $R_3$ and $R_1$, the pair $R_2$ and $R_4$, the pair $R_3'$ and $R_1'$, and the pair $R_4$ and $R_2'$ may in combination form a 5- or 6-membered ring, which may be saturated or unsaturated, substituted or unsubstituted.

A is a C1-C3, inclusive, alkyl, or represents where BRIDGE attaches to the structure.

Ψ is an anion, as previously described.

Two monomeric xanthene dye molecules of Structure 8 in combination with BRIDGE of Formula 2 may form a dimeric dye.

Other monomeric fluorescent nuclei acid stains, such as DAPI, DIPI, a Hoechst dye, LDS 751, hydroxystilbamidine, a styryl dye, a merocyanine dye, a cyanine dye, or FluoroGold, merely by way of example, may be suitable for use or may be derivatized to be suitable for use as described herein. Haugland, R. P., *Handbook of Fluorescent Probes and Research Products*, 9th edition. It will be understood that a large number of other monomeric nucleic acid dyes may be suitable for use or may be derivatized to be suitable for use as described herein. The dyes may either be directly conjugated to BRIDGE or be derivatized so that they can be conjugated to BRIDGE using synthesis knowledge.

Dimeric nucleic acid dyes may be useful for detecting nucleic acids immobilized relative to a matrix or a surface, as previously described herein in connection with various dyes, or as nucleic acid gel stains.

There are generally two methods for staining nucleic acids in gels using a fluorescent nucleic acid dye. The first method is post-gel staining, wherein a nucleic acid sample is separated by gel electrophoresis, the gel comprising the separated nucleic acids is bathed in a solution comprising the dye, the gel may be destained, if desirable or necessary to remove background fluorescence, and the resulting gel is viewed and/or documented using a transilluminator and/or a photographing device. The second method is pre-cast gel staining, wherein a gel is premixed or pre-embedded with the dye, the nucleic acid sample is separated by electrophoresis using the pre-cast gel, and the stained gel is viewed and/or documented using a transilluminator and/or a photographing device. In general, a dimeric nucleic acid dye can be used for post-gel staining, pre-cast gel staining, or variations thereof. As such a dye is generally associated with low background fluorescence, destaining is usually not required.

Post-nucleic acid gel staining may be carried out using a dimeric nucleic acid dye. Generally, post-nucleic acid gel staining may comprise preparation of a gel, electrophoretic separation of a nucleic acid sample, preparation of a dye solution, staining of the gel comprising separated nucleic acid molecules, and/or visualization of the stained gel, as now generally described.

The gel may be prepared by a known method or any appropriate method. The gel may be an agarose gel, a polyacrylamide gel, or the like. In general, the density of a gel, which is determined by the amount of agarose or acylamide monomer per volume unit, affects DNA migration, and thus separation of DNA bands. By way of example, for suitable or optimal DNA band resolution, a gel with a relatively lower percentage of agarose, such as 0.3-0.7% (weight/volume), may be used for relatively longer DNA samples, such as DNA of 5-60 kb. Further by way of example, a gel with a relatively higher percentage of agarose, such as 1.5-3% (weight/volume), may be used for relatively shorter DNA fragments, such as DNA of 0.1 to 1 kb. In general, an agarose gel comprising about 1% of agarose may be used for separating DNA of relatively common lengths or sizes, such as from about 0.5 to about 6 kb.

A nucleic acid sample may be prepared, loaded onto a gel, and then separated by electrophoresis. The process may involve the preparation of a dye stock solution. A dye stock solution may be prepared by dissolving a solid dimeric dye in an aqueous solvent, such as water or a buffer or a water-miscible organic solvent, such as DMSO or DMF. In general, the concentration of the stock solution is about 100-fold to about 10,000-fold greater relative to the concentration of a working dye solution. The working dye solution may be prepared by diluting the dye stock solution to an effective dye concentration with an aqueous solvent selected from water; a solution of at least one salt that comprises an anion that is associated with a strong acid and a cation that is associated with a strong base, such as a salt previously described herein, for example; and a buffer selected from phosphate buffered saline (PBS), tris acetate (TAE), and tris borate (TBE); and any combination thereof. Merely by way of example, the dye stock solution may be so diluted in an aqueous solution comprising a salt that comprises an anion that is associated with a strong acid and a cation that is associated with a strong base. Examples of such a salt include, but are not limited to, sodium chloride, sodium bromide, sodium sulfate, potassium chloride, potassium bromide, potassium sulfate, magnesium chloride, and tetramethylammonium chloride. In such a case, the salt concentration may be from about 5 mM to about 0.5 M, inclusive, about 0.05 M to about 0.2 M, inclusive, or about 0.1 M. In general, an effective working concentration of the dye is from about 0.1 µM to about 100 µM, inclusive, or from about 0.5 µM to about 10 µM, inclusive.

The gel and the working dye solution may be placed in contact in an appropriate manner, such as by immersing the gel in the working dye solution for a sufficient amount of time, such as from about 10 to about 90 minutes, inclusive, or about 30 minutes. Once the gel is stained by the working dye solution, the stained gel may be illuminated with a light of suitable wavelength to generate a fluorescence signal. Equipment useful for illuminating a stained gel includes, but is not limited to, a UV transilluminator, a laser scanner, a Dark Reader from Clare Chemical Research, Inc. (Dolores, Colo.), or the like, merely by way of example. The fluorescence signal may be detected in any appropriate manner, such as via visual inspection, a camera, a photographic film, or the like, merely by way of example.

Pre-cast nucleic acid gel staining may be carried out using a dimeric nucleic acid dye. Generally, this pre-cast nucleic acid gel staining may comprise preparation and casting of a stained gel, electrophoretic separation of a nucleic acid sample, and/or visualization of the stained gel, as now generally described.

A gel solution comprising a dimeric dye may be prepared in various ways. A dye stock solution may be prepared as generally described above in relation to post-gel staining. In one example, a gel solution comprising a dimeric dye may be prepared by combining or mixing an aliquot of the dye stock solution with a suitable amount of agarose powder in an electrophoresis buffer, such as TBE buffer, and heating the resulting solution under conditions suitable for producing an approximately homogeneous gel solution, such as via a microwave oven, for example, at a suitable setting or temperature, for example, and for a sufficient amount of time, such as a few minutes, for example. In another example, a gel solution comprising a dimeric dye may be prepared by preparing an agarose gel solution as just described, but without the dye, and combining or mixing the resulting solution with an aliquot of the dye stock solution sufficient to provide an effective working concentration of the dye. In either example or any suitable preparation, the effective working concentration of the dye in the gel solution may generally be from about 0.1 µM to about 100 µM, inclusive, or from about 0.5 µM to about 10 µM, inclusive. Further, in either example or any suitable preparation, the amount of agarose in the gel solution may generally be from about 0.5% to about 8%, inclusive. Other gel solutions, such as gel solutions comprising a suitable component other than agarose, may be similarly prepared.

A gel may be cast using the heated gel solution. A nucleic acid sample may be prepared, loaded onto the gel, and then electrophoretically separated in a known manner or any appropriate manner. The gel comprising the separated nucleic acid sample may be illuminated in any appropriate manner to generate a fluorescence signal, which may then be detected or visualized in any appropriate manner, such as that generally described above in connection with post-gel staining.

Any suitable variation of the above-described nucleic acid detection schemes may be employed and is contemplated herein. Merely by way of example, a nucleic acid sample to be detected may be present and/or immobilized in a sieving matrix, in a sedimentation or buoyant density gradient, on an inert matrix such as a blot, on a testing strip, on any other solid or semi-solid support, or the like.

A post-gel staining solution may comprise an aqueous solution that comprises a nucleic acid stain and at least one salt that comprises an anion that is associated with a strong acid and a cation that is associated with a strong base. The concentration of the stain relative to the solution may be from about 0.1 µM to about 100 µM, inclusive, or from about 0.5 µM to about 10 µM, inclusive, for example. The stain or dye component may be any useful staining dye, such as a monomeric or dimeric nucleic acid dye, merely by way of example. The salt may have a concentration of from about 5 mM to about 0.5 M, inclusive, about 0.05 M to about 0.2 M, inclusive, or about 0.1 M, for example. The salt component may enhance, perhaps significantly so, the staining quality of a post-nucleic acid staining solution. The salt may be selected from the sodium chloride, sodium bromide, sodium sulfate, potassium chloride, potassium bromide, potassium sulfate, tetramethylammonium chloride, and/or magnesium chloride for example. The aqueous solution may further comprise, optionally, a buffer.

A post-gel staining solution comprising a salt that comprises an anion that is associated with a strong acid and a cation that is associated with a strong base provides better results in a nucleic acid gel-staining application than does a post-gel staining solution that comprises a buffer, but no such salt. This holds true when the post-gel staining solution comprises a dimeric nucleic acid dye, such as those described herein, or a monomeric nucleic acid dye, such as an asymmetric cyanine nucleic acid dye, such as SYBR Green I, SYBR Safe, SYBR Gold and GelStar, merely by way of example.

In an example (Example 49) described herein, each of two separate dyes, SYBR Green I and Dye No. 29 of Table 1, a dimeric asymmetric cyanine dye, was prepared and used in post-DNA gel staining. Three separate photographs (A, B and C) associated with the use of three separate and different preparations of the SYBR Green I dye, and three separate photographs (D, E and F) associated with the use of three separate and different preparations of Dye No. 29, respectively, as described in the brief description of FIG. 14 herein, are shown in FIG. 14. Photographs A and D are associated with dye preparations comprising a buffer, but no separate salt, and photographs B, C, E and F are associated with dye preparations comprising a salt, NaCl. These photographs demonstrate that gel staining solutions prepared with a salt comprising an anion that is associated with a strong acid and a cation that is associated with a strong base, such as NaCl, may provide superior nucleic acid staining results relative to gel staining solutions prepared with a buffer and without such a salt. For example, as shown in photographs B, C, E and F of FIG. 14, gels stained with a staining solution comprising NaCl were associated with relatively brighter DNA bands overall and with DNA bands of decreasing brightness from the first lane on the left (greater DNA loading) to the 4th lane on the right (lesser DNA loading), as expected. As shown in photograph A of FIG. 14, the gel stained with SYBR Green I staining solution that lacked NaCl was associated with relatively weaker or less bright DNA bands overall and with DNA bands that were relatively unreflective of the relative amount of DNA loaded in each lane, as shown by the more or less evenly weak signals in the left three lanes.

A dimeric nucleic acid dye may be included in a kit. A kit may comprise the dye, information or a protocol regarding use of the dye or the kit, and/or other useful or necessary materials or reagents, such as any materials or reagents suitable for the detection of nucleic acids, for example, such as a buffer, a DNA or RNA ladder, and/or agarose, for example. A kit may comprise the dye impregnated into paper, such as paper provided by Edvotek (Bethesda, Md.) or disclosed in European Patent Office Publication No. EP 1 057 001 A2 or World Intellectual Property Organization International Publication No. WO 99/42620.

A dimeric nucleic acid dye may be synthesized via synthesis of monomeric dye constituents, synthesis of BRIDGE, and conjugation of the monomeric dye constituents to BRIDGE. Syntheses of monomeric dyes and monomeric dyes comprising a functional group or a reactive group are now described.

Suitable monomeric dyes and monomeric dyes comprising a functional group or a reactive group may be prepared from scratch by a known procedure or any suitable procedure, or by modifying commercially available material that already has a suitable or desirable core structure. Many monomeric acridine dyes may be prepared from commercially available acridine dyes. A few examples of a commercially available acridine dye that may serve as suitable starting material for synthesis are set forth directly below.

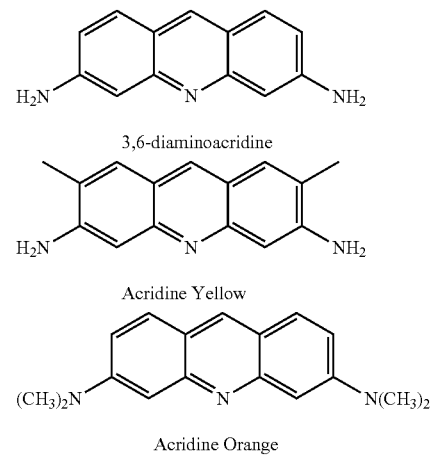

Other acridine core structures may be prepared according to known procedures or any suitable procedures. Albert, A., *The acridines: their preparation, physical, chemical, and biological properties and uses*, Edward Arnold Ltd., London; Eldho, et al., *Synth. Commun.* 29, 4007 (1999); and Joseph, et al., *Bioconjugate Chem.* 15, 1230 (2004). An acridine core structure may be formed by condensing a suitable diphenylamine with a suitable carboxylic acid or a carboxylic acid equivalent in the presence of a Lewis acid, as schematically illustrated in Reaction 1 directly below.

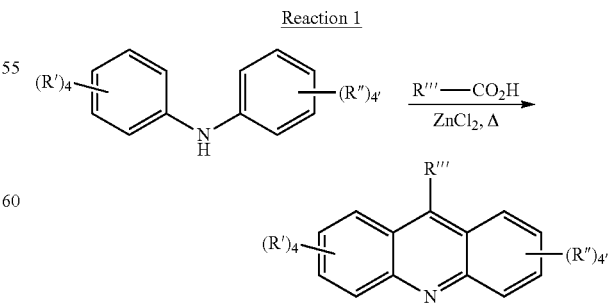

In Reaction 1, R', R" and R''' are suitable substituents, as further described below. The diphenylamine starting material is either commercially available or may be synthesized from a suitable arylhalide and a suitable arylamine using a known method or any suitable method. Yang, et al., *J. Organomet. Chem.* 576, 125 (1999); Hartwig, et al., *J. Org. Chem.* 64, 5575 (1999); and Wolfe, et al., *J. Org. Chem.* 65, 1158 (2000).

The nature of the substituents and the position where the substituents are attached may have a profound effect on the spectral property of the dye. In general, electron-donating groups at the 2-, 3-, 6- and 7-positions will increase the absorption and emission wavelengths of the dye. A typical electron-donating group may be an amino group, an alkylamino group, a dialkylamino group, a hydroxyl group, an alkoxy group, a thiol group, or an alkylthio group, by way of example. A more typical electron-donating group may be an amino group, an alkylamino group, a dialkylamino group, or an alkoxy group, by way of example. In general, an electron-withdrawing group at the 9-position will increase the absorption and emission wavelengths of the dye. A typical electron-withdrawing group may be a cyano group, a perfluoroalkyl group, an aminocarbonyl group, an alkylaminocarbonyl group, an alkylcarbonyl group, an aldehyde group, an alkoxycarbonyl group, an aminosulfonato group, an alkylaminosulfonato group, or a halide group, by way of example. A more typical electron-withdrawing group may be a cyano group, a perfluoroalkyl group, or a halide group.

In general, once the acridine core structure is built, the 10-nitrogen is alkylated with a haloalkyl group, which typically comprises an additional reactive group or a functional group that can be converted to a reactive group. The additional reactive group serves to conjugate the acridine dye to BRIDGE. Several ways of making monomeric acridine orange dyes with a suitable reactive group are schematically illustrated in Scheme 1 directly below.

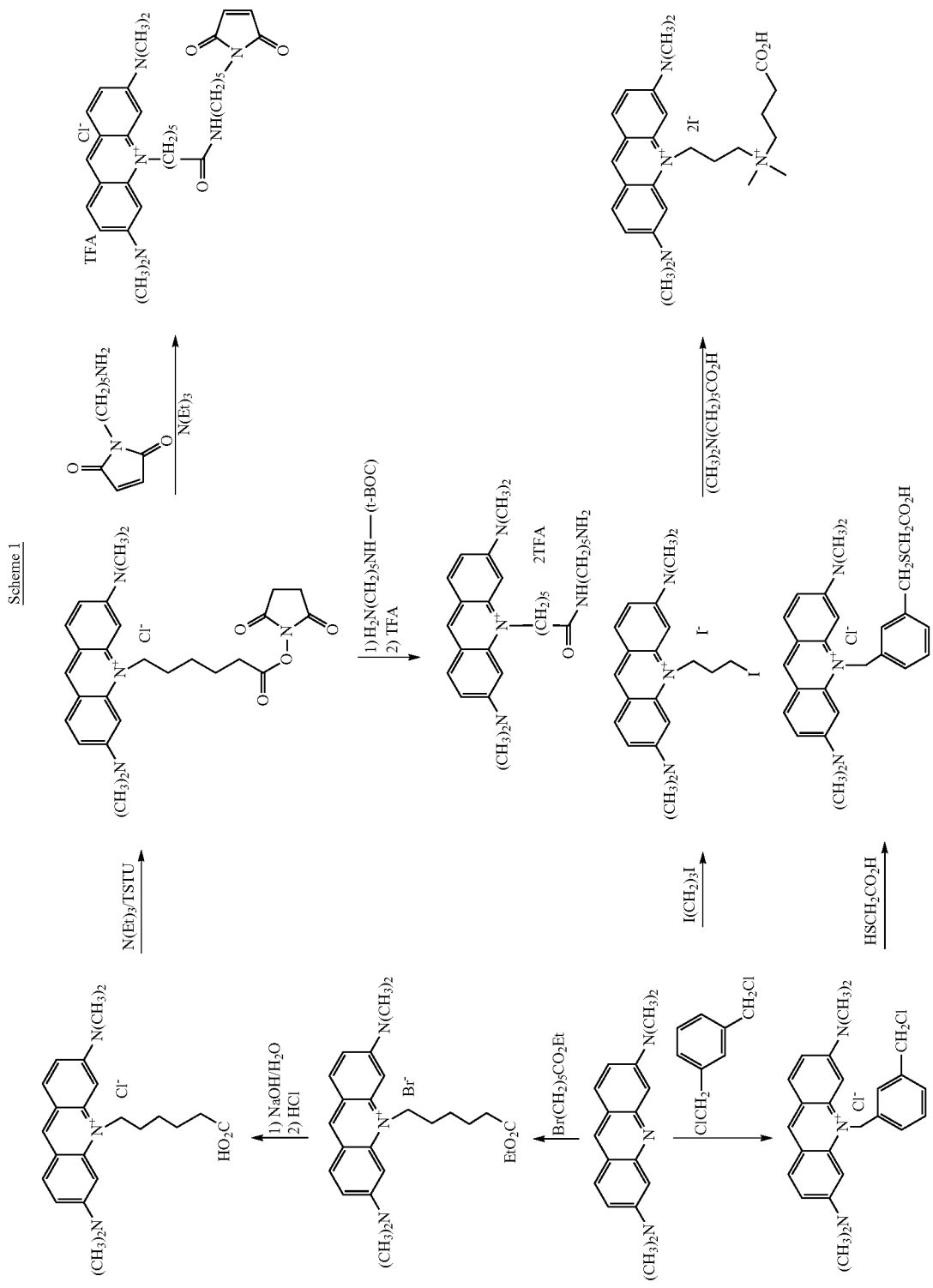

The 9-position of 10-alkylated acridine may be substituted with a cyano group, which may be further hydrolyzed to a carboxamide group, as schematically illustrated in Scheme 2 directly below.

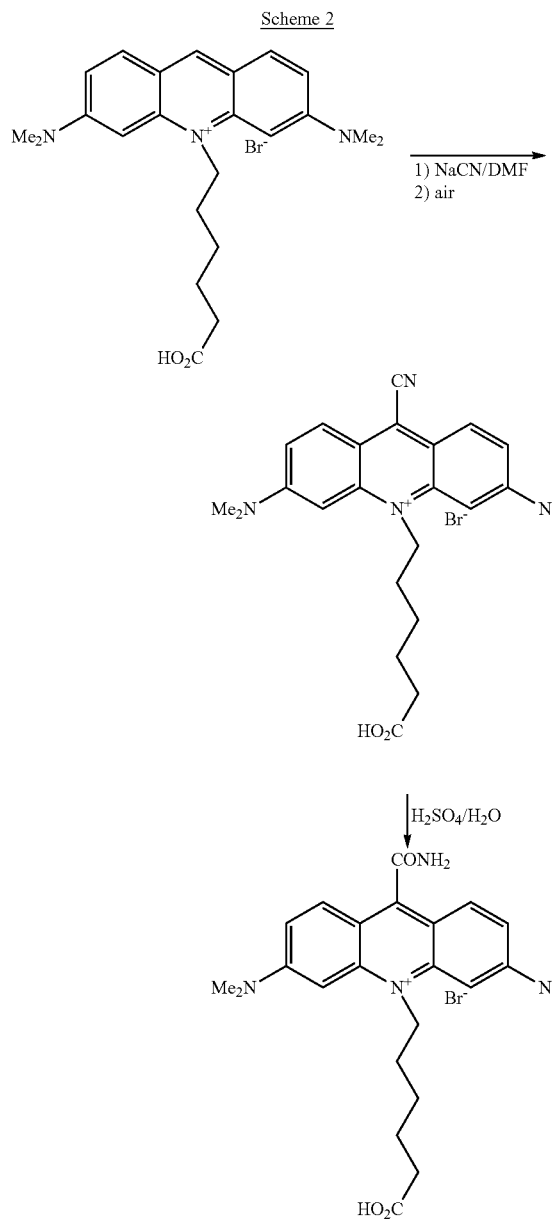

Methods of preparing reactive monomeric asymmetric cyanine dyes have been described. Carreon, et al., *Org. Lett.* 6(4), 517 (2004). Such a dye may have the structure (Structure 9) set forth directly below.

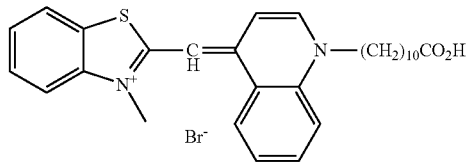

Structure 9

U.S. Pat. No. 5,863,753 discloses the preparation of a series of reactive asymmetric cyanine dyes, including ones that have a substituent ortho to the quinolinium or pyridinium nitrogen. Such a substituent, especially a cyclic substituent, ortho to the quinolinium or pyridinium nitrogen, is said to confer desired properties to the asymmetric cyanine dyes, according to U.S. Pat. No. 5,436,134. These cyclically substituted asymmetric cyanine dyes are commonly referred to as SYBR dyes. Zipper, et al., *Nucleic Acids Res.* 32(12), e103 (2004). Some of the reactive SYBR dyes are commercially available from Molecular Probes, Inc. (Eugene, Oreg.), although the exact structures of these dyes are not known. Haugland, R. P., *Handbook of Fluorescent Probes and Research Chemicals*, 9th edition.

U.S. Patent Application Publication No. 2004/0132046 discloses methods for preparing monomeric asymmetric cyanine dyes with minor groove-binding capability. In general, these dyes possess a crescent-shaped structure by virtue of having an additional benzazolyl substitutent on the benzazolyl ring of the dyes. Similar monomeric dyes having a suitable reactive group may be prepared using similar methods, for example, as schematically illustrated in Scheme 3 directly below.

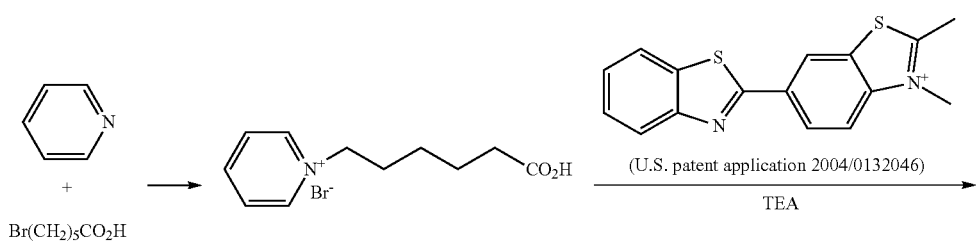

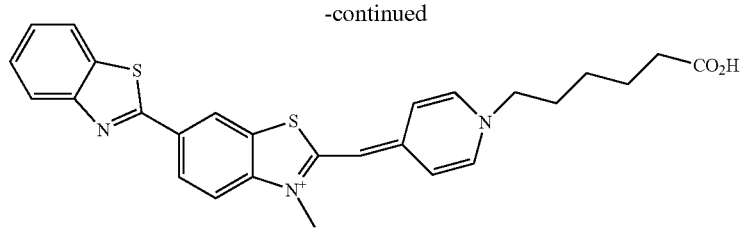
↓ TSTU/TEA
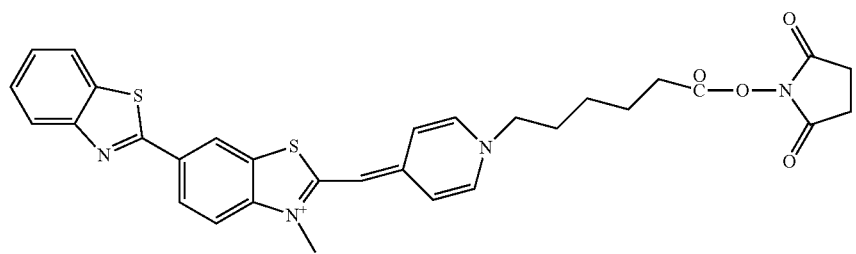
Reactive phenanthridinium dyes may be prepared from the commercially available 3,8-diamino-6-phenylphenanthridine, as schematically illustrated in Scheme 4 directly below.
Scheme 4
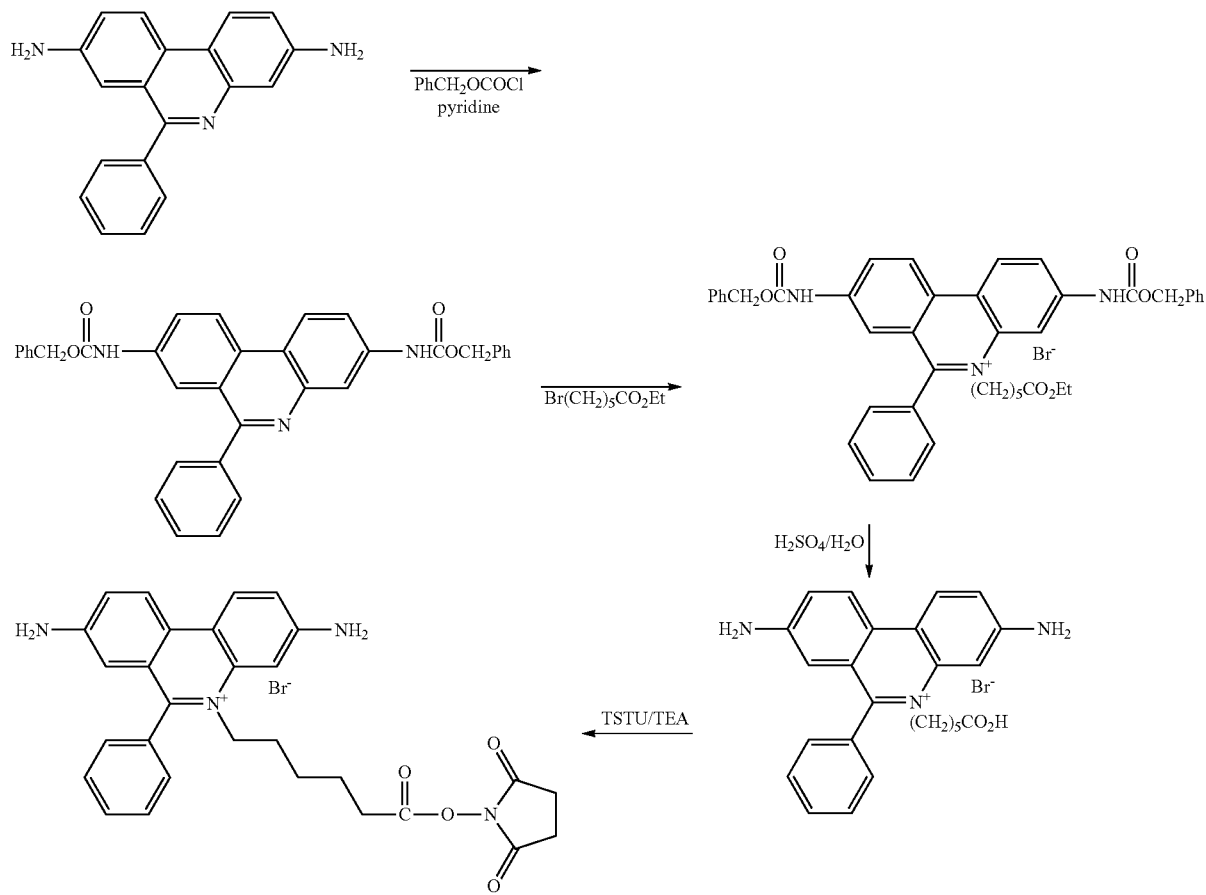

Preparations of pyronin derivatives with a reactive group at the 9-position may be carried out by condensing two equivalents of m-aminophenol derivative with one equivalent of dicarboxylic anhydride, as schematically illustrated in Scheme 5 directly below.

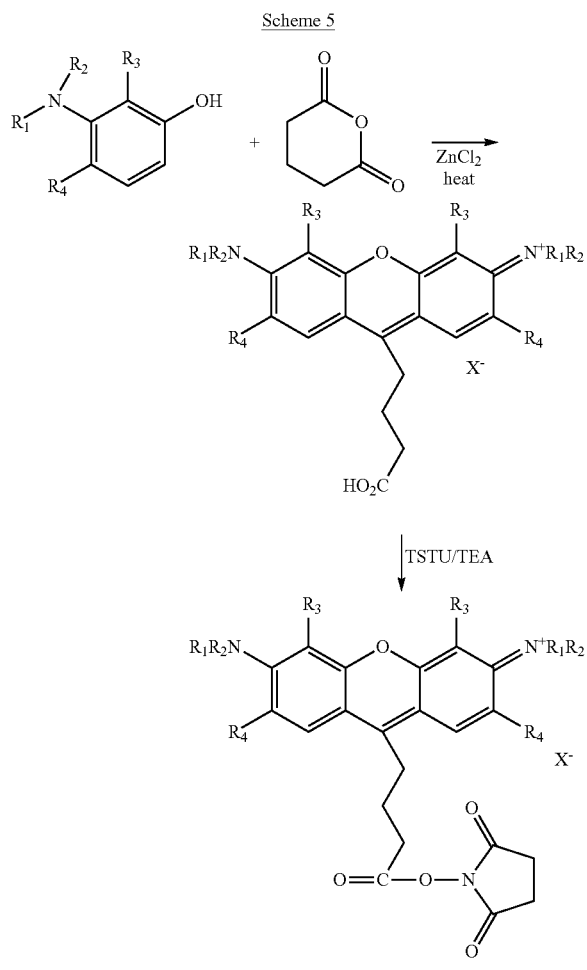

Many monomeric non-fluorescent nucleic acid-binding dyes are known pigments used in textile and ink industries and are commercially available. References for preparations of these dyes can be found in the literature. Many suitable reactive monomeric fluorescent non-nucleic acid dyes and non-fluorescent non-nucleic acid dyes are commercially available or may be prepared using known methods.

BRIDGE is usually formed when the monomeric dyes are coupled to a bi-functional group, which is often commercially available. In general, the terminal portions of BRIDGE are from the monomeric dyes themselves, while the middle portion of BRIDGE is from a bi-functional molecule available from a commercial source. In some cases, a portion or a significant portion of BRIDGE, such as up to about 90%, for example, may be pre-attached to the monomeric dyes prior to the final assembly of the dimeric dye. In some other cases, most of BRIDGE may be prepared separately before the monomeric dyes are attached. In the case of heterodimer synthesis, a mono-protected bi-functional linker group is usually first attached to one monomeric dye, followed by deprotection and coupling to the second monomeric dye.

In general, dimeric may be assembled by conjugating monomeric dyes having a suitable reactive group with a bi-functional linker in a one-step coupling reaction for some of the homodimers, or in multi-step reactions for heterodimers or some of the homodimers comprising multiple bridge element A. Examples of synthetic routes to selected homodimer and heterodimers are schematically illustrated in Scheme 6 directly below.

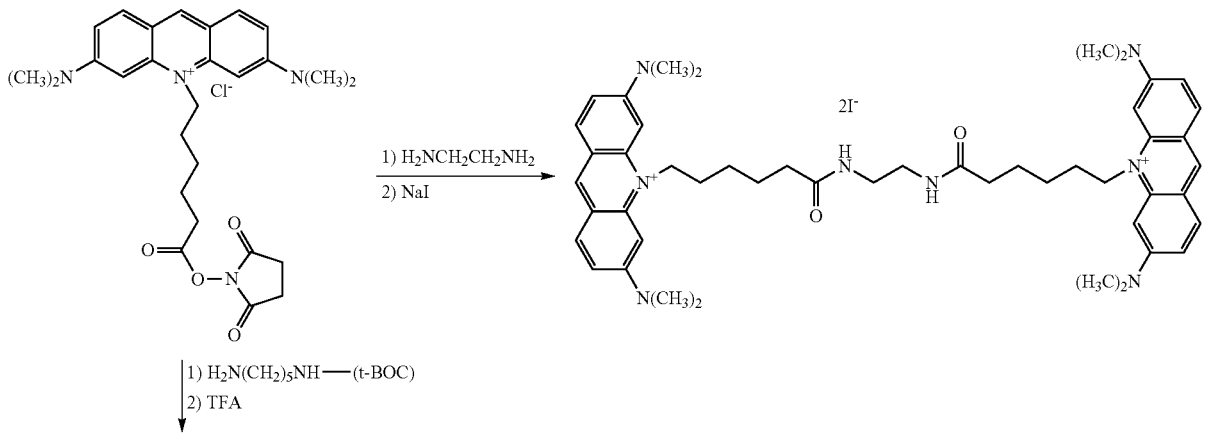

75
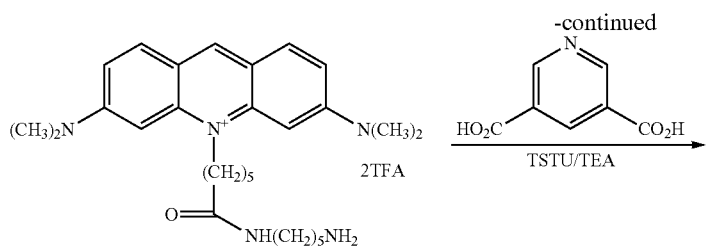
-continued
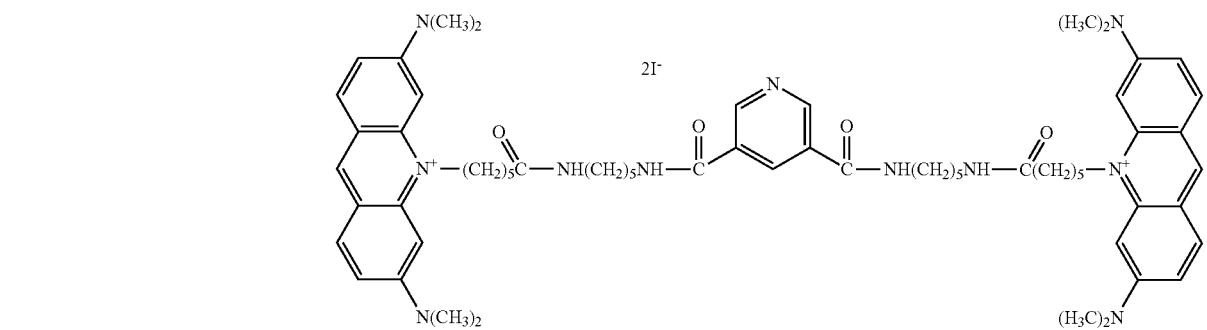
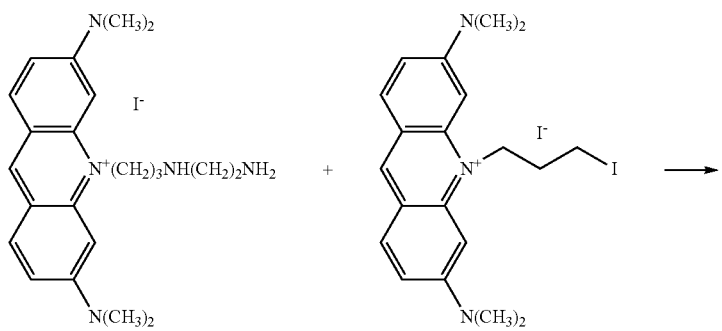
76
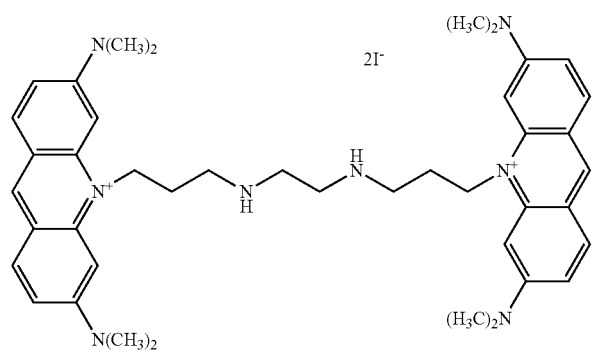
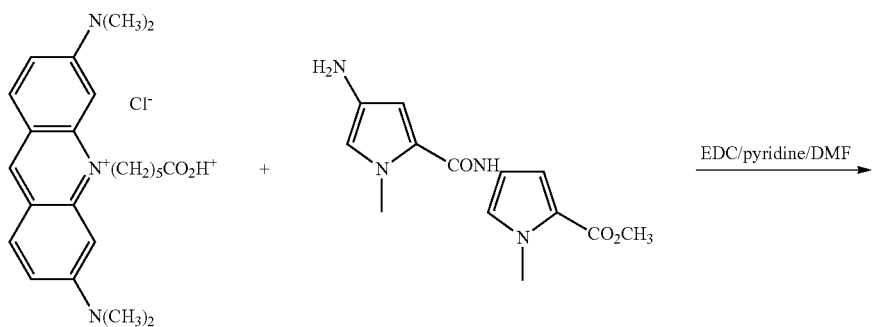

77
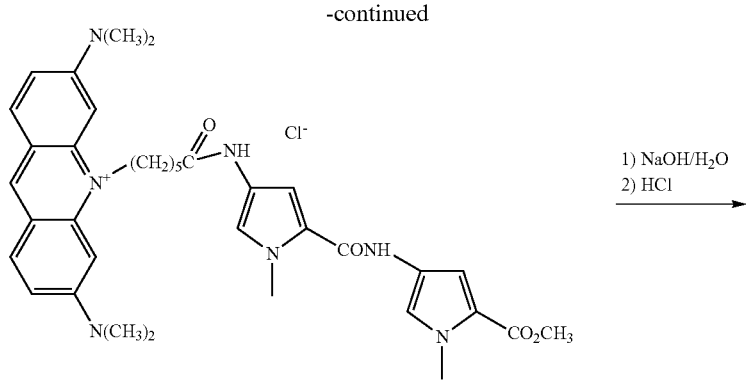
1) NaOH/H₂O
2) HCl
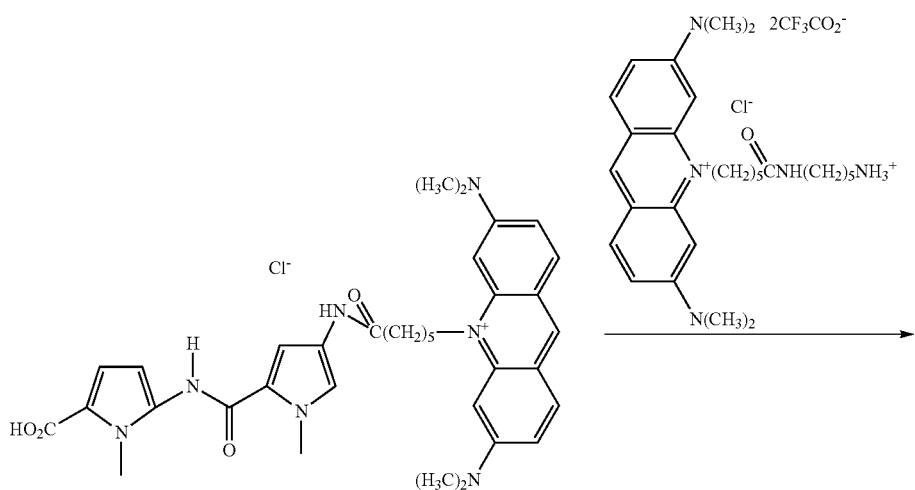
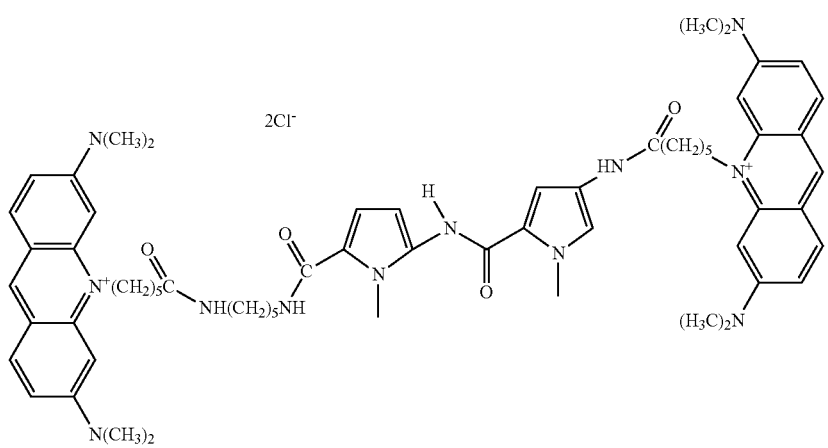
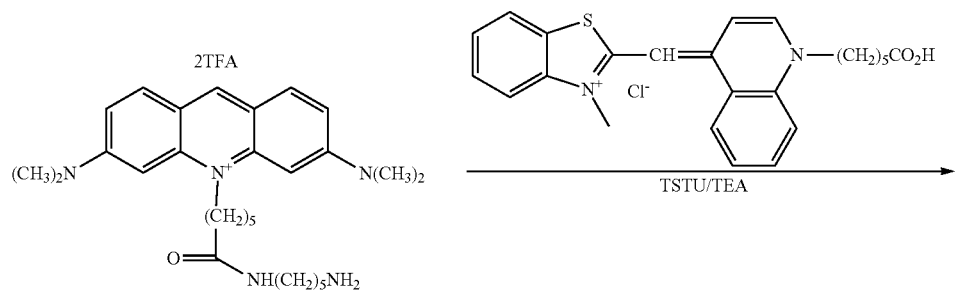
TSTU/TEA
78

-continued

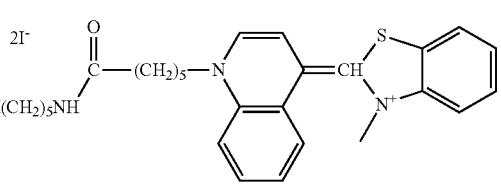

EXAMPLES

Example 1

Preparation of 10-(3-Iodopropyl)acridine orange, iodide

One equivalent of 1,3-diiodopropane was added to a suspension of 5 g of acridine orange (Aldrich) in 10 mL of chlorobenzene. The resulting mixture was stirred at 90-100° C. overnight. The hot reaction mixture was poured into ~200 mL of EtOAc. The orange precipitate was collected by filtration and dried under vacuum, yielding ~8 g.

Example 2

Preparation of 10-(5-Carboxypentyl)acridine orange, chloride salt 10-(5-Ethoxycarbonylpentyl)acridine bromide was prepared using the procedure of Example 1, with the exception that 1,3-diiodopropane was replaced with ethyl 6-bromohexanoic acid. The crude product (5 g) was suspended in ~100 mL methanol and 3 equivalents of NaOH dissolved in 30 mL $H_2O$. The suspension was stirred at room temperature for 24 h. Methanol was removed by evaporation, and the remaining aqueous solution was acidified with concentrated HCl. About 50 mL saturated NaCl was added to precipitate the product. The product was collected by filtration and then dried under vacuum at 45° C. for 24 hours.

Example 3

Preparation of DMAO (Dye No. 1 of Table 1)

10-(3-Iodopropyl)acridine orange, iodide (100 mg) was suspended in 20 mL 2M dimethylamine in methanol in a sealed tube and then stirred at 60° C. overnight. The mixture was cooled to room temperature and then poured into 50 mL EtOAc. The precipitate was collected by centrifugation and then dried under vacuum at 40° C. for 24 hours.

Example 4

Preparation of TMAO (Dye No. 2 of Table 1)

A mixture of DMAO (Dye No. 1 of Table 1) (11 mg, 0.023 mmol) and $CH_3I$ (0.5 mL) in $CH_3OH$ (2 mL) was refluxed gently for 4 days. The orange product (10 mg) was collected by suction filtration.

Example 5

Preparation of PMAO (Dye No. 5 of Table 1)

A mixture of 10-(3-iodopropyl)acridine orange iodide salt (100 mg, 0.18 mmol) and N,N,N'N'-tetramethyl-1,3-propanediamine (0.3 mL, 1.8 mmol) in $CH_3OH$ (10 mL) was refluxed overnight. After cooling down to room temperature, the precipitate was collected by suction filtration. The precipitate was resuspended in $CH_3OH$ (5 mL) and refluxed overnight and collected by suction filtration. It was dried to a constant weight in vacuo to give a dark red solid (14 mg).

Example 6

Preparation of AOAO-2Q (Dye No. 9 of Table 1)

A mixture of 10-(3-iodopropyl)acridine orange iodide salt (81 mg, 0.15 mmol) and PMAO (100 mg, 0.15 mmol) in DMF (1.5 mL) was heated at 130° C. for 7 hours. After cooling down to room temperature, $CH_3OH$ (15 mL) was added and the suspension was heated to reflux for 1 hour. Suction filtration gave the product as dark red solid (83.1 mg).

Example 7

Preparation of AOAO-2 (Dye No. 7 of Table 1)

$Et_3N$ (0.15 mL, 1.05 mmol) and TSTU (320 mg, 1.05 mmol) were added to a suspension of 10-(5-carboxypentyl) acridine orange chloride salt (438 mg, 1.03 mmol) in DMF (5 mL) at room temperature. The mixture was stirred at room temperature for 15 minutes, followed by the addition of $Et_3N$ (0.1 mL) and 3,3'-diamino-N-methyldipropylamine (50 mg, 0.344 mmol). After the mixture was stirred at room temperature overnight, EtOAc (20 mL) was added to precipitate the product. The crude product was re-dissolved in DMF and precipitated out again with EtOAc. The solid (250 mg) was separated by centrifugation.

Example 8

Preparation of AOAO-3 (Dye No. 8 of Table 1)

The dye (393 mg) was prepared by using the procedure to synthesize AOAO-2 from 10-(5-carboxypentyl)acridine orange (432 mg, 1.03 mmol) and ethylenediamine (25 mg, 0.42 mmol).

Example 9

Preparation of 10-(8-Bromooctyl)acridine orange bromide

A mixture of acridine orange (2 g, 7.53 mmol) and 1,8-dibromooctane (12 mL, 67.8 mmol) in chlorobenzene (15 mL) was heated at 110° C. overnight. EtOAc (50 mL) was added and the suspension was refluxed for 1 hour. After cooling down to room temperature, suction filtration gave the product as orange solid (3.56 g).

Example 10

Preparation of AOAO-5 (Dye No. 11 of Table 1)

A mixture of 10-(8-bromoactyl)acridine orange bromide (0.5 g, 0.94 mmol) and acridine orange (0.3 g, 11.2 mmol) in DMF (5 mL) was heated at 130° C. overnight. EtOAc was added to precipitate the product. Repeat precipitate from DMF and EtOAc gave the product as dark red solid (214 mg).

Example 11

Preparation of AOAO-7 (Dye No. 13 of Table 1)

The dye (30 mg) was synthesized by using the procedure to make AOAO-2 from 10-(5-carboxypentyl)acridine orange chloride salt (121 mg, 0.29 mmol) and 1,5-diamino-pentane dihydrochloride (20 mg, 0.12 mmol).

Example 12

Preparation of AOAO-8 (Dye No. 15 of Table 1)

The dye (182 mg) was synthesized by using the procedure to make AOAO-2 from 10-(5-carboxypentyl)acridine orange chloride salt (241 mg, 0.58 mmol) and piperazine (20 mg, 0.23 mmol).

Example 13

Preparation of AOAO-11 (Dye No. 18 of Table 1)

The dye (112 mg) was synthesized by using the procedure to make AOAO-2 from 10-(5-carboxypentyl)acridine orange chloride salt (180 mg, 0.43 mmol) and 1,8-diamino-octane (25 mg, 0.17 mmol).

Example 14

Preparation of AOAO-12 (Dye No. 19 of Table 1)

The dye (76 mg) was synthesized by using the procedure to make AOAO-2 from 10-(5-carboxypentyl)acridine orange chloride salt (147 mg, 0.35 mmol) and 2,2'oxybis(ethyl-amine)dihydrochloride (25 mg, 0.14 mmol).

Example 15

Preparation of AOAO-13 (Dye No. 20 of Table 1)

The dye (64 mg) was synthesized by using the procedure to make AOAO-2 from 10-(5-carboxypentyl)acridine orange chloride salt (96 mg, 0.23 mmol) and 4,7,10-trioxa-1,13-tridecanediamine (20 mg, 0.09 mmol).

Example 16

Preparation of 1,3-Di-((2-(N-t-Boc-amino)ethyl) aminocarbonyl)benzene (Dye No. 101, shown directly below)

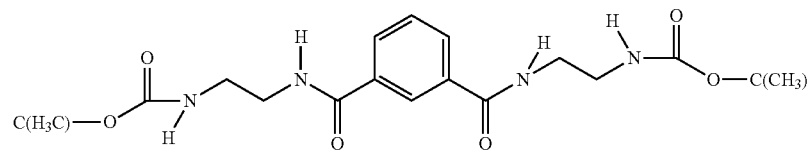

Et$_3$N (0.4 mL, 2.71 mmol) and TSTU (820 mg, 2.71 mmol) were added to a solution of isophthalic acid (220 mg, 1.32 mmol) in DMF (2 mL) at room temperature. The mixture was stirred at room temperature for 30 minutes. Addition of Et$_3$N (1 mL) and mono-tBoc-ethylenediamine (460 mg, 2.86 mmol) followed. The mixture was stirred at room temperature overnight and then partitioned between 1N HCl (100 mL) and EtOAc (50 mL). The aqueous layer was extracted with EtOAc (50 mL) and the combined organic layers were washed with 1N HCl (2×50 mL), H$_2$O (50 mL), and saturated NaCl (50 mL), and dried with anhydrous Na$_2$SO$_4$. The crude product was purified by column chromatography using EtOAc:hexanes (9:1) as eluent to give the colorless solid product (356 mg).

Example 17

Preparation of 1,3-Di-((2-aminoethyl)aminocarbonyl)benzene, trifluoro-acetic acid salt (Dye No. 102, shown directly below)

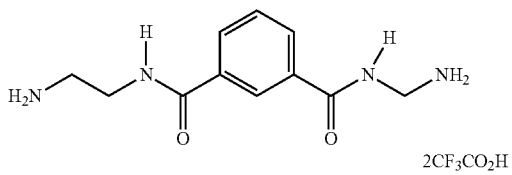 [SMILES: NCCNC(=O)c1cccc(C(=O)NCN)c1]

1,3-di-((2-(N-t-Boc-amino)ethyl)aminocarbonyl)benzene (356 mg, 0.79 mmol) was added to TFA (5 mL) at 0° C. The mixture was stirred at 0° C. for 1 hour and the solution was concentrated to dryness in vacuo. The colorless residue was dissolved in CH$_3$OH (2 mL) and added dropwise to Et$_2$O (30 mL). The precipitate was collected by centrifugation and dried to a constant weight in vacuo to give the solid product (425 mg).

Example 18

Preparation of AOAO-9 (Dye No. 16 of Table 1)

The dye (55 mg) was prepared by using the procedure to make AOAO-2 from 10-(5-carboxypentyl)acridine orange chloride salt (109 mg, 0.26 mmol) and 1,3-Di((2-aminoethyl)aminocarbonyl)benzene, trifluoroacetic acid salt (50 mg, 0.1 mmol).

Example 19

Preparation of 1,3-Di((5-(N-t-Boc-amino)pentyl)aminocarbonyl)benzene (Dye No. 103, shown directly below)

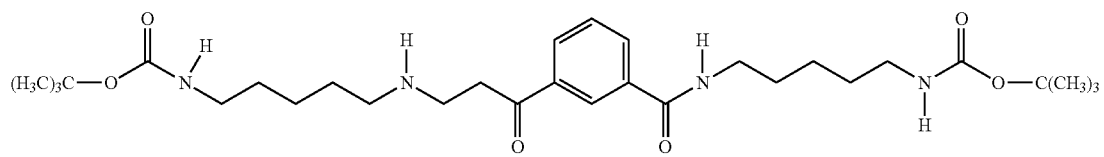 [SMILES: CC(C)(C)OC(=O)NCCCCCNCCC(=O)c1cccc(C(=O)NCCCCCNC(=O)OC(C)(C)C)c1]

The dye (555 mg) was prepared according to the procedure to make 1,3-di-((2-(N-t-Boc-amino)ethyl)aminocarbonyl)benzene from isophthalic acid (254 mg, 1.53 mmol) and mono-tBoc cadaverine (640 mg, 3.15 mmol).

Example 20

Preparation of 1,3-Di-((5-aminopentyl)aminocarbonyl)benzene, trifluoro-acetic acid salt (Dye No. 104, shown directly below)

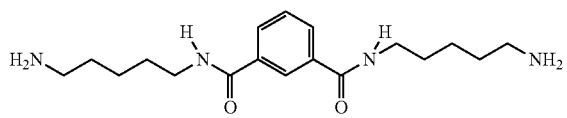

The dye (560 mg) was prepared according to the procedure for Dye No. 102 (555 mg, 1.04 mmol).

Example 21

Preparation of AOAO-10 (Dye No. 17 of Table 1)

The dye (22 mg) was prepared by using the procedure to make AOAO-2 from 10-(5-carboxypentyl)acridine orange chloride (95 mg, 0.23 mmol) and Dye No. 104 (50 mg, 0.09 mmol).

Example 22

Preparation of AOAO-14 (Dye No. 21 of Table 1)

The dye (150 mg) was prepared by using the procedure to make AOAO-2 from 10-(5-carboxypentyl)acridine orange chloride (166 mg, 0.40 mmol) and diamido-dPEG-diamine (Quanta Biodesign of Powell, Ohio) (100 mg, 0.15 mmol).

Example 23

Preparation of 10-((((3-(N-Boc-amino)propyl)-N,N-dimethyl)ammonium)propyl) acridine, diiodide (Dye No. 105, shown directly below)

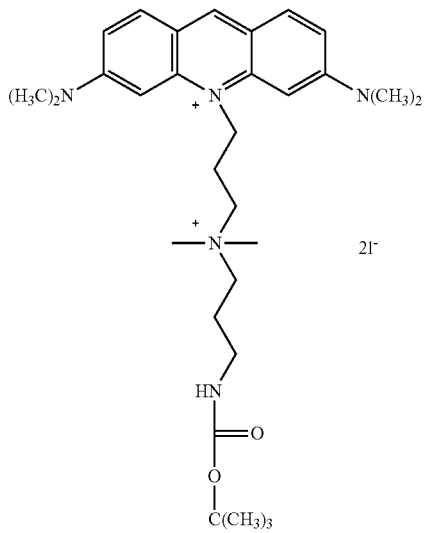

A mixture of 10-(3-iodopropyl)acridine orange iodide (500 mg, 0.89 mmol) and 3-(N-t-Boc-amino)propyl-N,N-dimethylamine (1.8 g, 8.9 mmol) in $CH_3OH$ (50 mL) was refluxed overnight. After cooling down to room temperature, the precipitate was collected by suction filtration and dried to a constant weight to give Dye No. 105 as an orange solid (292 mg).

Example 24

Preparation of 10-((((3-ammonium)propyl)-N,N-dimethyl)ammonium)propyl acridine, trifluoroacetate salt (Dye No. 106, shown directly below)

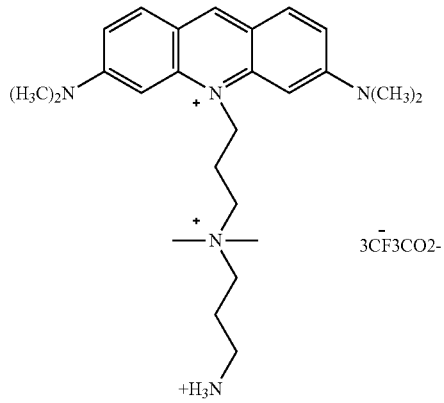

Dye No. 105 (50 mg, 0.06 mmol) was added to TFA (2 mL) at 0° C. The mixture was stirred at 0° C. for 30 minutes. The solution was concentrated to dryness in vacuo and the residue was dissolved in $CH_3OH$ (3 mL). The solution was added dropwise to $Et_2O$ (30 mL) and the precipitate was collected by centrifugation and dried to a constant weight in vacuo to give Dye No. 106 as an orange solid (28 mg).

Example 25

Preparation of AOAO-4 (Dye No. 10 of Table 1)

The dye (23 mg) was prepared by using the procedure to make AOAO-2 from 10-(5-carboxypentyl)acridine orange chloride salt (31 mg, 0.075 mmol) and Dye No. 106 (28 mg, 0.036 mmol).

Example 26

Preparation of 10-(6-(N-Phthalimido)hexyl)acridine orange bromide salt (Dye No. 107, shown directly below)

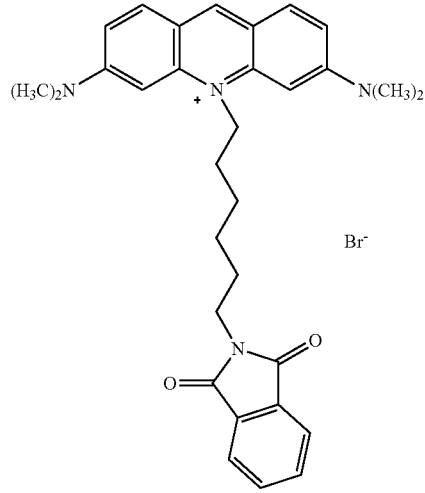

A mixture of acridine orange (2 g, 7.54 mmol) and N-(6-bromohexyl)phthalimide (4.7 g, 15.1 mmol) in chlorobenzene (20 mL) was heated at 110° C. for 2 days. EtOAc (50 mL) was added and the suspension was heated to reflux for 1 hour. After cooling down to room temperature, the product Dye No. 107 was collected by suction filtration as an orange solid (3.76 g).

Example 27

Preparation of 10-(5-((5-Carboxypentyl)aminocarbonyl)pentyl)acridine orange, iodide (Dye No. 108, shown directly below)

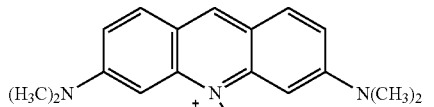
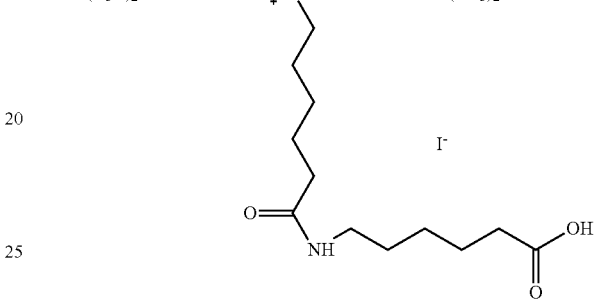

$Et_3N$ (40 µL, 0.28 mmol) and TSTU (81 mg, 0.27 mmol) were added to a suspension of 10-(5-carboxypentyl)acridine orange chloride (107 mg, 0.258 mmol) in DMF (3 mL). The mixture was stirred at room temperature for 15 minutes. Addition of $Et_3N$ (0.2 mL) and a solution of 6-aminohexanoic acid (67 mg, 0.5 mmol) in $H_2O$ (1 mL) followed. The mixture was stirred at room temperature for 1 hour and concentrated to dryness in vacuo. The residue was triturated with $H_2O$ to give Dye No. 108 as an orange solid (125 mg).

Example 28

Preparation of 9-Cyano-10-(5-carboxypentyl)acridine orange, chloride (Dye No. 109, shown directly below)

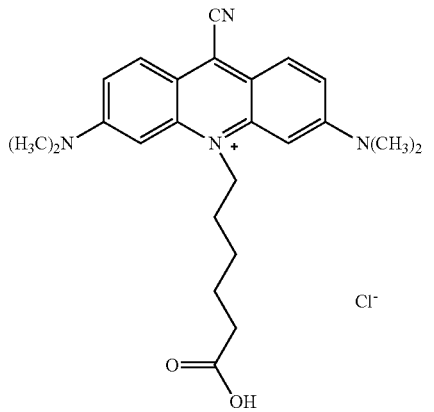

A mixture of 10-(5-carboxypentyl)acridine orange (0.15 g, 0.361 mmol) and sodium cyanide (35 mg, 0.722 mmol) in DMF (3 mL) was stirred at room temperature in open air for 2 days. $CH_3CN$ (10 mL) was added and the resulting suspension was stirred at room temperature for 1 hour. The dark blue precipitate was collected by centrifugation and dried to a constant weight in vacuo to give Dye No. 109 (130 mg).

Example 29

Preparation of AOAO-12R (Dye No. 22 of Table 1)

Et₃N (32 µL, 0.23 mmol) and TSTU (68 mg, 0.227 mmol) were added to a solution of Dye No. 109 (98.3 mg, 0.223 mmol) in DMF (2 mL) at room temperature. The mixture was stirred at room temperature for 15 minutes. Addition of Et₃N (100 µL) and 2,2'-oxybis-(ethylamine)dihydrochloride (16 mg, 0.09 mmol) followed. The mixture was stirred at room temperature for 2 days. The solution was concentrated to about 1 mL and EtOAc (2 mL) was added. The precipitate was collected by centrifugation. The product was re-dissolved in DMF and precipitated again with EtOAc to give Dye No. 22 as a dark blue solid (54.4 mg).

Example 30

Preparation of 9-Aminocarbonyl-10-(5-carboxyphentyl)acridine (Dye No. 110, shown directly below)

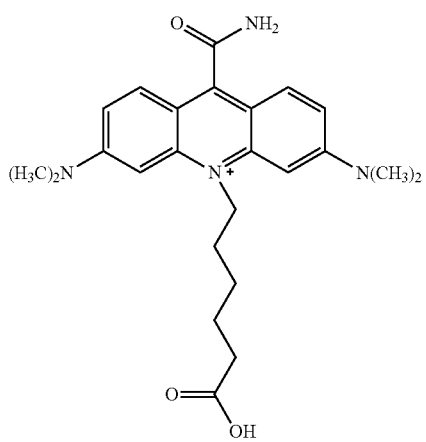

A solution of Dye No. 109 (30 mg, 0.068 mmol) in 75% $H_2SO_4$ (1 mL) was heated at 60° C. for 2 days. After cooling down to room temperature, the mixture was added to $Et_2O$ (10 mL). The precipitate was collected by centrifugation and re-dissolved in $CH_3OH$ (1.5 mL). EtOAc (10 mL) was added and the solid precipitate was collected by centrifugation and dried to a constant weight in vacuo to give Dye No. 110 as a dark pink solid (20.4 mg).

Example 31

Preparation of N-Carboxypentyl Thiazole Orange (Shown Directly Below)

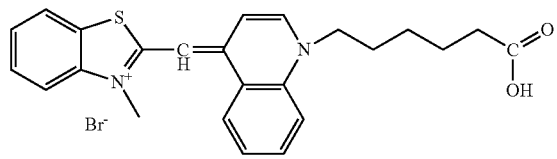 [SMILES: C[n+]1c(C=C2C=CN(CCCCCC(=O)O)c3ccccc32)sc2ccccc21 ; [Br-]]

The dye was prepared using published procedure (Carreon, et al., *Org. Let.* 6(4), 517 (2004)).

Example 32

Preparation of TOTO-3 (Dye No. 14 of Table 1)

The dye (354 mg) was prepared using the procedure to synthesize AOAO-2 from N-Carboxypentyl thiazole orange (460 mg, 1.04 mmol) and ethylene diamine (25 mg, 0.42 mmol).

Example 33

Preparation of 10-(5-(2-(N-t-Boc-amino)ethyl)aminocarbonyl)pentyl)acridine orange chloride salt (Dye No. 111, shown directly below)

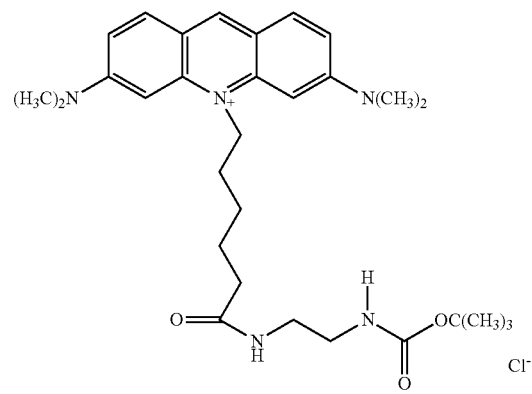

Et₃N (106 µL, 0.76 mmol) and TSTU (230 mg, 0.76 mmol) were added to a suspension of 10-(5-carboxypentyl)acridine orange chloride (302 mg, 0.73 mmol) in DMF (3 mL). The mixture was stirred at room temperature for 15 minutes. The addition of Et₃N (350 mL) and mono t-BOC-ethylenediamine (150 mg, 0.92 mmol) followed. The mixture was stirred at room temperature for 1 hour and then concentrated to dryness in vacuo. The residue was dissolved in $CH_3CN$ (2 mL) and precipitated by the addition of EtOAc (20 mL). The precipitate was collected by centrifugation and dried to a constant weight to give Dye No. 111 as orange solid (365 mg).

Example 34

Preparation of 10-(5-((2-Ammoniumethyl)aminocarbonyl)pentyl)acridine orange, trifluoroacetate (Dye No. 112, shown directly below)

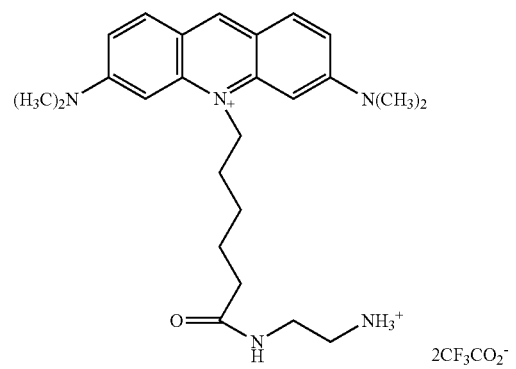

Dye No. 111 (347 mg, 622 mmol) was added in one portion to trifluoroacetic acid (3 mL) at 5° C. The mixture was stirred at 5° C. for 1 hour and concentrated to dryness in vacuo. The residue was dissolved in $CH_3OH$ (3 mL) and added dropwise to $Et_2O$ (50 mL). The precipitate was collected by centrifugation to give Dye No. 112 as orange solid (297 mg).

Example 35

Preparation of AOTO-3 (Dye No. 23 of Table 1)

Et$_3$N (20 μL, 0.142 mmol) and TSTU (42.2 mg, 0.142 mmol) were added to a solution of N-carboxypentylthiazole orange (62 mg, 0.142 mmol) in DMF (1 mL). The mixture was stirred at room temperature for 15 minutes. Addition of Et$_3$N (70 μL) and Dye No. 112 (50 mg, 0.095 mmol) followed. The mixture was stirred at room temperature for 2 hours and then concentrated to dryness in vacuo. The residue was re-dissolved in DMF (1 mL) and EtOAc (2 mL) was added. The precipitate was collected by centrifugation. Repeated precipitation from DMF and EtOAc gave the product as orange red solid (50.4 mg)

Example 36

Preparation of TOTO-12 (Dye No. 24 of Table 1)

The dye (19.4 mg) was prepared by using the procedure to synthesize AOAO-2 from N-carboxypentylthiazole orange (94.5 mg, 0.2145 mmol) and 2,2'oxybis(ethylamine)dihydrochloride (15 mg, 0.085 mmol).

Example 37

Preparation of TO(3)TO(3)-12 (Dye No. 25 of Table 1)

The dye (32.6 mg) was prepared by using the procedure to synthesize AOAO-2 from N-carboxypentyl thazole blue (Carreon, et al., Org. Let. 6(4), 517 (2004); and Benson, et al., Nucleic Acid Res. 21(24), 5727 (1993)) (99 mg, 0.212 mmol) and 2,2'oxybis(ethylamine)dihydrochloride (15 mg, 0.085 mmol).

Example 38

Preparation of TO(3)TO(3)-2 (Dye No. 26 of Table 1)

The dye (28.4 mg) was prepared by using the procedure to synthesize AOAO-2 from N-carboxypentyl thazole blue (76 mg, 0.173 mmol) and 3,3'-diamino-N-methyldi-propylamine (10 mg, 0.069 mmol).

Example 39

Preparation of 10-(5-((5-(N-t-Boc-amino)pentyl)aminocarbonyl)pentyl)acridine orange, chloride (Dye No. 113, shown directly below)

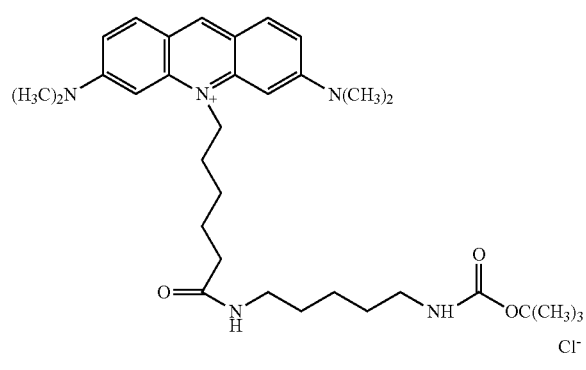

The dye (280 mg) was prepared by using the procedure to synthesize Dye No. 111 from 10-(5-carboxypentyl)acridine orange chloride (200 mg, 0.483 mmol) and mono t-BOC-cadaverine (130 mg, 0.628 mmol).

Example 40

Preparation of 10-(5-((5-ammoniumpentyl)aminocarbonyl)pentyl)acridine orange, trifluoroacetate (Dye No. 114, shown directly below)

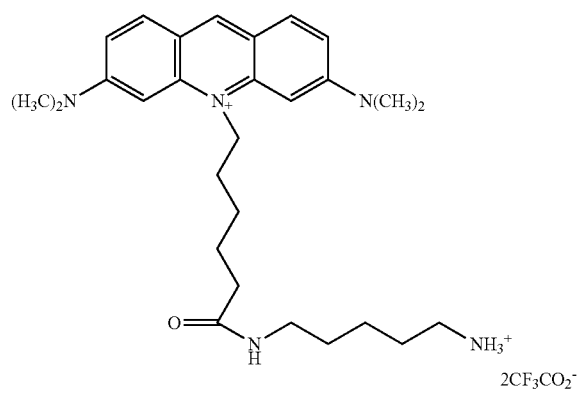

Dye No. 114 (234 mg) was prepared by using the procedure to synthesize Dye No. 112 from Dye No. 113 (280 mg, 0.467 mmol).

Example 41

Preparation of AORO-7 (Dye No. 27 of Table 1)

The compound (29 mg) was prepared by using the procedure to synthesize AOTO-3 from compound No. 114 (35 mg, 0.06 mmol) and the rosamine dye (Biotium, Inc. (Hayward, Calif.)) (40 mg, 0.063 mmol).

Example 42

Preparation of TOTO-13 (Dye No. 29 of Table 1)

The compound (102 mg) was prepared by using the procedure to synthesize AOAO-2 (Dye No. 7 of Table 1) from N-carboxypentyl thiazole orange (102 mg, 0.23 mmole) (Example 31) and 4,7,10-trioxa-1,13-tridecanediamine (23 mg, 0.1 mole).

Example 43

Preparation of N-(5-carboxypentyl)-4-(4-(dimethylamino)styryl)pyridinium bromide A mixture of 4-N,N-dimethylaminobenzaldehyde (3 g, 20 mmoles), N-(5-carboxypentyl)picolinium bromide (5.6 g, 20 mmoles) and piperidine (2 mL) in ethanol (100 mL) was heated at 60° C. overnight. The mixture was evaporated to dryness in vacuo. The residue was redissolved in methanol and then precipitated with ether to give the title product (6.7 g).

Example 44

Preparation of STST-19 (Dye No. 31 of Table 1)

The dye (85 mg) was prepared by using the procedure to make AOAO-2 (Example 7) from N-(5-carboxypentyl)-4-(4-(dimethylamino)styryl)pyridinium bromide (Example 43) (200 mg, 0.5 mmole) and 2,2'-oxybis(ethylamine)dihydrochloride (36 mg, 0.2 mmoles).

Example 45

Preparation of STST-27 (Dye No. 30 of Table 1)

The dye (81.8 mg) was prepared by using the procedure to make AOAO-2 (Example 7) from N-(5-carboxypentyl)-4-(4-(dimethylamino)styryl)pyridinium bromide (Example 43) (200 mg, 0.5 mmole) and 4,7,10-trioxa-1,13-tridecanediamine (44 mg, 0.2 mmoles).

Example 46

Absorbance and Fluorescence of DMAO and AOAO-7

The absorbance spectra, as shown in FIG. 2 and FIG. 3, and fluorescence emission spectra, as shown in FIG. 4, of DMAO and AOAO-7, were measured separately without DNA presence, or with DNA presence (2 mg/ml of salmon sperm DNA), in PBS buffer. All dye concentrations were adjusted to provide an optical density of 0.05 at 495 nm. The spectra were normalized to 1 in the absorbance plot. Relative to DMAO, AOAO-7 exhibits a new shorter wavelength peak at 471 nm in absorbance, indicating aggregation of the two acridine monomers within AOAO-7. Upon binding to DNA, absorbances of AOAO-7 and DMAO showed 5 nm- and 10 nm-red shifts, respectively, relative to free dyes. The fluorescence of free AOAO-7 is about 5 times lower than that of DMAO. The fluorescence per acridine monomer of AOAO-7 is close to that of DMAO, indicating that two monomers of AOAO-7 no longer quenched each other when bound to DNA and the linker between the two did not exhibit negative effect on the quantum yield.

Example 47

Absorbance Spectra of TOTO-1 and TOTO-3

In a similar manner to that described in connection with Example 46, the absorbance spectra of TOTO-1 and TOTO-3 were measured without DNA presence, as shown in FIG. 5, or in the presence of 2 mg/ml of salmon sperm DNA, as shown in FIG. 6, in PBS buffer. As shown in FIG. 5, the spectra of the free dyes indicate that TOTO-3, which has BRIDGE that is neutral or substantially devoid of positive charges, forms an intramolecular H-dimer, or a hairpin structure, while TOTO-1, which has multiple positive charges, has less spectral shift. As shown in FIG. 6, the absorption spectra of both TOTO-1 and TOTO-3 in the presence of DNA shift to about the same position, indicating that the hairpin structure of TOTO-3 dimer opens up upon binding to DNA, and that both TOTO-1 and TOTO-3 form similar types of DNA-dye complexes.

Example 48

Fluorescence of AOAO-12 in Response to Different Amount of DNA

The fluorescence of 0.1 µM AOAO-12 in 200 mL of PBS in the presence of 0, 0.1, 0.2, 0.4, 0.6, 0.8, 1.0, 2.0, 4.0, 6.0, 8.0 and 10 µg/ml final concentrations of salmon sperm DNA or a mixture of single-stranded 20mer oligonucleotide were measured on a microtiter plate reader (SpectraMax of Molecular Devices Corporation (Sunnyvale, Calif.)). The fluorescence was plotted against DNA concentration, as shown in FIG. 7. It can be seen that fluorescence linearly responded to DNA up to 2.0 µg/ml (inset). At higher concentrations of DNA, the response became non-linear. AOAO-12 fluoresces more intensely when bound to double stranded DNA than when bound to single stranded DNA.

Example 49

Pre-Cast DNA Gel Staining

An agarose gel solution (1% agarose) was prepared following a standard protocol (J. Roskams et al., *Lab Ref: A Handbook of Recipes, Reagents, and Other Reference Tools for Use at the Bench*, Cold Spring Harbor Laboratory Press, Cold Spring Harbor, N.Y., 2002). A stock solution of a Dye No. 35 (ET-27) of Table 1 in DMF at 12 mM concentration was prepared. An aliquot of the stock solution of dye was added to the gel solution, while it was hot, resulting in an effective working concentration of the dye of about 1.2 µM. The resulting solution was thoroughly mixed by swirling. The resulting gel solution was poured onto a gel slab to cast the gel. Serial two-fold dilutions of 1 kb Plus DNA Latter from Invitrogen Co. (Carlsbad, Calif.) were made and the resulting DNA samples were loaded onto the gel in four lanes from left to right with a loading of 200 ng, 100 ng, 50 ng, and 25 ng per lane, respectively. The DNA samples were electrophoretically separated in 1×TBE buffer using a standard protocol. The resulting gel was then viewed using a UV transilluminator with 300 nm excitation. The same procedure was followed using a stock solution of EB at about 0.5 µg/mL (or 1.3 µM) in DMF in place of the stock solution of Dye No. 35 of Table 1.

Photographs of the illuminated gels were taken with an EB filter and Polaroid 667 black-and-white film, as shown in FIG. 12. The results demonstrate that relative to EB, Dye No. 35 is more sensitive with respect to shorter DNA fragments, as shown by the number and the brightness of the bands appearing in the lower portion of the left-most photograph versus those appearing in the lower portion of the right-most photograph, and more sensitive with respect to low level DNA, as shown by the number and the brightness of the bands appearing in the right-side lanes of the left-most photograph versus those appearing in the right-side lanes of the right-most photograph. It should be noted that other dyes described herein may be prepared and employed in the manner described in this Example 49, or a similar manner.

Example 50

Post-DNA Gel Staining

Agarose gels (1% agarose) were prepared following a standard protocol (J. Roskams et al., *Lab Ref: A Handbook of Recipes, Reagents, and Other Reference Tools for Use at the Bench*, Cold Spring Harbor Laboratory Press, Cold Spring Harbor, N.Y., 2002). Serial two-fold dilutions of 1 kb Plus DNA Latter from Invitrogen Co. (Carlsbad, Calif.) were made and the resulting DNA samples were loaded onto an agarose gel in four lanes from left to right with a loading of 200 ng, 100 ng, 50 ng, and 25 ng per lane, respectively. The DNA samples were electrophoretically separated in 1×TBE buffer using a standard protocol. The nucleic acid sample was loaded onto the gel from in four columns from left to right with a loading of 200 ng, 100 ng, 50 ng, and 25 ng per lane, respectively, and electrophoretically separated in 1×TBE buffer using a standard protocol. A stock solution of a Dye No. 20 of Table 1 in DMF at about 12 mM concentration was prepared. The stock solution of dye was diluted using an appropriate aqueous solvent to provide a staining solution with an appropriate effective working concentration of the dye, which for Dye No. 20 was about 3.6 µM in TBE solvent. The agarose gel was submerged in the staining solution for approximately 30 minutes to stain the gel. The resulting gel was then viewed using a UV transilluminator with 254 nm excitation. Photographs of the fluorescent images of the illuminated gels were taken with a SYBR filter and Polaroid 667 black-and-white film.

A similar procedure was followed to prepare post gel staining solutions of Dye No. 29 of Table 1, except that Dye No. 29 was used in place of Dye No. 20 and at various conditions, as now described. Briefly, a stock solution of 12 mM Dye No. 29 in DMF was diluted 3,300 times separately with water comprising 0.1 M NaCl, with 1×TBE buffer, and with 1×TBE buffer comprising 0.1 M NaCl, thereby providing, respectively, three separate staining solutions, as follows: 3.6 µM in water with 0.1 M NaCl, 3.6 µM in 1×TBE, and 3.6 µM in 1×TBE with 0.1 M NaCl. Identical DNA samples were prepared, loaded onto three separate agarose gels, and separated via standard gel electrophoreses, in the manner described above. Each of the three separate gels was then stained by immersion in a different one of the resulting gels for about 30 minutes. The resulting stained gels were then viewed using either a UV transilluminator or a Dark Reader transilluminator and the resulting images were photographed using a SYBR filter and Polaroid 667 black-and-white film. Photographic results obtained using the first, second and third of these staining solutions are shown in FIGS. 9 (via UV transilluminator), 11 (via Dark Reader transilluminator) and 14 (via UV transilluminator), FIG. 14 (via UV transilluminator), and FIG. 14 (via UV transilluminator), respectively. It should be noted that other dyes described herein may be prepared and employed in the manner described in this Example 50, or a similar manner.

A similar procedure was followed using, in place of the stock solution of Dye No. 20, a stock solution of SYBR Safe from Molecular Probes, Inc. (Eugene, Oreg.) as a 10,000× solution in DMSO for the preparation a 1×SYBR Safe staining solution in 1×TBE; and separately, a stock solution of SYBR Green I from Molecular Probes, Inc. (Eugene, Oreg.) as a 10,000× solution in DMSO for the preparation of three separate staining solutions, as follows: a staining solution of 1×SYBR Green I in 1×TBE; a staining solution of 1×SYBR Green I in 1×TBE with 0.1 NaCl; and a staining solution of 1×SYBR Green I in water with NaCl. Identical DNA samples were prepared, loaded onto four separate agarose gels, and separated via standard gel electrophoreses, in the manner described above. Each of the four separate gels was then stained by immersion in a different one of the resulting gels for about 30 minutes. The resulting stained gels were then viewed using a UV transilluminator with 254 nm excitation and the resulting images were photographed using a SYBR filter and Polaroid 667 black-and-white film.

Photographs of various of the illuminated gels described above are shown in FIGS. 8, 9, 11 and 14, as mentioned above in the brief description of these figures, and as described previously herein.

Example 51

Excitation and Emission Spectra of Dye No. 29 of Table 1 in the Presence of dsDNA Salmon sperm dsDNA from Sigma (St. Louis, Mo.) was dissolved in pH 7 PBS buffer to provide a 10 mM/mL DNA solution. An aliquot of a stock solution of 12 mM Dye No. 29 of Table 1 in DMF was added to the DNA solution to provide a DNA-dye solution with a 0.1 µM dye concentration. The DNA-dye solution was incubated at room temperature for 1 hour. The excitation and emission spectra of the resulting solution with Dye No. 29 at 0.1 µM were measured using a Jasco fluorescence spectrophotometer at room temperature, as graphically shown in FIG. 10. The results demonstrate that Dye No. 29 can be efficiently excited by 254 nm UV light and by a visible light with wavelength in the range from about 460 nm to about 510 nm. This makes it possible to use a UV-light transilluminator or a visible-light transluminator, such as a Dark Reader or a 488 nm laser-based gel scanner, for the reading of gels that have been stained with the dye.

Example 52

Stability of Dye No. 35 of Table 1 and SYBR Gold in TBE Buffer

SYBR Gold 10,000× in DMSO from Molecular Probes, Inc. (Eugene, Oreg.) was diluted to 1× working concentration, as recommended by the manufacturer, in 1×TBE buffer. A stock solution of Dye No. 35 of Table 1 in DMSO (12 mM) was diluted to 1.2 µM in 1×TBE buffer. The optical density associated with each of the solutions was monitored at the absorption maximum of the dye (488 nm for SYBR Gold and 500 nm for Dye No. 35) over the course of a 24-hour period at room temperature. A graphical representation of normalized absorbance versus time for each of the solutions is shown in FIG. 13. As shown, the absorbance associated with Dye No. 35 was relatively constant over the 24-hour period, while the absorbance of SYBR Gold decreased by nearly 50% over the same period. This demonstrates that Dye No. 35 is relatively more stable than SYBR Gold, as previously described herein.

Example 53

Mutagenicity of EB and Dye No. 35 of Table 1

Mutagenicity assays were carried out using a Muta-ChromoPlate test kit from EBPI (Brampton, Ontario, Canada). Dye No. 35 of Table 1 and EB were assayed using three dose levels (0.25 nmole, 2.5 nmoles and 25 nmoles), respectively, for each dye, and in the absence and presence of S9 extract for each dose level and each dye, respectively. A solution without a dye (zero dose level) was assayed in the absence and presence of S9 extract, as a control or negative control. S9 extract is a rat liver extract that comprises various metabolic enzymes. The tests associated with the presence of S9 extract were undertaken to provide information on the potential genotoxicity of the metabolized dyes. Bacterium strain TA98, a frame shift indicator, was used for the tests since EB is a known frame shift mutagen as shown by Ames Test using the same bacterial strain. Each single test was carried out using 36 wells and the number of positive wells out of each 36 wells was taken as an indicator of the relative mutagenicity levels of the dye under the test conditions. The results, shown in Table 2 herein, suggest that Dye No. 35 may be less mutagenic than EB. Dye No. 35 may be particularly advantageous relative to EB given its relatively higher sensitivity in gel staining applications and its relatively greater safety in terms of toxicity or mutagenicity. Further, as the monomeric dye constituent in Dye No. 35 is structurally similar to EB, Dye No. 35 and EB have similar or essentially the same excitation and emission spectra, such that Dye No. 35 may be used in place of EB relatively easily, for example, without the need to change the transilluminator, such as a UV transilluminator that is used in association with EB and may be used with Dye No. 35, or the filter that is used in photographing transilluminated images.

A dimeric dye has been described herein. Such a dye may have any of a number of desirable properties, such as relatively low background fluorescence, good fluorescent signal strength, and good stability, for example. Generally, such a dye having at most one positive charge may have application in the detection of the presence or absence of nucleic acid immobilized in a matrix or on a solid surface.

Useful dimeric dyes have been described herein. By way of example, a dimeric dye that is suitable for detecting the presence or absence of immobilized nucleic acids in a gel matrix or on a solid surface has been described. Useful methods for nucleic acid gel staining have also been described herein. By way of example, a method of using a dye, such as a monomeric dye or a dimeric dye, for example, and a suitable salt, such as a salt comprising an anion associated with a strong acid and a cation associated with a strong base in a suitable amount, for post-nucleic acid gel staining, has been described. Useful methods of preparing any of various dyes described herein and useful methods of using any of these dyes have also been described. Useful kits suitable for determining immobilized nucleic acids, which comprises a suitable dye described herein, have also been described.

Various modifications, processes, as well as numerous structures relating to the description herein may be applicable, as will be readily apparent to those of ordinary skill in the art, upon review of the specification. Various references, publications, provisional and non-provisional United States or foreign patent applications, and/or United States or foreign patents, have been identified herein, each of which is incorporated herein in its entirety by this reference. Various aspects and features may have been explained or described in relation to understandings, beliefs, theories, underlying assumptions, and/or working or prophetic examples, although it will be understood that any such understanding, belief, theory, underlying assumption, and/or working or prophetic example is not binding. Although the various aspects and features have been described with respect to various embodiments and examples herein, it will be understood that any of same is not limiting with respect to the full scope of the appended claims.

What is claimed is:

1. A compound having the formula:

wherein:

$Q_1$ is a fluorescent nucleic acid dye constituent;

$Q_2$ is a fluorescent nucleic acid dye constituent;

$Q_1$ and $Q_2$ may be the same or different, wherein:

(i) each of $Q_1$ and $Q_2$ is independently a phenanthridium dye of Formula I:

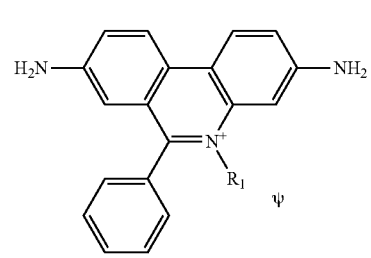

(Formula I)

$R_1$ represents where BRIDGE attaches to the structure; and $\Psi$ is an anion; or (ii) each of $Q_1$ and $Q_2$ is independently an asymmetric cyanine dye, wherein each of $Q_1$ and $Q_2$ dye constituents has a structure of Formula II:

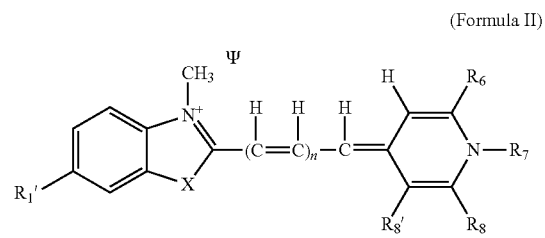

(Formula II)

wherein $R_1'$ of Formula II is H; alkyl or alkenyl having 1 carbon to 6 carbons, inclusive; a halogen; —$OR_9$; —$SR_{10}$; —$NR_{11}R_{12}$; —CN; —NH(C=O)$R_{13}$; —NHS(=O)$_2R_{14}$; —C(=O)NH$R_{15}$; or a substituent associated with minor groove binding; or represents where BRIDGE attaches to the structure;

when $R_1'$ of Formula II comprises at least one of $R_9$, $R_{10}$, $R_{11}$, $R_{12}$, $R_{13}$, $R_{14}$ and $R_{15}$, any said one of $R_9$, $R_{10}$, $R_{11}$, $R_{12}$, $R_{13}$, $R_{14}$ and $R_{15}$, independently, is H or alkyl having 1 carbon to 12 carbons, inclusive, optionally incorporating 1 to 2 nitrogen(s), inclusive, or an aryl;

when $R_1'$ of Formula II comprises $R_{11}$ and $R_{12}$, $R_{11}$ and $R_{12}$ may in combination form a 5- or 6-membered, saturated or unsaturated ring, which optionally comprises at least one hetero atom selected from N and O;

X of Formula II is selected from O and S;

n of Formula II is selected from 0, 1, and 2;

$R_6$ of Formula II is H; alkyl or alkenyl having 1 carbon to 10 carbons, inclusive, optionally comprising at least one hetero atom selected from N, O, and S; a halogen; —$OR_{16}$; —$SR_{16}$; —$NR_{16}R_{17}$; or a substituted or an unsubstituted aryl, optionally comprising 1 to 3 hetero atom(s), inclusive, selected from N, O, and S; or represents where BRIDGE attaches to the structure;

$R_7$ of Formula II is H; alkyl or alkenyl having 1 carbon to 10 carbons, inclusive, optionally comprising an aryl and at least one hetero atom selected from N, O, and S; or a substituted or an unsubstituted aryl optionally comprising 1 to 3 hetero atom(s), inclusive, selected from N, O, and S; or represents where BRIDGE attaches to the structure;

$R_8$ and $R_8'$ of Formula II in combination form a fused aromatic ring, which may be further substituted 1 to 4 time(s), inclusive, independently, by C1-C2, inclusive, alkyl, C1-C2, inclusive, alkoxy, C1-C2, inclusive, alkylmercapto, or a halogen;

each of $R_{16}$ and $R_{17}$ independently is H; alkyl having 1 carbon to 12 carbons, inclusive, optionally incorporating 1 to 2 nitrogen(s) or an aryl; or $R_{16}$ and $R_{17}$ may in combination form a 5- or 6-membered saturated or unsaturated ring, which optionally comprises at least one hetero atom selected from N and O;

only one of $R_1'$, $R_6$, and $R_7$ of Formula II represents where BRIDGE attaches to the structure; and $\Psi$ of Formula II is an anion; or (iii) each of $Q_1$ and $Q_2$ is independently an acridine dye of Formula III:

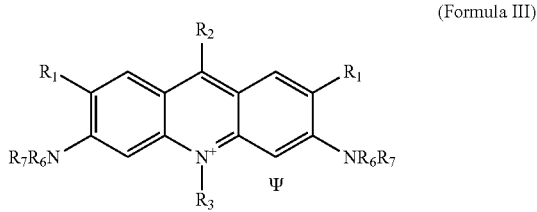

(Formula III)

wherein each $R_1$ of Formula III is independently H or a C1-C2, inclusive, alkyl;

one of $R_2$ and $R_3$ of Formula III represents where BRIDGE attaches to the structure;

when $R_2$ represents where BRIDGE attaches to the structure, $R_3$ is H or —CH$_3$;

when $R_3$ represents where BRIDGE attaches to the structure, $R_2$ is selected from H, —CH$_3$, —NH$_2$, —NHCH$_3$, —CN, and —C(=O)NH$_2$;

each $R_6$ of Formula III is independently H or a C1-C2, inclusive, alkyl;

each $R_7$ of Formula III is independently H or a C1-C2, inclusive, alkyl;

for each pair of adjacent $R_6$ or $R_7$ and $R_1$, independently, $R_6$ or $R_7$ and $R_1$ may in combination form a 5- or 6-membered, saturated or unsaturated ring;

$\Psi$ of Formula III is an anion; and

BRIDGE is an aliphatic linker comprising from 8 to 150 non-hydrogen atoms, inclusive, and the linker comprises no more than one positive charge.

2. The compound of claim 1, wherein BRIDGE has the formula:

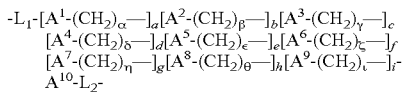

wherein each of $L_1$ and $L_2$, independently, is a moiety comprising a single bond; a polymethylene unit having 1 carbon to 12 carbons, inclusive, optionally comprising at least one hetero atom selected from N, O and S; or an aryl optionally comprising at least one hetero atom selected from N, O and S;

each of $A^1, A^2, A^3, A^4, A^5, A^6, A^7, A^8, A^9$, and $A^{10}$, independently, is a nucleic-acid-binding-enhancing-group (NABEG); a branched alkyl optionally comprising at least one hetero atom selected from N, O and S; or at least one saturated 5- or 6-membered ring, optionally comprising at least one hetero atom selected from N, O and S; or an aryl group optionally comprising at least one hetero atom selected from halogens, N, O, and S;

each of $\alpha, \beta, \gamma, \delta, \epsilon, \zeta, \eta, \theta$, and $\iota$, independently, is zero or an integer from 1 to 20, inclusive; and each of a, b, c, d, e, f, g, h, and i, independently, is zero or an integer from 1 to 20, inclusive.

3. The compound of claim 2, wherein BRIDGE has the formula:

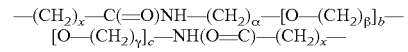

wherein each x, independently, is an integer selected from 1 to 11, inclusive; a is an integer selected from 2 to 20, inclusive; each of $\beta$ and $\gamma$, independently, is 2 or 3; b is zero or an integer from 1 to 20, inclusive; and c is zero or 1.

4. The compound of claim 1, wherein each of $Q_1$ and $Q_2$ is a phenanthridium dye of Formula I:

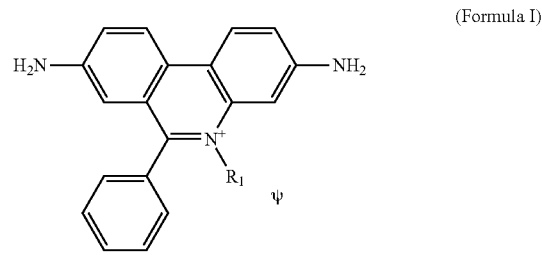

(Formula I)

$R_1$ represents where BRIDGE attaches to the structure; and $\Psi$ is an anion; and BRIDGE has the formula:

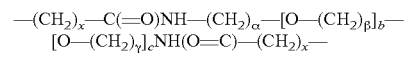

wherein each x, independently, is an integer selected from 1 to 11, inclusive; a is an integer selected from 2 to 20, inclusive; each of $\beta$ and $\gamma$, independently, is 2 or 3; b is zero or an integer from 1 to 20, inclusive; and c is zero or 1.

5. The compound of claim 4, wherein x is 5; $\alpha$ and $\gamma$ are the same and are 2 or 3; $\beta$ is 2; and b is 0, 1, 2, or 3.

6. The compound of claim 4, wherein the compound has the structure:

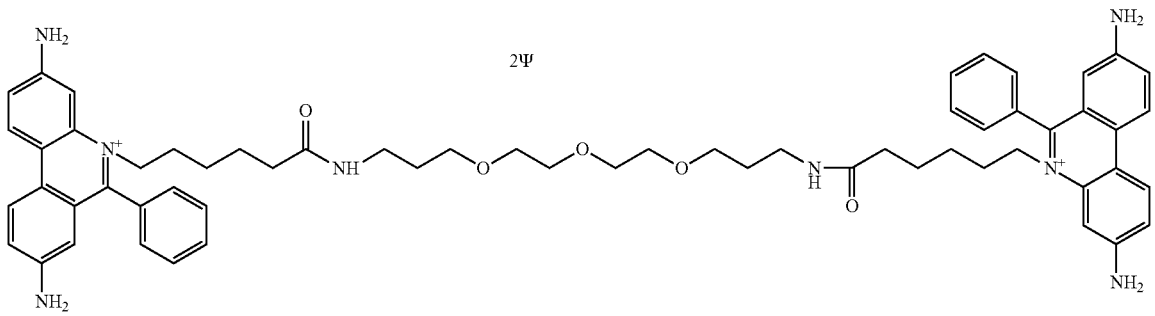

wherein $\Psi$ is I$^-$ or Cl$^-$.

7. The compound of claim 1, wherein each of $Q_1$ and $Q_2$ is an asymmetric cyanine dye, and wherein each of $Q_1$ and $Q_2$ dye constituents independently has a structure of Formula II:

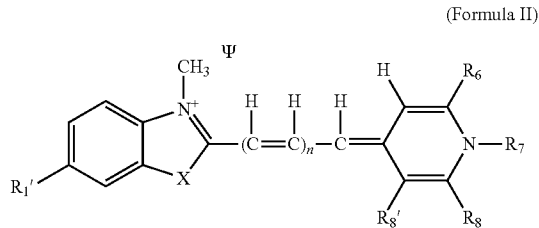

(Formula II)

wherein $R_1'$ of Formula II is H; alkyl or alkenyl having 1 carbon to 6 carbons, inclusive; a halogen; —$OR_9$; —$SR_{10}$; —$NR_{11}R_{12}$; —CN; —NH(C=O)$R_{13}$; —NHS(=O)$_2R_{14}$; —C(=O)NH$R_{15}$; or a substituent associated with minor groove binding; or represents where BRIDGE attaches to the structure;

when $R_1'$ of Formula II comprises at least one of $R_9$, $R_{10}$, $R_{11}$, $R_{12}$, $R_{13}$, $R_{14}$ and $R_{15}$, any said one of $R_9$, $R_{10}$, $R_{11}$, $R_{12}$, $R_{13}$, $R_{14}$ and $R_{15}$, independently, is H or alkyl having 1 carbon to 12 carbons, inclusive, optionally incorporating 1 to 2 nitrogen(s), inclusive, or an aryl;

when $R_1'$ of Formula II comprises $R_{11}$ and $R_{12}$, $R_{11}$ and $R_{12}$ may in combination form a 5- or 6-membered, saturated or unsaturated ring, which optionally comprises at least one hetero atom selected from N and O;

X of Formula II is selected from O and S;

n of Formula II is selected from 0, 1, and 2;

$R_6$ of Formula II is H; alkyl or alkenyl having 1 carbon to 10 carbons, inclusive, optionally comprising at least one hetero atom selected from N, O, and S; a halogen; —$OR_{16}$; —$SR_{16}$; —$NR_{16}R_{17}$; or a substituted or an unsubstituted aryl, optionally comprising 1 to 3 hetero atom(s), inclusive, selected from N, O, and S; or represents where BRIDGE attaches to the structure;

$R_7$ of Formula II is H; alkyl or alkenyl having 1 carbon to 10 carbons, inclusive, optionally comprising an aryl and at least one hetero atom selected from N, O, and S; or a substituted or an unsubstituted aryl optionally comprising 1 to 3 hetero atom(s), inclusive, selected from N, O, and S; or represents where BRIDGE attaches to the structure;

$R_8$ and $R_8'$ of Formula II in combination form a fused aromatic ring, which may be further substituted 1 to 4 time(s), inclusive, independently, by C1-C2, inclusive, alkyl, C1-C2, inclusive, alkoxy, C1-C2, inclusive, alkylmercapto, or a halogen;

each of $R_{16}$ and $R_{17}$ independently is H; alkyl having 1 carbon to 12 carbons, inclusive, optionally incorporating 1 to 2 nitrogen(s) or an aryl; or $R_{16}$ and $R_{17}$ may in combination form a 5- or 6-membered saturated or unsaturated ring, which optionally comprises at least one hetero atom selected from N and O;

only one of $R_1'$, $R_6$, and $R_7$ of Formula II represents where BRIDGE attaches to the structure; and Ψ of Formula II is an anion; and BRIDGE has the formula:

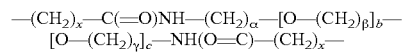

wherein each x, independently, is an integer selected from 1 to 11, inclusive; a is an integer selected from 2 to 20, inclusive; each of β and γ, independently, is 2 or 3; b is zero or an integer from 1 to 20, inclusive; and c is zero or 1.

8. The compound of claim 7, wherein each of $Q_1$ and $Q_2$ has the structure:

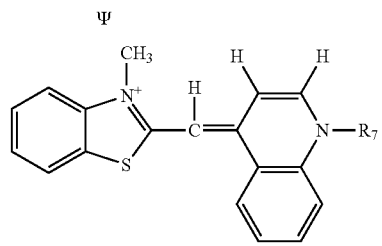

wherein $R_7$ represents where BRIDGE attaches to the structure.

9. The compound of claim 7, wherein the compound has the structure:

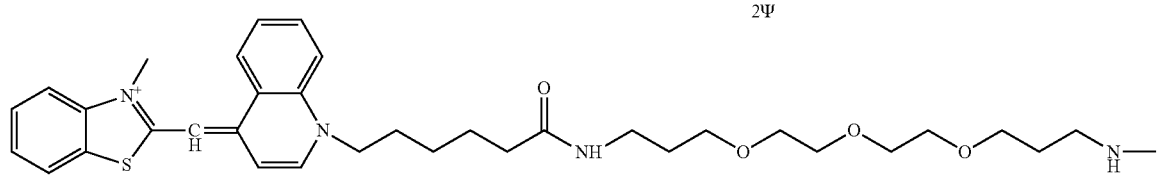

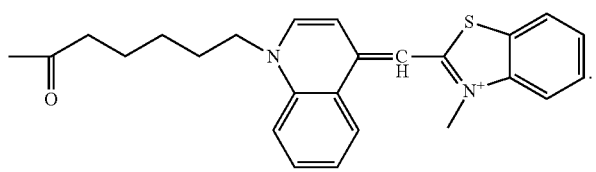

10. The compound of claim 1, wherein each of $Q_1$ and $Q_2$ is independently an acridine dye of Formula III:

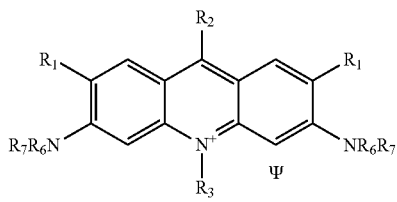

wherein each $R_1$ of Formula III is independently H or a C1-C2, inclusive, alkyl;

one of $R_2$ and $R_3$ of Formula III represents where BRIDGE attaches to the structure;

when $R_2$ represents where BRIDGE attaches to the structure, $R_3$ is H or —$CH_3$;

when $R_3$ represents where BRIDGE attaches to the structure, $R_2$ is selected from H, —$CH_3$, —$NH_2$, —$NHCH_3$, —CN, and —C(=O)$NH_2$;

each $R_6$ of Formula III is independently H or a C1-C2, inclusive, alkyl;

each $R_7$ of Formula III is independently H or a C1-C2, inclusive, alkyl;

for each pair of adjacent $R_6$ or $R_7$ and $R_1$, independently, $R_6$ or $R_7$ and $R_1$ may in combination form a 5- or 6-membered, saturated or unsaturated ring;

$\Psi$ of Formula III is an anion; and

BRIDGE has the formula:

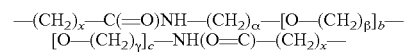

wherein each x, independently, is an integer selected from 1 to 11, inclusive; a is an integer selected from 2 to 20, inclusive; each of β and γ, independently, is 2 or 3; b is zero or an integer from 1 to 20, inclusive; and c is zero or 1.

11. The compound of claim 4, wherein each $R_1$ is H; $R_2$ is H; $R_3$ represents where BRIDGE attaches to the structure; each $R_6$ is —$CH_3$; and each $R_7$ is —$CH_3$.

12. The compound of claim 11, wherein the compound has the structure:

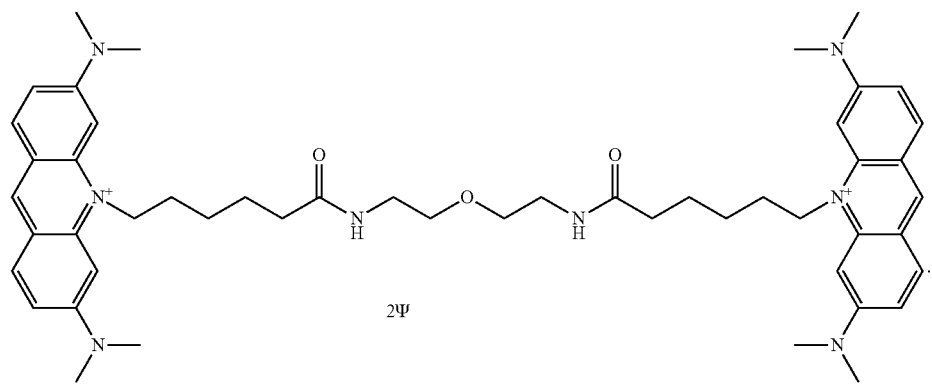 [SMILES: CN(C)c1ccc2cc3ccc(N(C)C)cc3[n+](CCCCCC(=O)NCCOCCNC(=O)CCCCC[n+]3c4cc(N(C)C)ccc4cc4ccc(N(C)C)cc43)c2c1]

13. The compound of any one of claims 1-12, wherein ψ is I⁻ or Cl⁻.

14. A kit for determining presence or absence of nucleic acid in a sample, the kit comprising: a compound according to any one of claims 1-13; optionally, a buffer; and information concerning use of the kit.

15. The compound of claim 2, wherein the Bridge comprises a weakly basic constituent.

16. The compound of claim 15, wherein the Bridge comprises an aryl group comprising at least one Nitrogen atom.

17. The compound of claim 16, wherein the Bridge comprises a pyridine group, pyrazine group, triazole group, or tetrazole group.

18. The compound of claim 2, wherein at least one of $A^1$, $A^2$, $A^3$, $A^4$, $A^5$, $A^6$, $A^7$, $A^8$, $A^9$, and $A^{10}$ independently comprises an aryl group; the aryl group optionally comprising at least one hetero atom selected from halo, N, O, and S.

19. The compound of claim 18, wherein at least one of $A^1$, $A^2$, $A^3$, $A^4$, $A^5$, $A^6$, $A^7$, $A^8$, $A^9$, and $A^{10}$ independently comprises an aryl group; the aryl group comprising at least one Nitrogen atom.

20. The compound of claim 19, wherein at least one of $A^1$, $A^2$, $A^3$, $A^4$, $A^5$, $A^6$, $A^7$, $A^8$, $A^9$, and $A^{10}$ independently comprises a pyridine group, a pyrazine group, a triazole group, or a tetrazole group.

21. The compound of claim 20, wherein at least one of $A^1$, $A^2$, $A^3$, $A^4$, $A^5$, $A^6$, $A^7$, $A^8$, $A^9$, and $A^{10}$ independently comprises a triazole group.

22. The compound of claim 21, wherein at least one of $A^1$, $A^2$, $A^3$, $A^4$, $A^5$, $A^6$, $A^7$, $A^8$, $A^9$, and $A^{10}$, independently comprises a 1,2,3-triazole group.

\* \* \* \* \*